US008449520B2

(12) United States Patent
Pepper et al.

(10) Patent No.: US 8,449,520 B2
(45) Date of Patent: May 28, 2013

(54) APPARATUS AND METHODS FOR MAKING, STORING, AND ADMINISTERING FREEZE-DRIED MATERIALS SUCH AS FREEZE-DRIED PLASMA

(75) Inventors: Clinton B. Pepper, West Linn, OR (US); Simon J. McCarthy, Portland, OR (US); Lisa A. Buckley, Portland, OR (US); Eric K. Meyer, Hillsboro, OR (US)

(73) Assignee: HemCon Medical Technologies Inc., Portland, OR (US)

( * ) Notice: Subject to any disclaimer, the term of this patent is extended or adjusted under 35 U.S.C. 154(b) by 1163 days.

(21) Appl. No.: 12/228,745

(22) Filed: Aug. 15, 2008

(65) Prior Publication Data
US 2009/0113753 A1 May 7, 2009

Related U.S. Application Data

(63) Continuation-in-part of application No. 12/077,397, filed on Mar. 19, 2008, which is a continuation-in-part of application No. 11/881,493, filed on Jul. 27, 2007, now abandoned, which is a continuation-in-part of application No. 11/725,352, filed on Mar. 19, 2007, now Pat. No. 7,776,022.

(51) Int. Cl.
*A61B 19/00* (2006.01)
*F26B 5/06* (2006.01)

(52) U.S. Cl.
USPC .............................. 604/403; 604/410; 34/284

(58) Field of Classification Search
USPC ............ 604/403–416; 34/284, 92; 383/210.1; 206/363
See application file for complete search history.

(56) References Cited

U.S. PATENT DOCUMENTS

| 2,150,620 A | 3/1939 | Frost |
| 3,942,529 A | 3/1976 | Waage |
| 4,035,924 A | 7/1977 | Faure |
| 4,112,989 A | 9/1978 | Grode et al. |
| 4,469,227 A | 9/1984 | Faust |
| 4,505,708 A | 3/1985 | Gajewski et al. |
| 4,619,650 A | 10/1986 | Wisdom |
| 4,664,913 A | 5/1987 | Mielke et al. |

(Continued)

FOREIGN PATENT DOCUMENTS

| WO | WO 97/20181 | 6/1997 |
| WO | WO 99/02169 | 1/1999 |
| WO | WO 2007/027178 | 3/2007 |
| WO | WO2008/048228 | 4/2008 |

OTHER PUBLICATIONS

MacKenzie, A.P., "The Physico-Chemical Basis for the Freeze-Drying Process." Develop. Biol. Standard., vol. 36: 51-67, 1977.

(Continued)

*Primary Examiner* — Philip R Wiest
(74) *Attorney, Agent, or Firm* — Miller Nash LLP

(57) ABSTRACT

A flexible container receives a liquid material, which is freeze-dried in situ within the flexible container. A gas permeable material that is separate from the flexible container provides gas transport for sublimation during drying and lyophilization. The gas permeable portion of the system can be isolated and removed from the flexible container post-lyophilzation The freeze-dried material is stored in the flexible container until administration is necessary. The flexible container receives a reconstituting liquid for mixing with the freeze-dried material, and conveys the reconstituted freeze-dried material from the flexible container for administration to an individual.

61 Claims, 34 Drawing Sheets

U.S. PATENT DOCUMENTS

| | | | |
|---|---|---|---|
| 4,813,210 A * | 3/1989 | Masuda et al. | 53/425 |
| 4,878,597 A | 11/1989 | Haast | |
| 4,956,295 A | 9/1990 | Sudoma | |
| 4,973,327 A | 11/1990 | Goodrich, Jr. et al. | |
| 4,994,021 A | 2/1991 | Smith et al. | |
| 4,994,057 A | 2/1991 | Carmen et al. | |
| 5,084,040 A | 1/1992 | Sutter | |
| 5,114,004 A | 5/1992 | Isono et al. | |
| 5,257,983 A | 11/1993 | Garyantes et al. | |
| 5,309,649 A | 5/1994 | Bergmann | |
| 5,342,673 A | 8/1994 | Bowman et al. | |
| 5,368,586 A | 11/1994 | Van Der Heiden et al. | |
| 5,484,428 A | 1/1996 | Drainville et al. | |
| 5,541,294 A | 7/1996 | Horowitz et al. | |
| 5,631,019 A | 5/1997 | Marx | |
| 5,853,388 A | 12/1998 | Semel | |
| D425,205 S | 5/2000 | Henigan et al. | |
| D430,939 S | 9/2000 | Zukor et al. | |
| 6,199,297 B1 | 3/2001 | Wisniewski | |
| 6,288,027 B1 | 9/2001 | Gawryl et al. | |
| 6,398,771 B1 | 6/2002 | Gustafsson et al. | |
| 6,517,526 B1 * | 2/2003 | Tamari | 604/403 |
| 6,669,905 B1 | 12/2003 | Mathias et al. | |
| 6,773,425 B1 | 8/2004 | Tamari | |
| 7,048,709 B2 | 5/2006 | Goudaliez et al. | |
| 7,189,410 B1 | 3/2007 | Drohan et al. | |
| 7,202,341 B2 | 4/2007 | McGinnis et al. | |
| 7,235,063 B2 | 6/2007 | D'Antonio et al. | |
| 7,361,277 B2 | 4/2008 | Bormann et al. | |
| 7,422,726 B2 | 9/2008 | Hammerstedt et al. | |
| 7,456,024 B2 | 11/2008 | Dahm et al. | |
| 7,473,246 B2 | 1/2009 | Vancaillie et al. | |
| 7,621,298 B2 | 11/2009 | Goudaliez et al. | |
| 7,776,022 B2 | 8/2010 | McCarthy et al. | |
| 7,931,919 B2 | 4/2011 | Bakaltcheva et al. | |
| 2002/0189127 A1 | 12/2002 | Akimoto | |
| 2003/0187423 A1 | 10/2003 | Wilkinson et al. | |
| 2004/0081588 A1 * | 4/2004 | Hammerstedt et al. | 422/101 |
| 2005/0277107 A1 | 12/2005 | Toner et al. | |
| 2007/0116729 A1 | 5/2007 | Palepu | |
| 2007/0258960 A1 * | 11/2007 | DeAngelo et al. | 424/93.7 |
| 2008/0031934 A1 * | 2/2008 | MacPhee et al. | 424/449 |
| 2008/0119818 A1 | 5/2008 | Bakaltcheva et al. | |
| 2008/0176209 A1 | 7/2008 | Muller et al. | |
| 2008/0177243 A1 | 7/2008 | Roger | |
| 2008/0234654 A1 | 9/2008 | McCarthy et al. | |
| 2009/0270832 A1 | 10/2009 | Vancaillie et al. | |

OTHER PUBLICATIONS

Gautam et al., "Monoclonal Anti-A Antibody Removal by Synthetic A Antigen Immobilized on Specific Antibody Filters." Biotechnology and Bioengineering; vol. 99, No. 4: 876-883, 2008.

Isarangkura et al., "Fresh Dried Plasma: A Solution for the Shortage of Blood Products in Developing Countries." J. Clinical and Laboratory Research; vol. 17, No. 4: 349-354, 1987.

Maraolis et al., "Ascorbic and Dehydroascorbic Acids Measured in Plasma Preserved with Dithiothreitol or Metaphosphoric Acid." Clin, Chem.; vol. 36, No. 10: 1750-1755, 1990.

Spoerke et al., "Lyophilized Plasma for Resuscitation in a Swine Model of Severe Injury." Arch. Surg.; vol. 144, No. 9: 829-834, 2009.

PCT Notification of Transmittal of International Preliminary Report on Patentability, Jun. 30, 2010; PCT/US09/04592 filed Aug. 11, 2009.

Bakaltcheva et al., "Freeze-dried whole plasma: Evaluating sucrose, trehalose, sorbitol, mannitol and glycine as stabilizers." Thrombosis Research, vol. 120: 105-116, 2007.

* cited by examiner

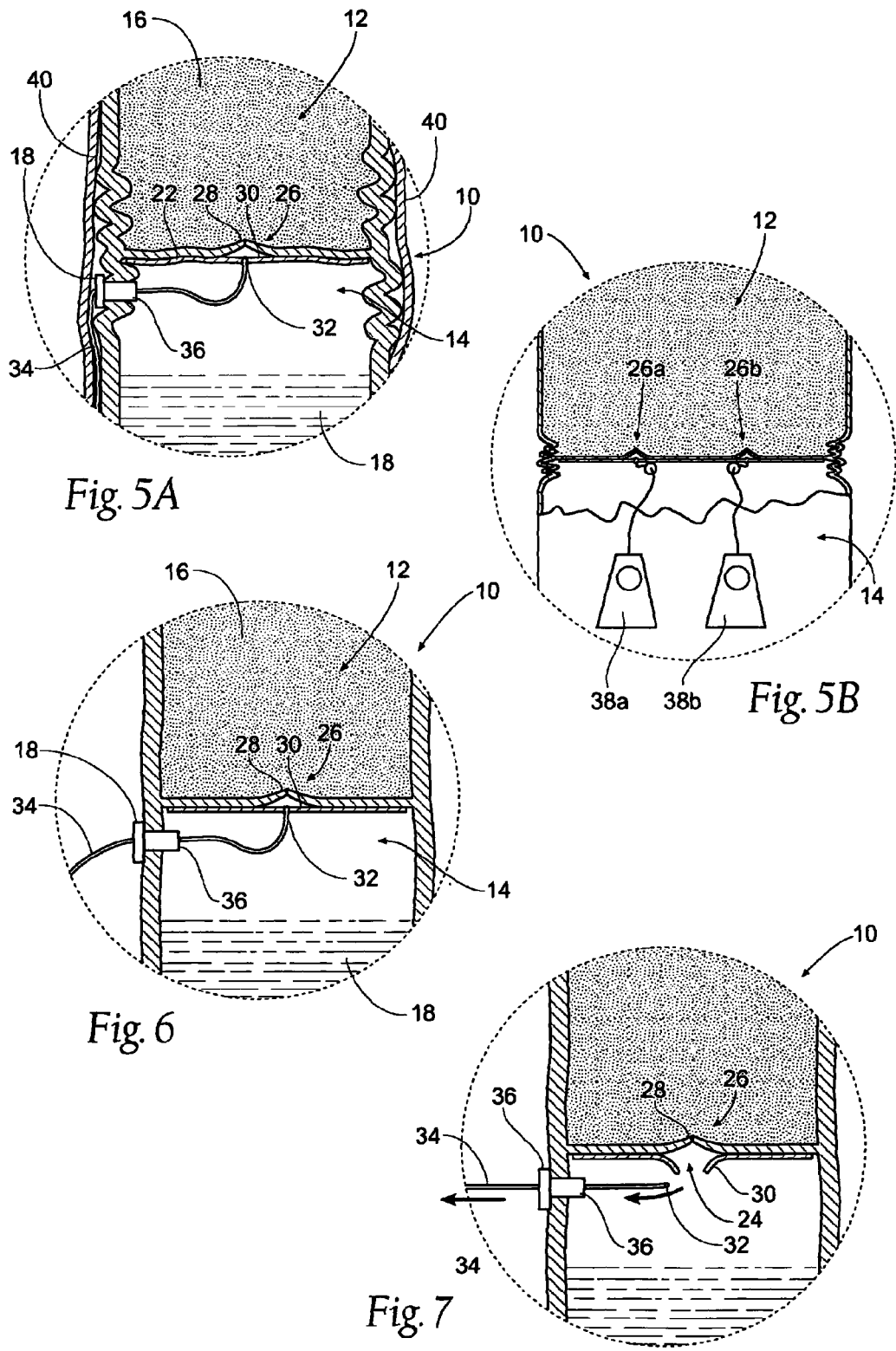

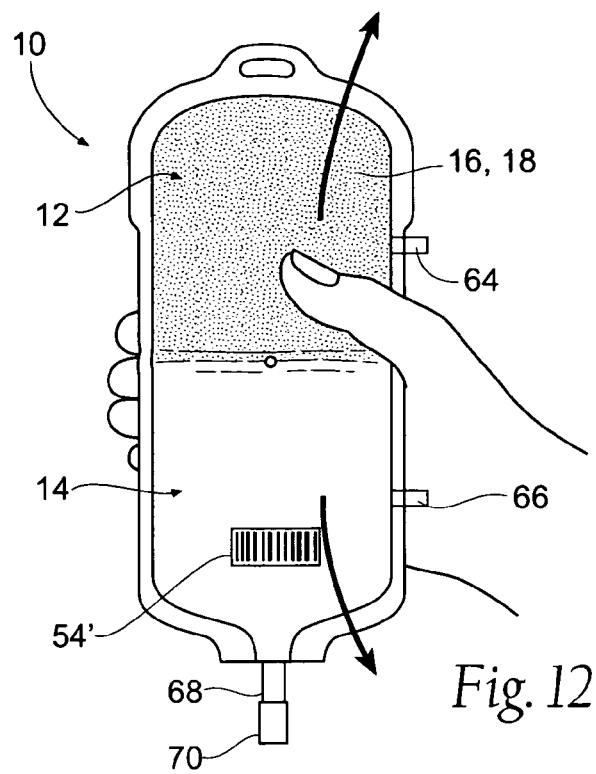
Fig. 12
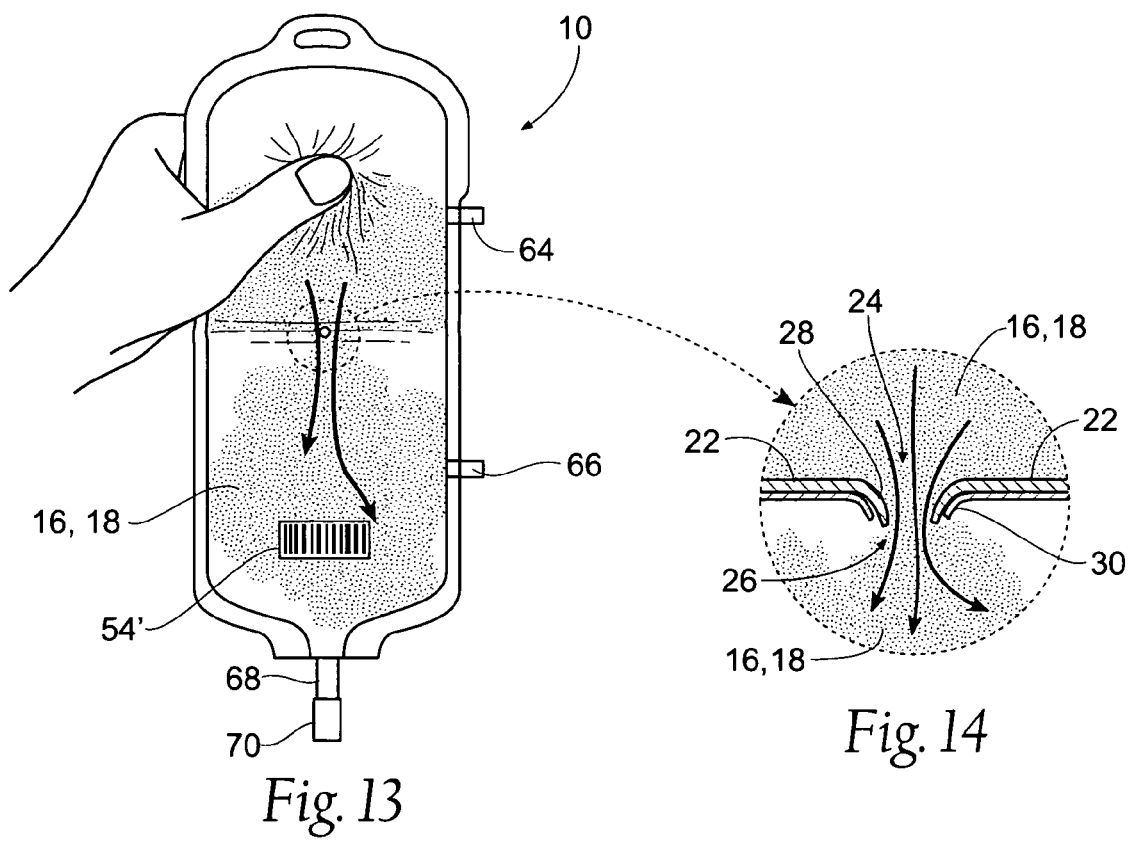
Fig. 13
Fig. 14

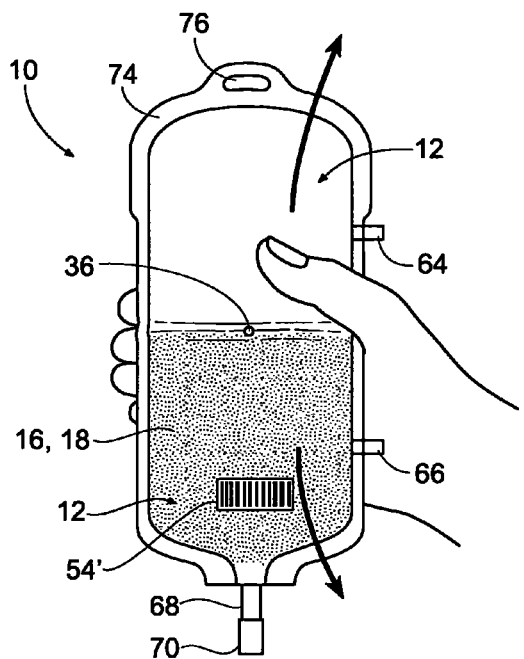
Fig. 15
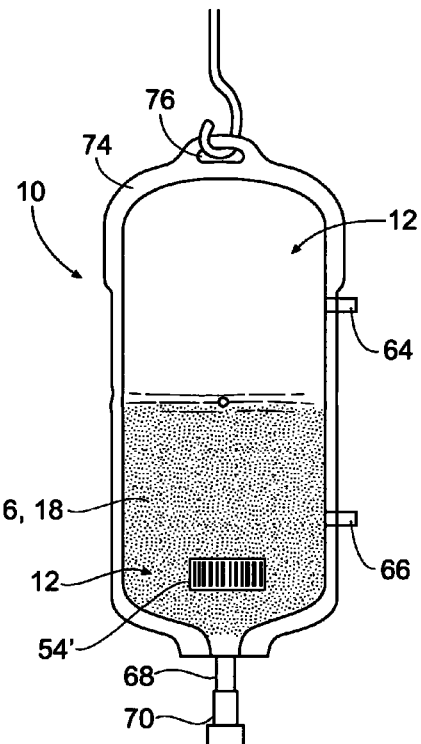
Fig. 16
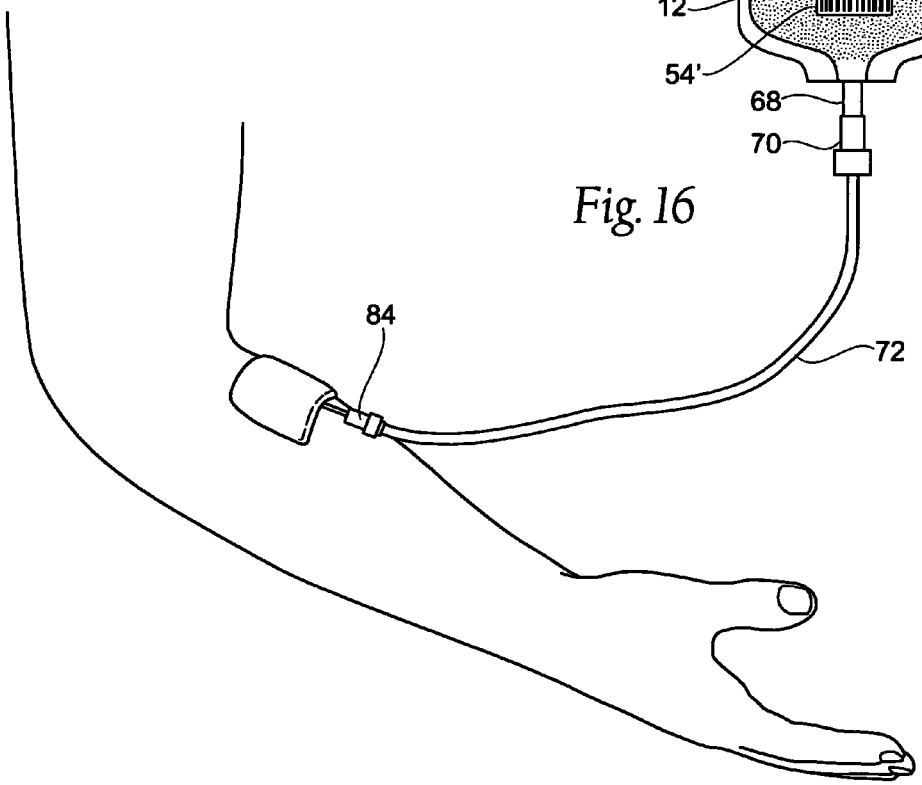

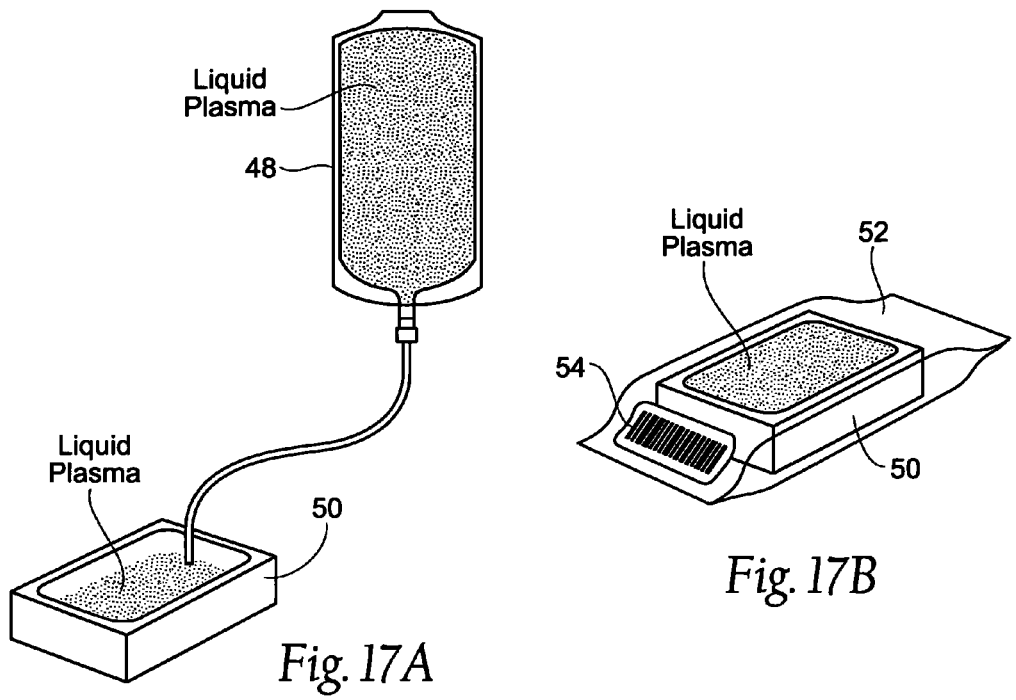
Fig. 17A
Fig. 17B
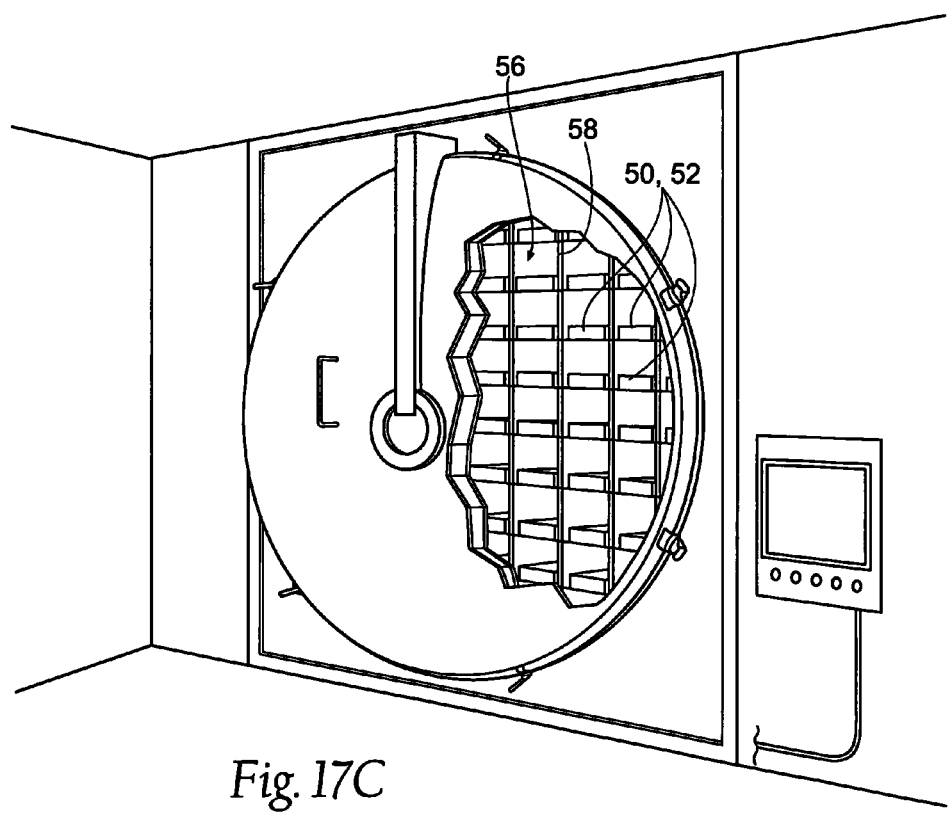
Fig. 17C

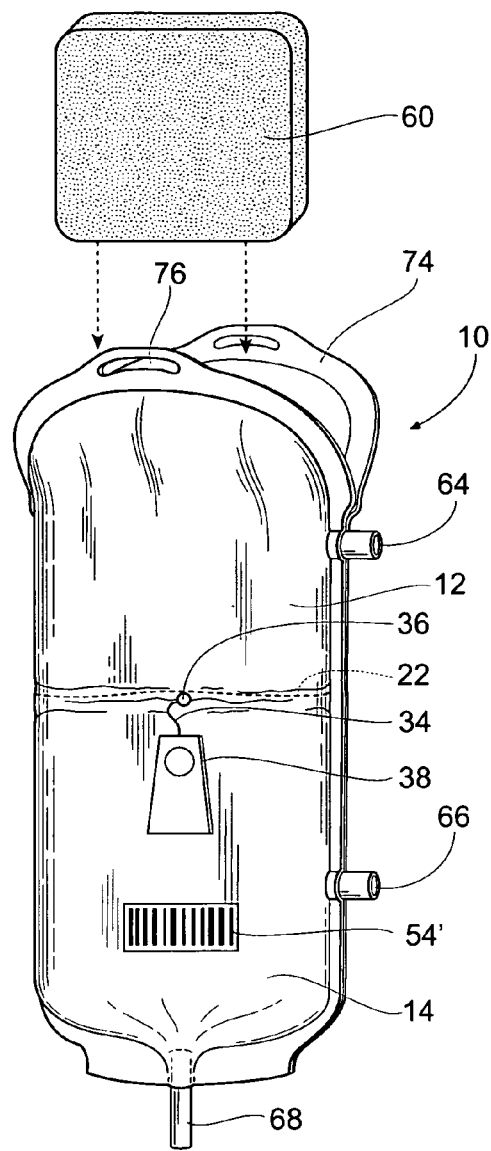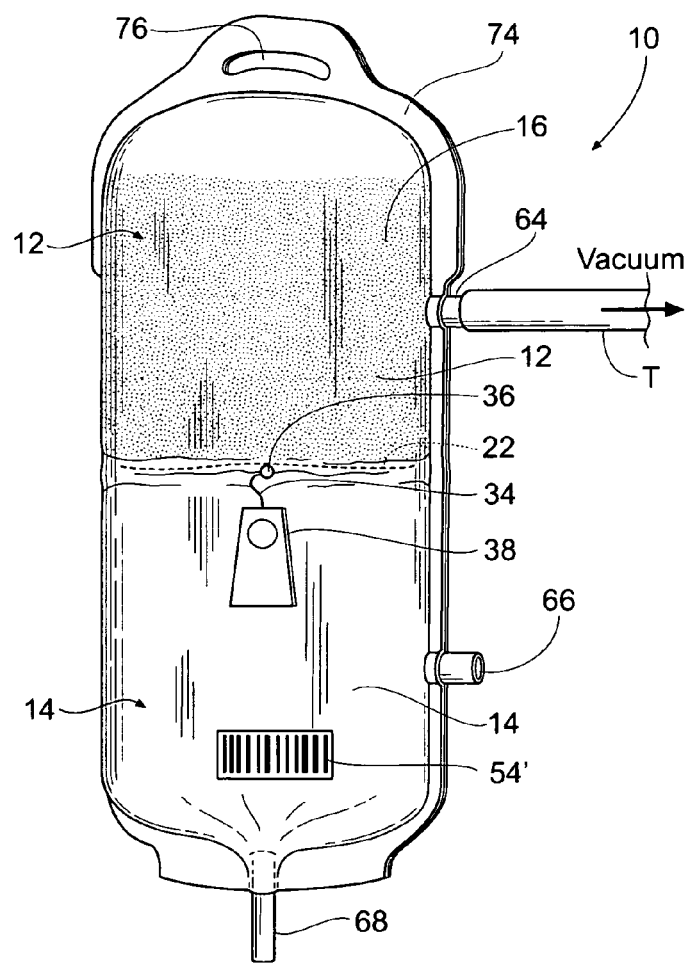
Fig. 18
Fig. 19

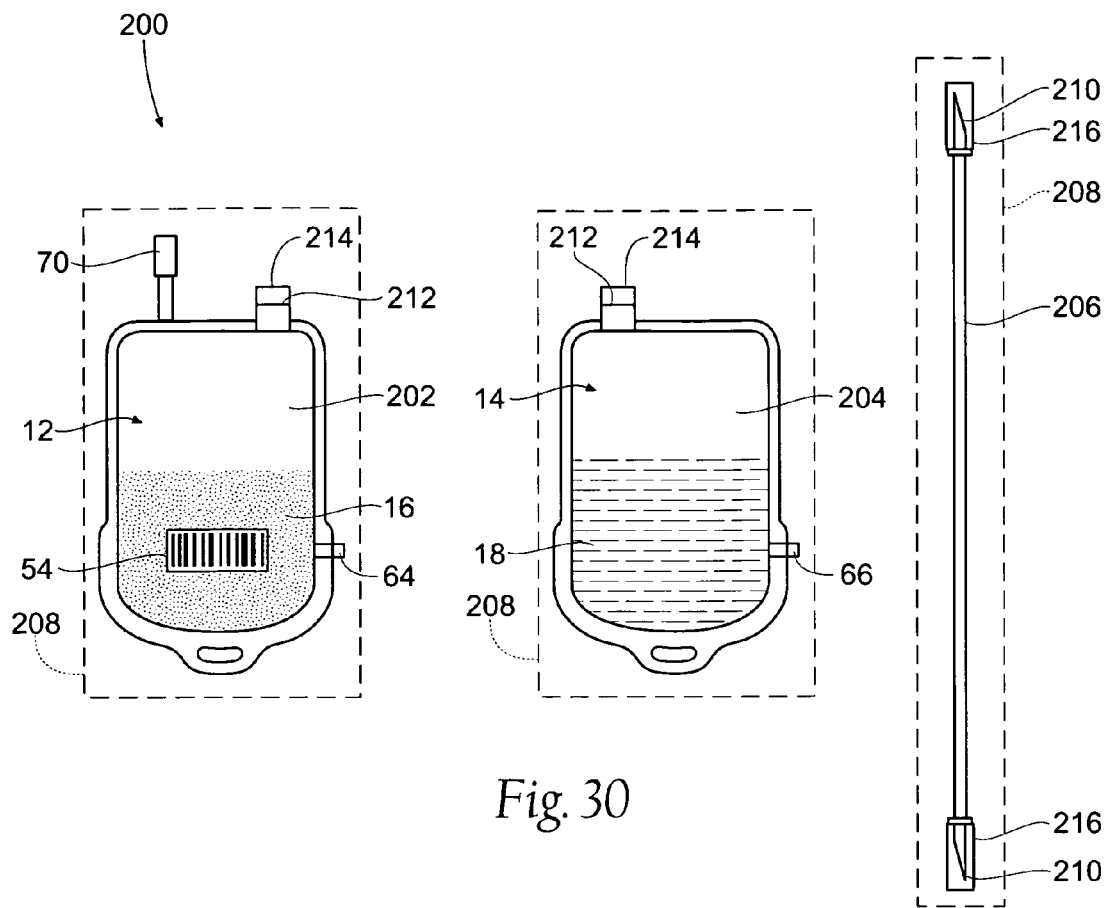
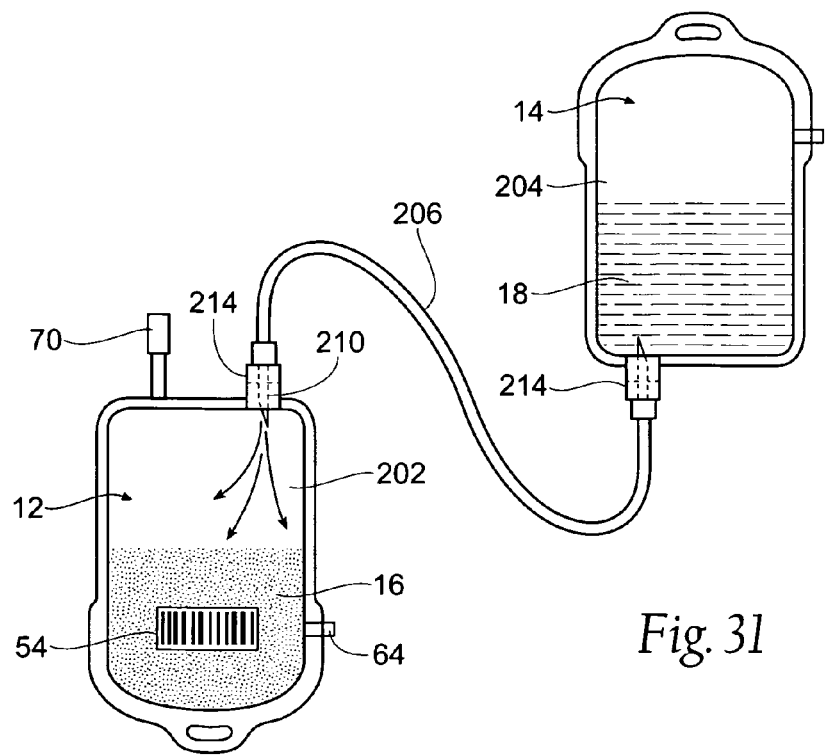
Fig. 30
Fig. 31

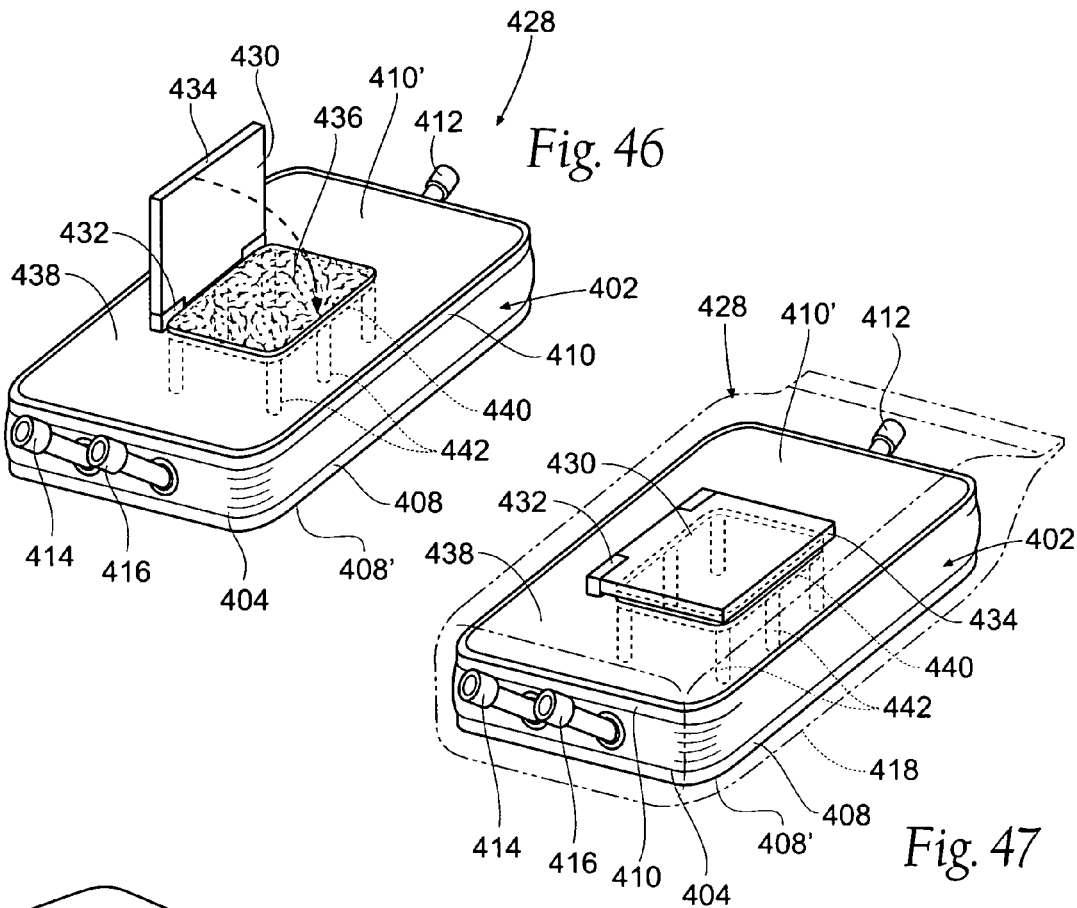
Fig. 46
Fig. 47
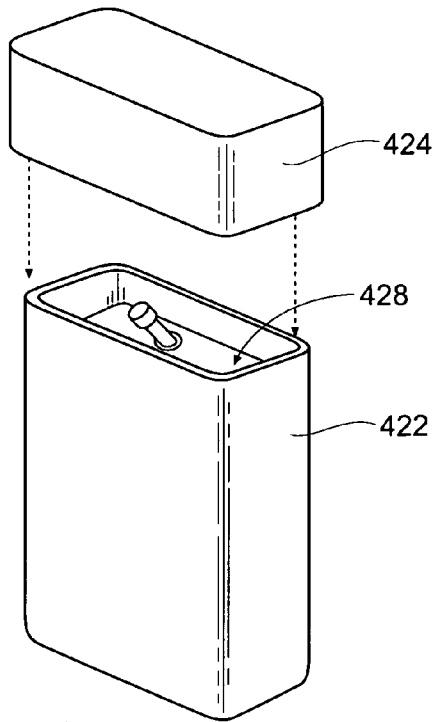
Fig. 48
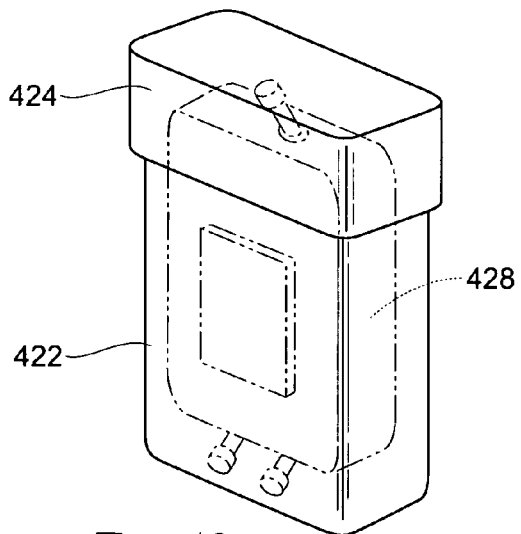
Fig. 49

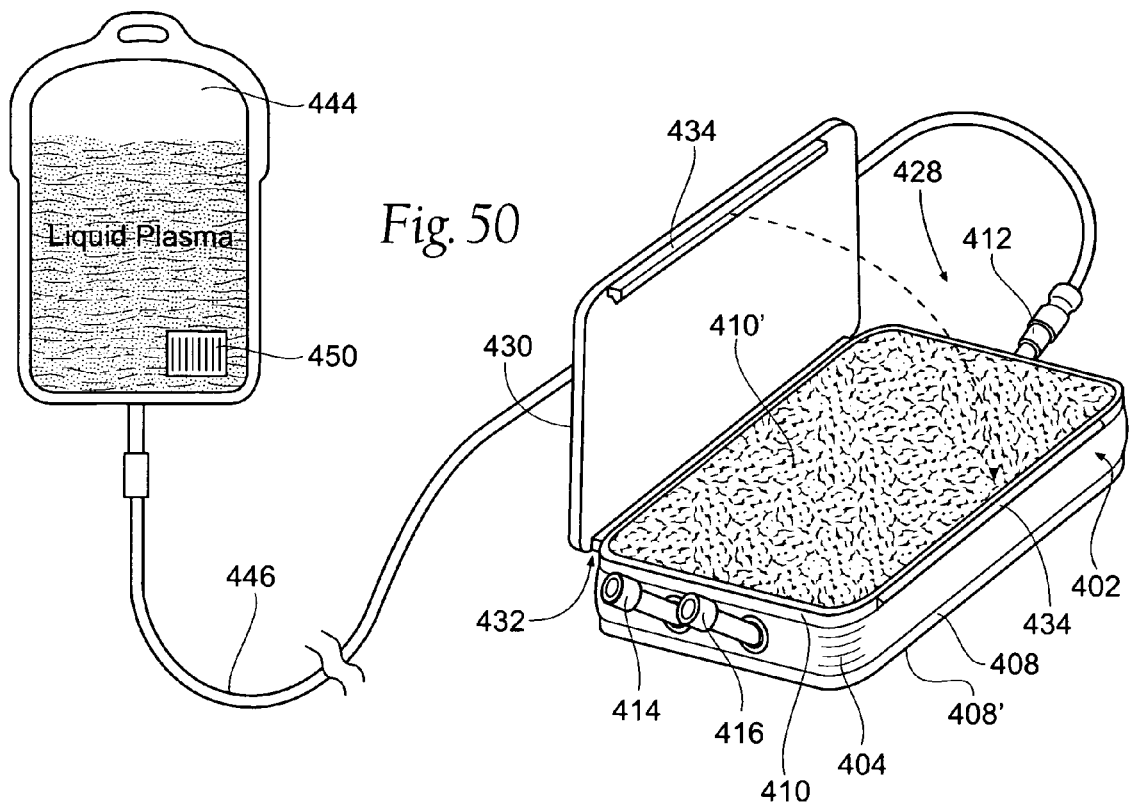
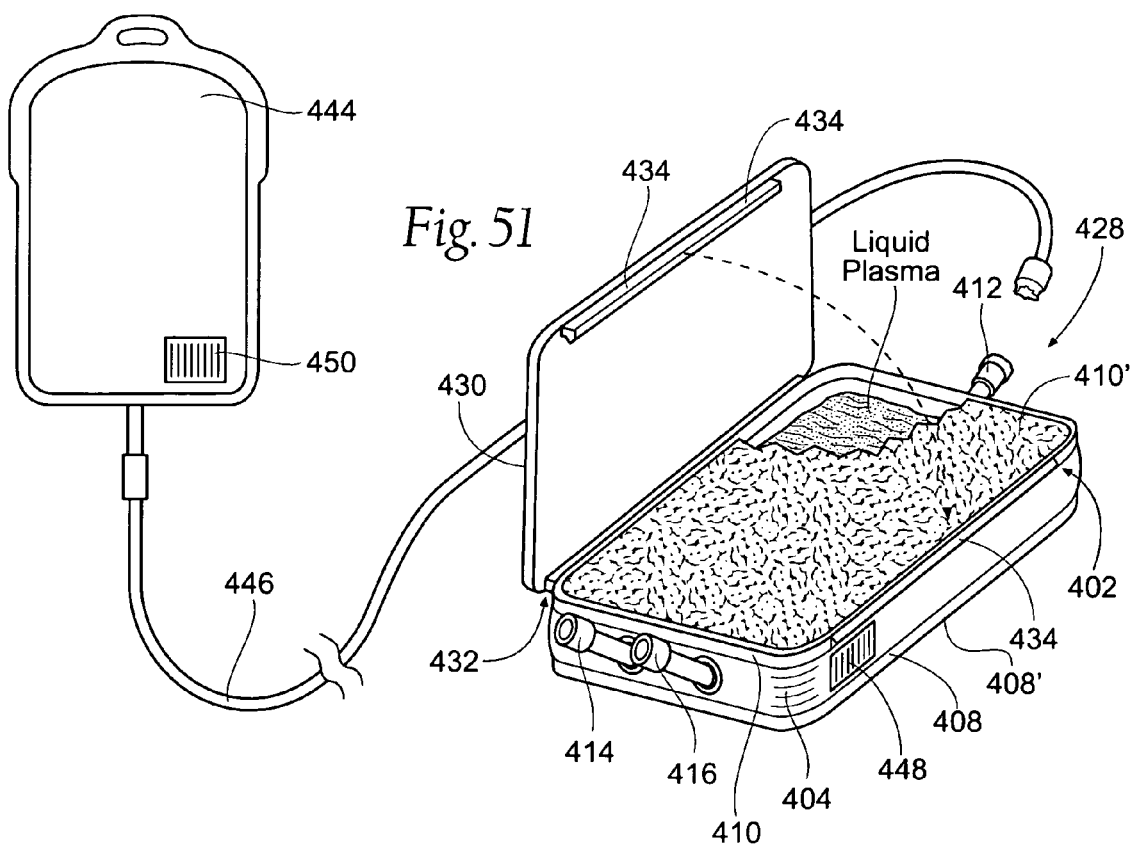

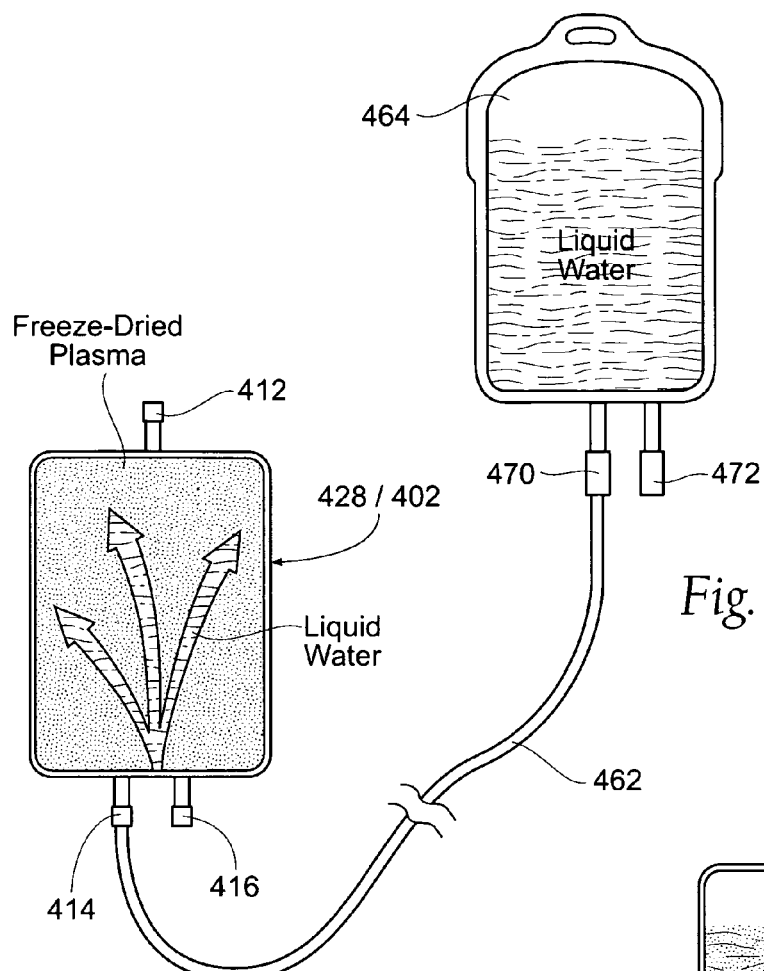
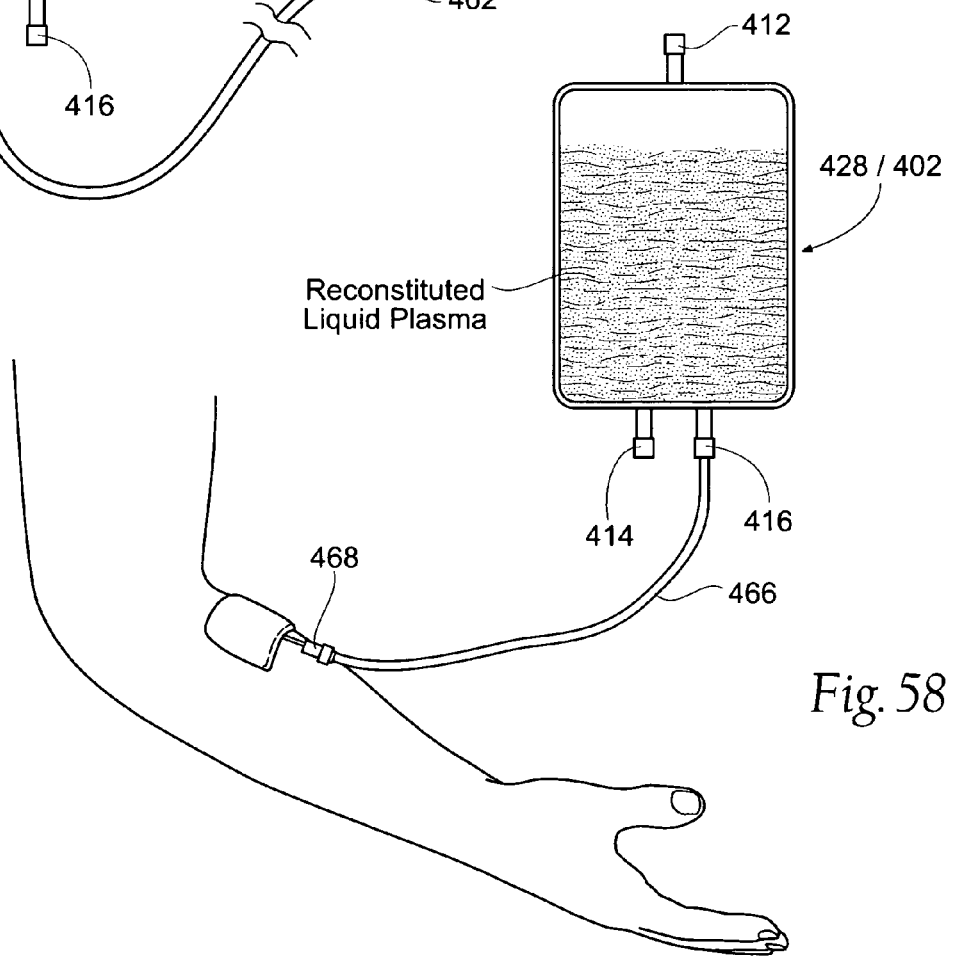
Fig. 57
Fig. 58

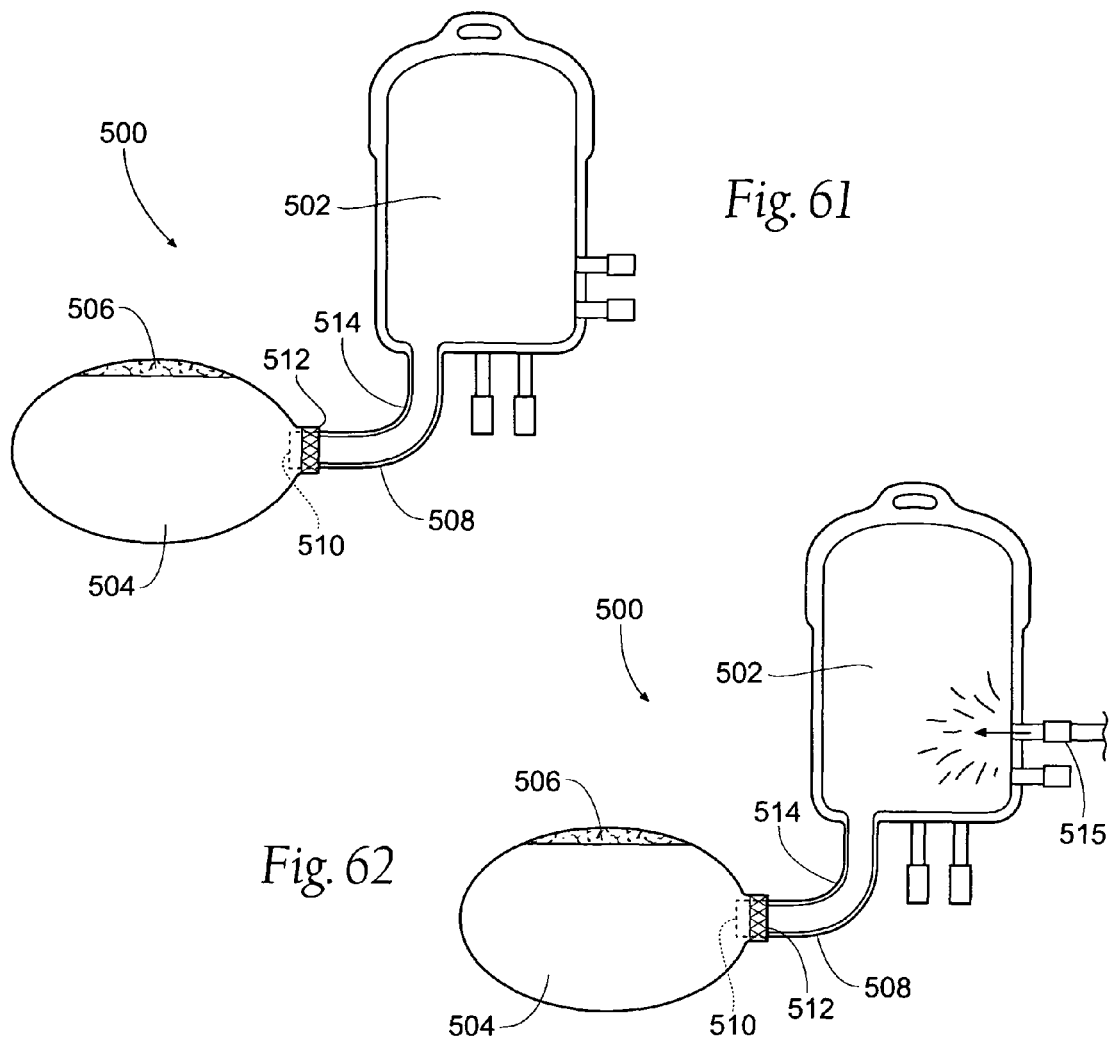
*Fig. 61*
*Fig. 62*
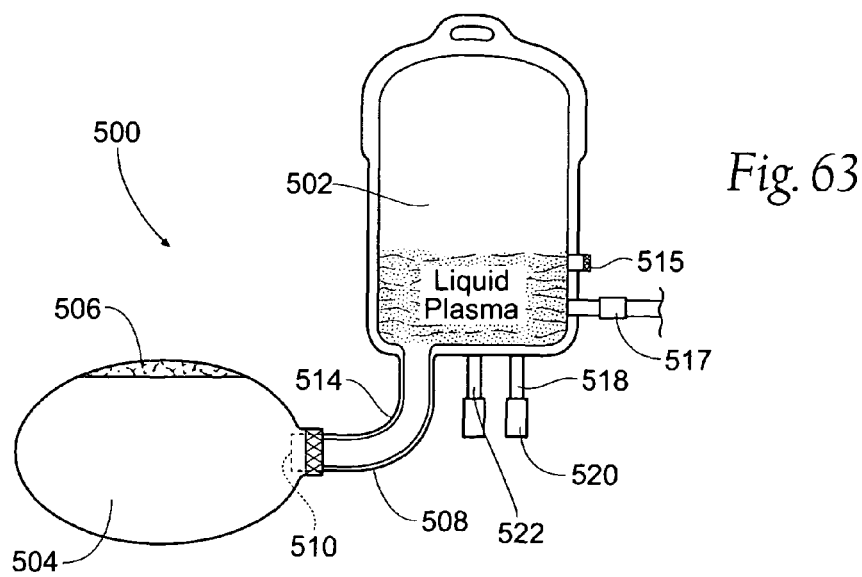
*Fig. 63*

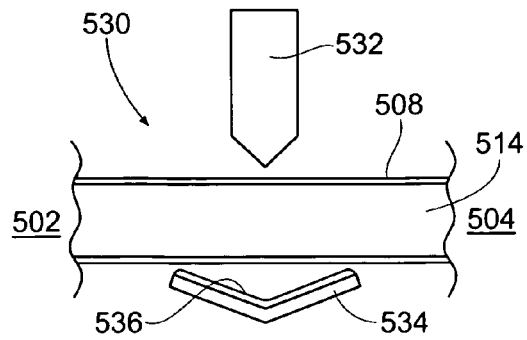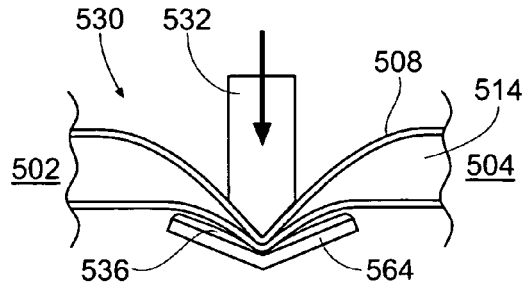
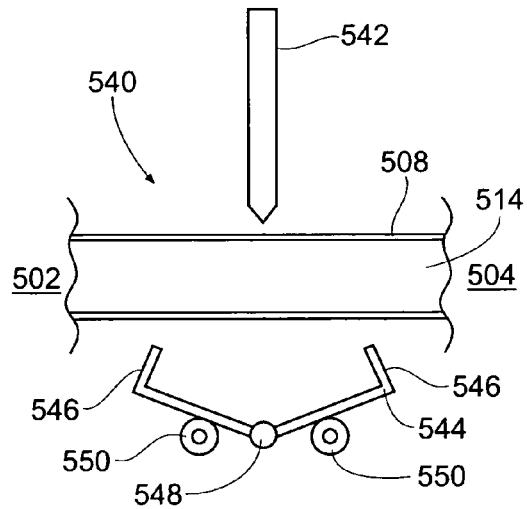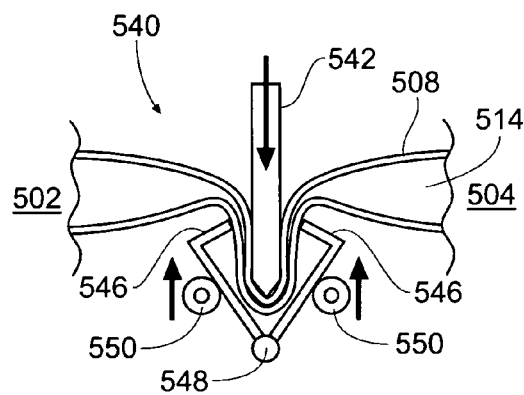
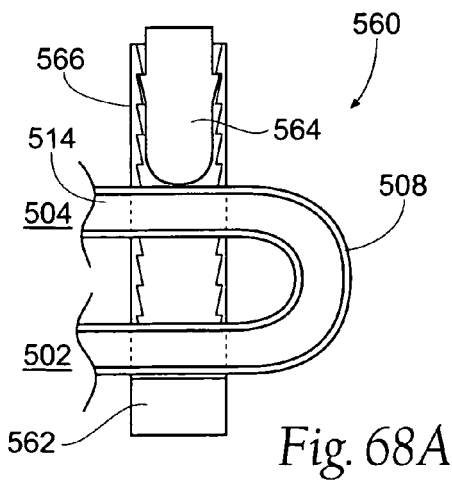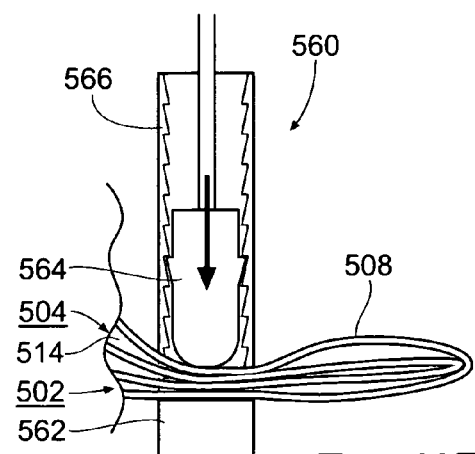

APPARATUS AND METHODS FOR MAKING, STORING, AND ADMINISTERING FREEZE-DRIED MATERIALS SUCH AS FREEZE-DRIED PLASMA

RELATED APPLICATIONS

This application is a continuation-in-part of co-pending U.S. patent application Ser. No. 12/077,397, filed 19 Mar. 2008, entitled "Apparatus and Methods for Making, Storing, and Administering Freeze-Dried Materials Such as Freeze-Dried Plasma", which is a continuation-in-part of U.S. patent application Ser. No. 11/881,493, filed 27 Jul. 2007 now abandoned, which is a continuation-in-part of U.S. patent application Ser. No. 11/725,352, filed 19 Mar. 2007 now U.S. Pat. No. 7,776,022, all of which are incorporated herein by reference.

GOVERNMENT RIGHTS

This invention was made with government support under contract no. W81XWH-08-2-0078 awarded by the U.S. Army Medical Research Acquisition Activity. The government has certain rights in the invention.

FIELD OF THE INVENTION

The present invention relates to methods, systems, and apparatuses for manufacturing, storing and administering freeze-dried materials, such as single donor units of freeze-dried human plasma.

BACKGROUND OF THE INVENTION

First aid is critical for the survival of a person that has suffered a serious injury, such as a trauma victim. For instance, initial treatment of a severely wounded person in combat situations can often mean the difference between life and death. While it is necessary to treat the wounds and stop the bleeding of the person, it is also important to ensure that the person's body is capable of properly functioning. Thus, it is necessary to take steps to ensure that the person's body is properly hydrated after losing fluids due to the injury. The present invention addresses these issues.

Previously, fluids were replenished within the patient by delivering saline intravenously. While effective, research has indicated that delivery of plasma to the patient is even more effective in replenishing fluid to the patient than the use of saline. However, delivery and storage of the plasma is critical to prevent contamination of the plasma. An ideal way of delivering the plasma is to deliver the plasma in a freeze dried form and reconstituting the plasma when it is administered to a person.

SUMMARY OF THE INVENTION

The invention provides methods, systems, and apparatuses for manufacturing, storing and administering freeze-dried materials, such as single donor units of freeze-dried human plasma.

According to one aspect of the invention, a freeze-dried material, e.g., freeze-dried human plasma, is stored in a first chamber of a container along with a reconstituting liquid for the freeze-dried material, e.g., de-gassed water. The reconstituting liquid is stored in a second chamber of the container. A sealing wall within the container forms a barrier between the first chamber and the second chamber preventing contact between the freeze-dried material and the reconstituting liquid. At least one valve assembly in the sealing wall can be manipulated to selectively open at least one region of the sealing wall to establish fluid flow communication between the first and second chambers. This allows the freeze dried material to be reconstituted within the container. The reconstituted freeze-dried material can also be administered directly from the same container to a recipient.

In one arrangement, the valve assembly includes a pressure sensitive valve, e.g., a flap valve. The valve is operative between a normally closed condition, normally resisting fluid flow communication between the first and second chambers, and an opened condition, establishing fluid flow condition communication between the first and second chambers. The pressure sensitive valve can be placed in its open condition in response to establishing a pressure differential across the valve, e.g., by preferentially squeezing a chamber of the container.

In one arrangement, the valve assembly includes a normally closed septum. The septum is operative in a normally closed condition, maintaining closure between the first and second chambers, and an opened condition establishing fluid flow communication between the first and second chambers in response to at least a partially tearing of the septum. The septum can, e.g., include a tear member coupled to a pulling member to at least partially tear open the septum.

The pressure sensitive valve and the septum can be arranged serially to provide a redundant valve assembly. In this arrangement, the normally closed septum is operative in a normally closed condition, maintaining closure between the first and second chambers, independent of the valve and an opened condition establishing fluid flow communication between the first and second chambers in response to at least a partially tearing of the septum and a pressure differential applied across the valve.

In one arrangement, an outer skirt is provided that overlays an exterior wall of the container in a region of the sealing wall. The outer skirt can include a tear member coupled to a pulling member to tear open the outer skirt for removal.

Another embodiment of the invention provides a method that provides a flexible container as above generally described, with first and second chambers. The first chamber holds a freeze-dried material, such as freeze-dried human plasma, in a dry state. The second chamber holds a reconstituting liquid for the freeze-dried material. An interior sealing wall within the container is sized and configured to form a barrier between the first chamber and the second chamber preventing contact between the freeze-dried material and the reconstituting liquid. At least one valve assembly in the sealing wall is operative by manipulation to open at least one region of the sealing wall to establish fluid flow communication between the first and second chambers. According to this aspect of the invention, the valve assembly is manipulated to open the region, and the reconstituting liquid is expressed from the second chamber through the valve assembly into the first chamber into contact with the freeze-dried material.

In one arrangement, an outer skirt overlays an exterior wall of the container in a region of the sealing wall and blocking manipulation of the valve assembly. In this arrangement, the outer skirt is removed to expose the valve assembly to manipulation prior to manipulating the valve assembly to open the region in the sealing wall.

In another arrangement, the reconstituted freeze-dried plasma is administered directly from the container to a recipient.

According to another aspect of the invention, a freeze-dried material comprising freeze-dried human plasma is prepared and stored, transported, reconstituted, and administered using a container as just generally described in any of the foregoing paragraphs. In one arrangement, liquid human plasma is loaded in molds. The molds are cooled until they reach approximately −45° C. The plasma is dried so the moisture content is below 5% w/w, thereby forming the freeze-dried human material that can be stored, transported, reconstituted, and administered using a container. In another arrangement, liquid human plasma is freeze-dried in situ within the container.

According to another aspect of the invention, a freeze-dried material, e.g., freeze-dried human plasma, is stored in a first container, and a reconstituting liquid for the freeze-dried material, e.g., de-gassed water is stored in a separate second container. A transfer set can be manipulated to couple the two containers together, to establish fluid flow communication between the first and second containers. This allows the freeze dried material to be reconstituted within one of the containers. The reconstituted freeze-dried material can also be administered directly from the same container to a recipient.

According to another aspect of the invention, a system is provided that comprises a vessel including first and second end components each comprising a rigid or semi-rigid material defining, respectively, first and second frames providing structural strength. A transparent gas impermeable material peripherally is sealed to the first frame, and a gas permeable material is peripherally sealed to the second frame. A flexible side wall component is peripherally sealed to side edges of the first and second frames. The first end component, the second end component, and the side wall component peripherally define an interior space. At least one port component on the side wall provides fluid communication with the interior space.

The system makes it possible for a material such as fresh human plasma to be freeze-dried, transported, stored, reconstituted, and administered in a single, multifunctional vessel.

Another aspect of the invention provides a method that makes use of the technical features of the multifunctional vessel just described. The method includes introducing a liquid material, such as fresh human plasma, through a first port component on the vessel. The method includes freeze-drying the liquid material in situ within the interior space of the vessel, during which time the gas permeable material of the second end component provides gas transport to accommodate sublimation of water vapor. The method also includes introducing a reconstituting liquid for mixing with the freeze-dried material within the interior space through a second port component of the vessel, to reconstitute the freeze-dried material. The method further includes conveying the reconstituted freeze-dried material from the interior space through a third port component of the vessel.

As defined, the single, multifunctional vessel accommodates freeze-drying a material within the vessel; the transport and storage of the freeze-dried material within the vessel; and the reconstitution and administration of the material from the vessel.

In one embodiment, the method further includes, after freeze drying, introducing an oxygen-free inert gas into the interior space through the gas permeable material of the second end component. The oxygen-free inert gas occupies the interior space with the freeze-dried material to prevent deterioration of the material. The method also includes covering the gas permeable material of the second end component, to trap the oxygen-free inert gas within the interior space with the freeze-dried material. The method includes storing the freeze-dried material in the entrapped oxygen-free inert gas within the vessel for a storage period prior to introduction of the reconstituting liquid.

In one embodiment, the method further includes placing the covered vessel within an outer container during storage.

In another embodiment, there is an assembly for freeze-drying plasma, whereby the container that holds the liquid plasma is separate from the container or structure having the permeable membrane used for removal of vapor during the freeze-drying process. The two containers will be connected by a tubing that will allow vapors to pass from one of the containers to the other. The tubing will be pinched shut or clamped before being removed from the freeze-dryer to isolate the plasma containing container. After removal from the freeze-dryer, the first container can be sealed and severed from the tubing and second container.

These and other areas of importance and significance will become apparent from following description.

BRIEF DESCRIPTION OF THE DRAWINGS

FIG. 5A is a side elevation section view of the interior sealing wall and associated valve assembly formed within the device taken generally along line 5A-5A in FIG. 1, prior to the removal of the outer protective skirt.

FIG. 5B is a side elevation section view like that shown in FIG. 5A, showing an alternative arrangement of the interior sealing wall and multiple valve assemblies.

FIG. 6 is a side elevation section view of the interior sealing wall and associated valve assembly formed within the device taken generally along line 6-6 in FIG. 4A, after the removal of the outer protective skirt and prior to manipulating the device to reconstitute the freeze-dried materials.

FIG. 7 is a side elevation section view of the interior sealing wall and associated valve assembly like that shown in FIG. 6, after opening at least one region of interior sealing wall and prior to manipulating the device to reconstitute the freeze-dried materials.

FIGS. 10 to 15 are front elevation view of the device shown in FIG. 9, showing the manipulating the device to reconstitute the freeze-dried materials.

FIG. 16 is a front elevation view of the device shown in FIG. 15, showing the administration of reconstituted material directly from the device to a recipient.

FIGS. 17A to 17E are diagrammatic perspective views to an illustrative process for the preparation of a freeze-dried plasma cake from liquid human plasma, prior to insertion and storage within the device shown in FIG. 1.

FIGS. 18 and 19 are front elevation views of placing a freeze-dried material (like the plasma cake formed using the process FIGS. 17A to 17E) in the first chamber of the device shown in FIG. 1.

FIG. 30 is a front elevation view of a system for storing freeze-dried material, e.g., freeze-dried human plasma, and a reconstituting liquid for the freeze-dried material, comprising individual first and second containers and a transfer set that makes possible a reconstitution of the freeze-dried material within the system for administration to a recipient.

FIG. 31 is a front elevation view of the system shown in FIG. 30, with the first and second containers joined in fluid communication by the transfer set to reconstitute the freeze-dried material.

FIGS. 46 and 47 are perspective views of another representative embodiment of a unitary freeze-died material storage assembly comprising a vessel as shown in FIGS. 39A to 39D and an integral closure cover, FIG. 46 showing the closure cover in an opened condition, and FIG. 47 showing the closure cover in a closed condition.

FIGS. 48 and 49 are perspective views of the unitary freeze-dried material storage assembly shown in FIG. 47 (with the closure cover in the closed condition) placed within a rigid outer container with a lid for enclosing the unitary freeze-dried material storage assembly during transport and storage until the instance of use.

FIGS. 50 and 51 are perspective views showing the transfer of a unit of liquid plasma into a unitary freeze-dried material storage assembly of the type shown in FIG. 42, with the closure cover in the opened condition, which begins the process using the unitary freeze dried material storage assembly.

FIG. 57 shows the reconstitution of the freeze-dried plasma material within a unitary freeze-dried material storage assembly after under the freeze-drying and packaging process shown in FIGS. 50 to 56, by transferring a reconstituting liquid from a source container into the unitary freeze-dried material storage assembly for mixing with the freeze-dried plasma material.

FIG. 58 shows the administration of reconstituted freeze-dried plasma material from a unitary freeze-dried material storage assembly into an individual.

FIG. 61 is a front elevation view depicting an alternate system and device for freeze-drying material, e.g. plasma, with the system comprising a first collapsible container that acts as a primary storage portion and a secondary lyophilizing portion, with the two portions forming a single device or assembly, connected by a tubing.

FIG. 62 is a front elevation view depicting the system and device depicted in FIG. 61, with a pH adjustment solution being aseptically added to the first container.

FIG. 63 is a front elevation view further depicting the system and device of FIG. 61, with liquid plasma being introduced into the first container.

FIGS. 66A-68B provide various depictions of instruments, such as closure devices, used for closing or pinching shut a tubing that connects the secondary lyophilizing portion to the primary storage portion to form the final bag shown in FIG. 66, using the lyophilizers to close and pinch shut the tubing prior to being removed from the freeze-dryer.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

I. Device for Storing and Reconstituting Freeze-Dried Plasma

Figure 1:
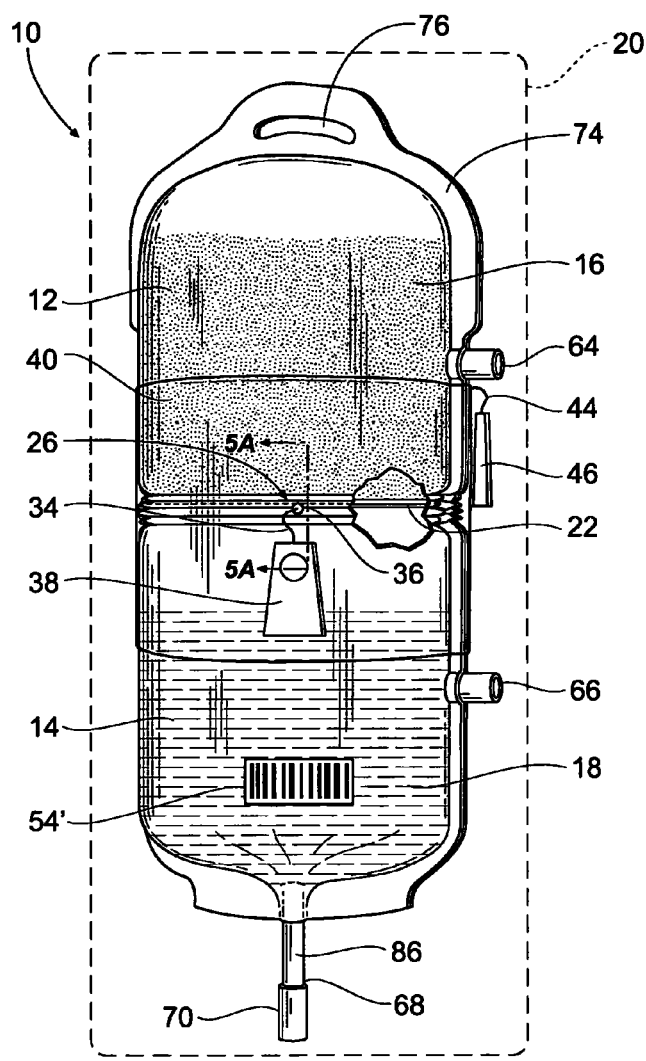
FIG. 1 is a front elevation view of a device for storing freeze-dried material, e.g., freeze-dried human plasma, and a reconstituting liquid for the freeze-dried material, making possible a reconstitution of the freeze-dried material within the device and an administration of the reconstituted freeze-dried material directly from the device to a recipient, the device being shown prior to the removal of an outer protective skirt.
Figure 2:
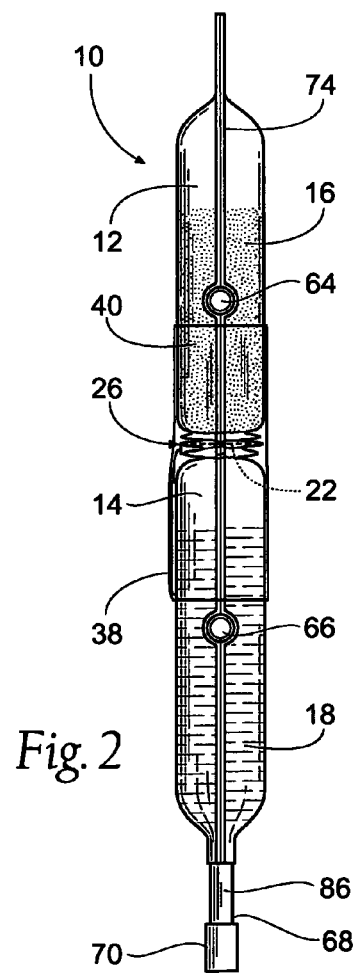
FIG. 2 is side elevation view of the device shown in FIG. 1.

FIGS. 1 and 2 show a device 10 for storing and administering a freeze-dried material. The device 10 comprises a flexible bag having a first collapsible chamber 12 and a second collapsible chamber 14.

The first chamber 12, also referred to as the dry chamber, contains an aliquot of a freeze-dried material 16. The nature and type of freeze-dried material 16 can vary. In the illustrated embodiment, the freeze-dried material comprises human plasma, and the aliquot is a single donor unit of human plasma.

The second chamber 14, also referred to as the wet chamber, contains a reconstituting liquid 18 for the freeze-dried material 16. The nature and type of the reconstituting material 18 can vary. In the illustrated embodiment, the reconstituting material 18 comprises sterile water, which may be degassed, if desired. In use, the sterile water in the wet chamber 14 is mixed with the freeze-dried plasma in the dry chamber 12 to provide plasma for transfusion. The plasma is reconstituted and administered on site using the device 10.

The first chamber 12 is sized and configured to maintain the freeze-dried material 16, prior to its reconstitution, in a vacuum packed, aseptic, moisture-free and low concentration oxygen environment, preferably accommodating long term storage, e.g., at least 2 years at room temperature. Stored in this environment, the freeze-dried material 16 retains its desired qualities for transfusion.

The second chamber 12 is sized and configured to maintain the reconstituting liquid 18, prior to its mixing with the freeze-dried material 16, in an aseptic environment and at a low gas concentration, preferably accommodating long term storage, e.g., at least 2 years at room temperature.

The volume of each of the chambers 12 and 14 is preferably approximately 50% larger than the volume of the freeze-dried material 16 in the first chamber 12. This provides ample volume within the device 10 for mixing the freeze-dried material 16 and reconstituting liquid 18, either in the first chamber 12 or the second chamber 14, as will be described in greater detail later.

The device 10 may be made, e.g., of an inert medical grade plastic material, such as polyvinyl chloride, polyethylene, polypropylene, or high density polyethylene. The device 10 can comprise a multi-laminate of polymer layers for greater durability, e.g., to resist tearing and puncturing that could be encountered in normal handling.

The material of the device 10 can be selected to be transparent, if desired, to allow visual inspection of the contents of the chamber 12 and 14. The material in the first chamber 12 can be selected to provide a gas-impermeable barrier, such as a metallized, reduced gas-permeability coating, or a metal laminate. In this case, the wall of the first chamber may be opaque.

Furthermore, the device 10 may be enveloped prior to use by a vacuum sealed over-wrap 20 (shown in phantom lines in FIG. 1), made, e.g., a metallized, gas impermeable material. The over-wrap 20 enhances shelf-stability.

An interior sealing wall 22 (see FIG. 1) compartmentalizes the device 10 into the first and second chambers 12 and 14 (see also FIG. 5A). The sealing wall 22 provides a barrier between the first chamber 12 and the second chamber 14, which normally prevents contact between the freeze-dried material 16 and the reconstituting liquid 18 during storage, up to the instant of use.

As FIGS. 5A/B and 7 show, one or more regions 24 of the sealing wall 22 may be selectively opened by a caregiver, as will be described in greater detail later. The region(s) 24, when opened, make possible fluid communication between the two chambers 12 and 14. The fluid communication makes it possible to mix the reconstituting liquid 18 with the freeze-dried material 16, as will further be described in greater detail later.

The region(s) 24 of the sealing wall 22 may be opened in various ways. In a representative embodiment (see FIG. 5), the sealing wall 22 includes a normally closed valve assembly 26 associated with each region 24 where the sealing wall 22 is to be opened. In FIG. 5A, a single region 24 is shown, so a single valve assembly 26 is shown. As shown in FIG. 5B, where multiple regions 24a and 24b are provided, each region 24a and 24b would include its own dedicated valve assembly 26a and 26b, respectively.

In the representative embodiment (see FIGS. 5A and 5B), each valve assembly 26 includes a primary, pressure sensitive valve 28. The valve 28 can take the form, e.g., of a short duck bill or two way flap valve. The primary valve 28 is sized and configured to normally resist flow communication between the two chambers 12 and 14.

In the representative embodiment, each valve assembly 26 also includes a normally closed septum 30 between the valve 28 and the wet chamber 14. The septum 30 maintains closure between the two chambers 12 and 14, independent of the valve 28. Independent of the valve 28, the septum 30 prevents unintended passage of material between the two chambers 12 and 14, thereby maintaining the separate integrity of the freeze-dried material 16 and the reconstituting liquid 18 within the device 10 prior to use.

The septum 30 includes an integrated tear member 32 that is incorporated within the septum 30. The integrated tear member 32 is coupled to a pull string 34 that extends through a fluid sealed pass-through or septum 36 in the wall of the second chamber 14. As FIG. 1 shows, the pull string terminates outside the device 10 at a pull tab 38.

As FIGS. 6 and 7 show, the tear member 32 is sized and configured to open the septum 30 when a caregiver pulls on the tab 38. The pass-through or septum 26 seals around the pull string 34, and also seals close after passage of the pull string 34 from the interior of the chamber 14, maintaining in integrity of the second chamber 14. Opening the septum 30 in this manner forms the open region 24 (see FIG. 7). The open region 24 places the first and second chambers 12 and 14 into communication through the valve 28.

With the region 24 opened (see FIG. 7), the primary valve 28 still serves to normally resist flow communication between the two chambers 12 and 14. However, when the region 24 is opened, the valve 28 is sized and configured to resiliently yield in response to a difference in fluid pressure between opposite sides of the valve 38 (see FIGS. 11 and 14). In response to the pressure differential, the valve 28 opens in the direction of the fluid pressure differential, from the region of higher pressure toward the region of lower pressure.

As will be described in greater detail later (as shown, respectively, in FIGS. 10 and 13), the caregiver creates the fluid pressure differential across the valve 28 by selectively squeezing one chamber and not the other chamber. Fluid is expelled in response to the fluid pressure differential through the valve 28 from the chamber that is squeezed into the chamber that is not squeezed.

The multi-component valve assembly 26 provides a redundant sealing capability, to assure that the chambers 12 and 14 remain separated until it is desired to reconstitute the freeze-dried material 16.

In a representative embodiment (see FIGS. 1 and 2), the device 10 further includes an outer tear-away skirt 40, which provide further redundancy. As FIGS. 1 and 2 show, the skirt 40 overlays the device 10 in the region of the sealing wall 22. The skirt 40 serves to overlay and protect the components of the valve assembly 26 associated with the sealing wall 22.

At least one region of the skirt 40 is circumferentially attached about an exterior wall of the device, e.g., by adhesive, either in the region of the first chamber, the second chamber, or both. Furthermore, as the skirt 40 is installed about the device 10, the exterior wall of the device is desirably plicated or pleated or otherwise bunched together (as FIGS. 1 and 2 show). Alternatively, the placations can be performed in the wall of the container.

The placations relieve wall stress in the region of the sealing wall 22. The skirt 40, once attached, maintains these placations or pleats, and thereby serves to relieve or distribute wall stresses in the region of sealing wall 22 and the components of the valve assembly 26 associated with the sealing wall 22. Such wall stresses can arise, e.g., due to the weight of the reconstituting liquid 18 contained in the second chamber 14, and/or by virtue of handling during transport and manipulation prior to use. The presence of the overlaying skirt 40 also serves to isolate the components of the valve assembly 26 associated with the sealing wall 22 from unintended contact during transport and prior to use.

Figures 3, 4A, 4B:
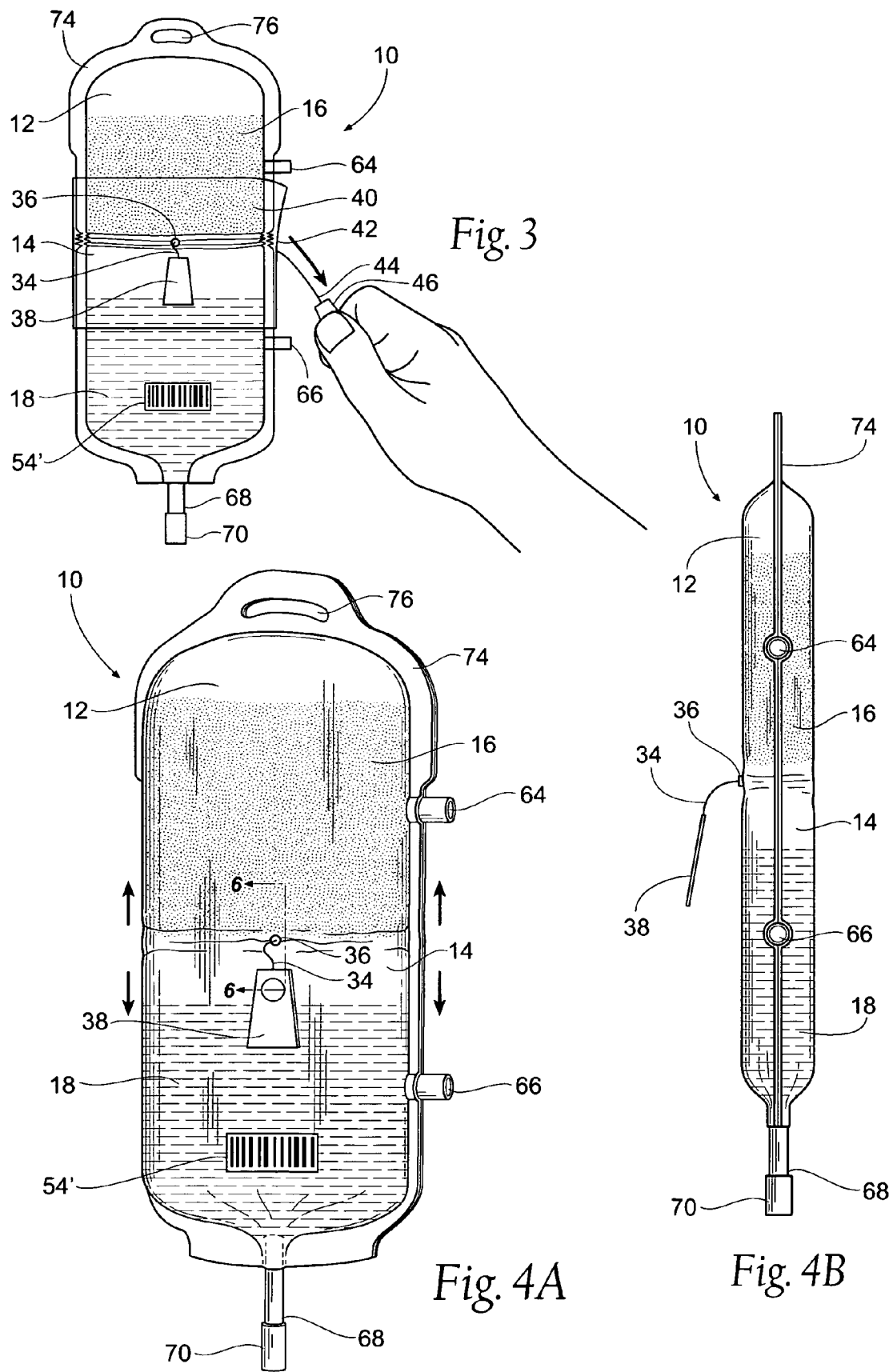
FIG. 3 is a front elevation view of the device shown in FIG. 1, showing the tearing of the outer protective skirt for its removal prior to manipulating the device to reconstitute the freeze-dried materials.
FIG. 4A is a front elevation view of the device shown in FIG. 3, after the removal of the outer protective skirt and prior to manipulating the device to reconstitute the freeze-dried materials.
FIG. 4B is side elevation view of the device shown in FIG. 4A.

As FIG. 1 shows, the skirt 40 includes an integrated tear member 42. The integrated tear member 42 includes a pull string 44 that terminates with a pull tab 46, that depends outside the skirt 40. The tear member 42 is sized and configured to tear open the skirt 40 when a caregiver pulls on the tab 46 (as FIG. 3 shows). Upon removal of the skirt 40, the placations of the walls of the bags 12 and 14 are relieved (as FIGS. 4A and 4B show), placing the components of the valve assembly 26 associated with the sealing wall 22 into condition for manipulation.

It should be understood that reference to the first chamber 12 and the second chamber 14 is done to distinguish one chamber from the other, and not to limit either chamber to a specific spatial relationship. For example, the chambers 12 and 14 may be arranged face to face, having vertical edges in contact.

The technical features of the device 10 includes separate chambers or compartments that are separated by sealing means that will allow for eventual interconnection and intercommunication, between the chambers, which can be accomplished in various ways. Furthermore, reference to a bag or chambers should not be limited to any specific structure or shape but should be understood to refer any container capable of carrying and mixing the contents 16 and 18.

II. Preparing and Packaging the Freeze Dried Material and Reconstituting Liquid

Preparing and packaging the freeze-dried material 16 and reconstituting liquid 18 comprises two main processing steps: (i) freeze-drying the material 16, and (ii) packaging the material 16 and the reconstituting liquid 18 within the chambers 12 and 14.

A. Preparation of Freeze-Dried Plasma

In a representative embodiment, the freeze-dried material 16 comprises plasma. A description of an illustrative way of preparing freeze-dried plasma for packaging in the device 10 therefore follows.

Preparation and manufacturing of the plasma will take place in an aseptic setting. Preferably, manufacturing and preparation procedures can be done, for example, in an ISO Class 5 clean room (or better) with ISO Class 3 bio-containment hoods for aseptic handling of human plasma. Freeze drying can be done aseptically in a CIP/SIP freeze dryer.

Human plasma is collected from a single donor in a conventional way, e.g., by collecting a unit of whole blood from the donor in a closed system collection bag, followed by centrifugal separation of the plasma and its collection in an integrally connected transfer bag (containing one plasma unit of about 250 ml). Each unit (contained in the transfer bag) will be handled individually in the bio-containment hood. Between handling one single donor unit and another unit single donor unit from a different donor, there may be a line clearance protocol for change-over in the bio-containment hood, or a validation process for flow design and change-over can be otherwise provided. This protocol may address removal of all tools and materials associated with the previous handling. It may also address the thorough wash down of the containment work area and work area instruments (mass balances) to ensure no residues of the previous handling were left in place. The identification of single donor samples will be maintained by bar coding and other tagging of the single donor human plasma containers.

As shown in FIG. 17A, prior to freeze drying, the 250 ml human plasma unit is dispensed from the transfer bag 48 into a sterile, pyrogen free, rectangular mold 50 (e.g., 4 cm×10 cm×12.5 cm–d×w×l). The mold 50 can be stainless-steel; however it can also be composed of metal with good thermal transfer properties such as aluminum, aluminum alloy, titanium or gold. The mold 50 may be coated on its inside surfaces with a tough, inert barrier film with good release properties such as PTFE or diamond.

As shown in FIG. 17B, the mold 50 containing the human plasma is then placed inside a water-impermeable, vapor-permeable, sterile, heat sealable bag 52 with bar coding and tagging 54 indicative of the human plasma identification (source, blood type, date of collection, etc.). This vapor permeable bag 52 would typically be manufactured using microporous PTFE membrane material (e.g. Gore-Tex™) or microporous HDPE membranes (e.g. Tyvek™).

The bag 52 is heat sealed to contain the mold 50 and human plasma. The bag 52 is designed to neatly contain the mold 50 and its contents without any bunching or sagging of the bag material below the surface of the interior mold wall edge or at the base of the mold.

As shown in FIG. 17C, the mold 50 inside the containment bag 52 is then placed inside a freeze dryer 56 on an aseptic freeze dryer shelf surface 58. The freeze dryer 56 used for the lyophilization will be a validated clean in place, steam in place freeze dryer with shelf area of near 200 square feet or more. Such a freeze dryer 56 can accommodate at least 500 molds when it is fully loaded.

Once loaded, the freeze dryer cycle is started. This cycle generally cools the human plasma to near −45° C. and freezing for a prescribed period, e.g., 2 to 8 hours, followed by cooling of the freeze dryer condenser and application of vacuum to start the freeze drying cycle. A freeze-dried human plasma cake 60 is formed.

In a representative primary freeze drying cycle, the temperature of the human plasma cake 60 needs to remain below its collapse temperature (e.g., −33° C.) to maintain its integrity. When the moisture content of the cake 60 is below 5% weight per weight (w/w), a secondary drying cycle (the elevated temperature) may be used to further lower the moisture content, if desired. The combined primary and secondary freeze drying cycles may take 72 hours or more, but such times will vary with the processing conditions. At the conclusion of the freeze drying cycle, the freeze dryer vacuum may be opened to an atmosphere of an oxygen-free, high purity inert gas such as nitrogen or argon.

Figure 17D:
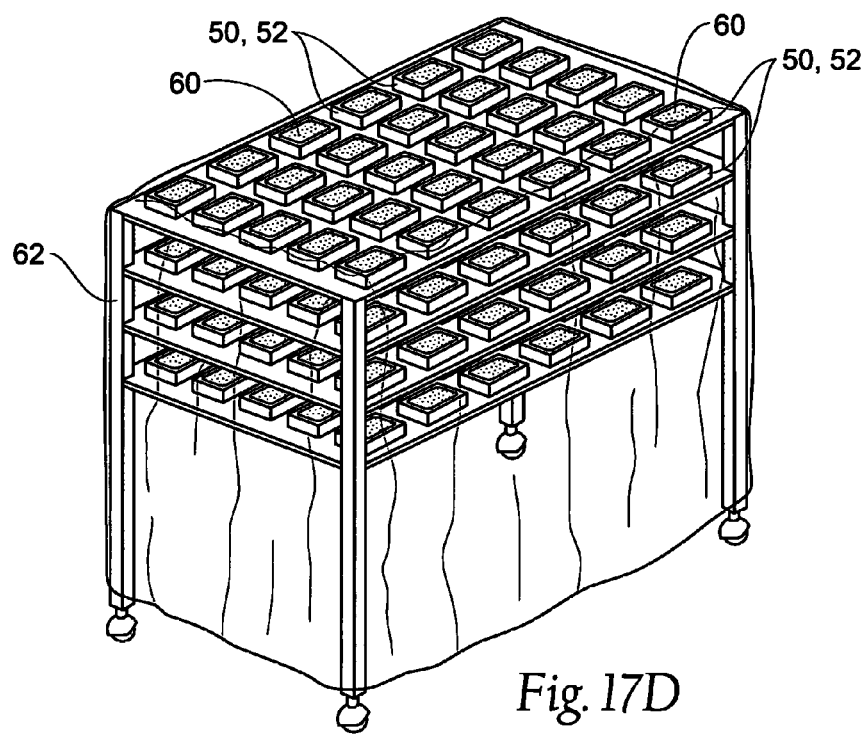

As shown in FIG. 17D, the freeze dried cakes 60 in their molds 50 and containment bags 52 are removed to an aseptic containment cart 62 whose environment may be maintained under a nitrogen or argon blanket to exclude moisture and oxygen. The containment cart 62 may couple to the front of the freeze dryer to allow for transfer of the freeze dryer contents under a controlled inert gas blanket.

The containment carts 62 may be used to store human freeze dried plasma cakes (each cake within a mold 50 and enclosed within a bag 52) as well as allow cakes to be transferred to a device loading area, which allows loading of the freeze dried plasma cake 60 into the device 10, as will be described in greater detail later.

B. Packaging Freeze-Dried Plasma and Water into the Device

As shown in FIG. 1, the device 10 comprises a first aseptic vacuum port 64, which communicates with the first chamber 12, and a second aseptic vacuum port 66, which communicates with the second chamber 14. The vacuum ports 64 and 66 are sized and configured for connection to various tubing T during final assembly (see FIGS. 18 to 21) to facilitate packaging of the freeze-dried plasma material 16 and reconstituting liquid 18 (e.g., water) within the device 10.

An administration port 68 is also heat sealed in communication with the second chamber 14. The administration port 68 is used during the packaging process to convey the reconstituting liquid 18 into the second chamber 14, as will be described in greater detail later. After the reconstituting liquid 18 is packaged within the chamber 14, the administration port 68 is sealed with a conventional septum or frangible membrane assembly or a convention screw-lock leur fitting 70, to accommodate its coupling to an administration set 72 to the port 28 at time of transfusion, as shown in FIG. 16.

The device 10 also comprises a heat sealable aseptic flange 74 (see FIG. 1), which allows a freeze-dried plasma cake 60 to be inserted into the first chamber 12, as shown in FIG. 18, and then sealed in an aseptic fashion, as shown in FIG. 19.

A slot 76 may be pre-formed on the flange 74. The slot 76 makes it possible to hang the device 10 at a desired gravity head height for administering reconstituted plasma to an individual, as FIG. 16 shows.

Individual single donor human plasma freeze dried cakes 60 are aseptically loaded into the device 10 (see FIG. 18) through the flange 74. The device loading area may be, e.g., a bio-containment hood that excludes significant oxygen and moisture contamination by inert gas blanketing. Also the device loading area may be an aseptic glove-box system with an inert gas environment.

Figure 17E:
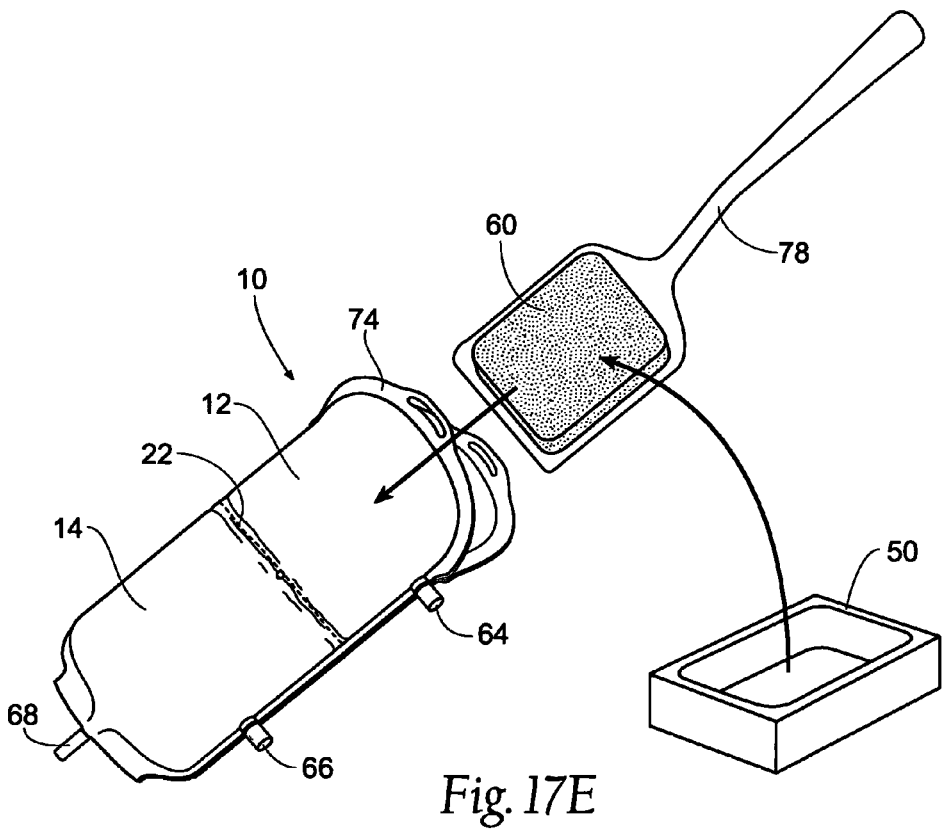

FIGS. 18 and 19 depict a representative loading process. The bag 52 is opened, and the plasma cake 60 removed from the mold 50. The plasma cake 60 is loaded through the open flange 74 into the first chamber 12. As shown in FIG. 17E, it is anticipated that the plasma cake 60 can be transferred into the chamber 12 directly from the mold 50 (after removal of the bag 52) using a single-use, aseptic, clear-plastic applicator tool 78, similar to a large open-ended spatula. Once the chamber 12 is loaded, the flange 74 can be sealed closed using various conventional aseptic techniques, e.g., dielectric welding or heat sealing.

The loading of the plasma chamber 12 can be through an "oyster style" opening that comprises approximately 50% of the flange 74 of the chamber 12, which can be readily sealed close after loading. An oyster opening would allow loading of the plasma cake 60 without concerns of damaging the first chamber 12 or the freeze-dried plasma during the process. In the case of the oyster opening, there would be sufficient excess overlay of the edge seam to allow for straightforward edge-seam alignment and contact during the sealing process.

Preferably, after loading and sealing of the chamber 12, an aseptic vacuum is applied through tubing T connected to the vacuum port 64 on the first chamber 12 (see FIG. 19). Upon achieving near 100 mTorr of pressure, the vacuum port 64 is heat sealed and the tubing T removed. This evacuation process provides for the eventual ability to mix and reconstitute the human freeze dried plasma without introduction of bubbles and without foaming. The vacuum would also cause the plasma cake 60 to be compacted to a fine powder, forming the freeze-dried material 16 within the chamber 12.

To maintain a direct traceable link between the source plasma and the material 16 packaged into the chamber 12, the device 10 preferably includes a bar coding and tagging 54' (see FIG. 1), which is indicative of the human plasma identification (source, blood type, date of collection, etc.), and which replicates or is otherwise linked to the bar coding and tagging 54 placed on the bag 52 enveloping the mold 50 at the time of freeze-drying. In this way, the device 10 maintains a traceable link back to the human donor source.

To assist in the reconstitution of the freeze dried plasma material 16, an aseptic dense sphere of an inert material such as, but not limited to, glass, polyvinyl chloride or high density polyethylene may be added to the inside of the chamber 12 prior to its closure.

Figure 20:
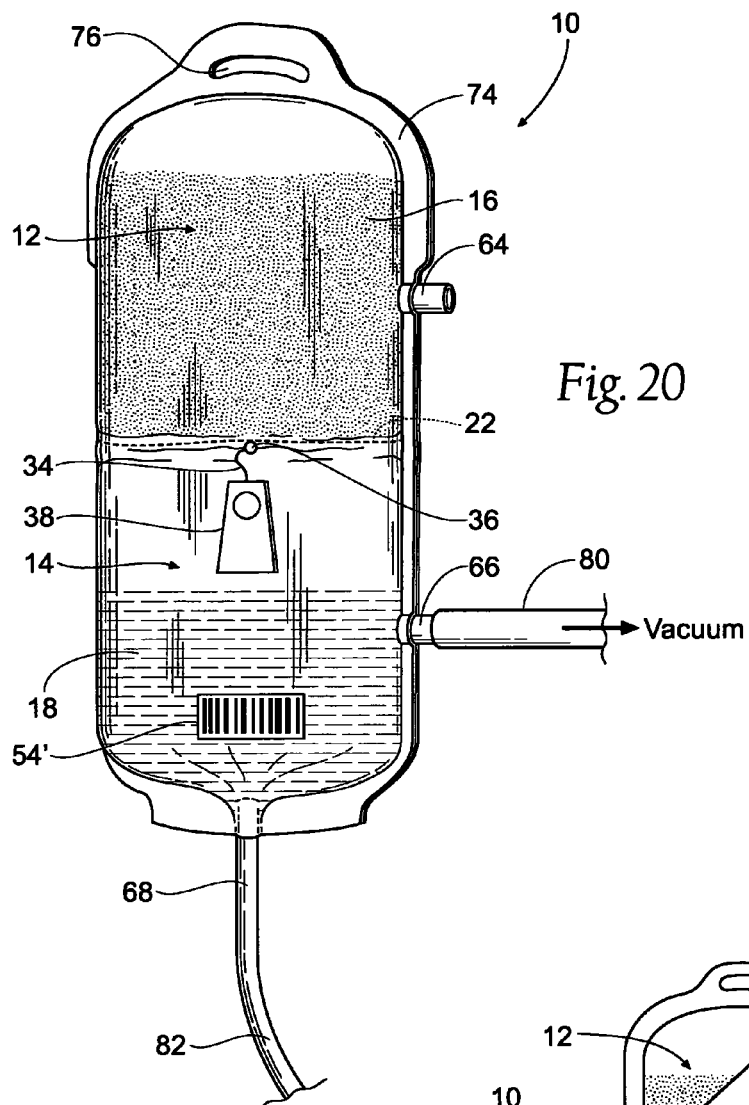
FIG. 20 is a front elevation view of placing a reconstituting liquid for the freeze-dried material in the second chamber of the device shown in FIG. 1.

The reconstituting liquid 18 (in the representative embodiment, gas-free water) is introduced into the second chamber 14. The vacuum port 66 and administration port 68 are connected to feed lines 80 and 82, respectively, as FIG. 20 shows. Gas in the chamber 14 is removed by application of aseptic vacuum.

The vacuum port 66 is sealed and the tubing 80 is removed. The required aliquot (e.g., approximately 250 ml) of reconstitution fluid is added to the chamber 14 through the administration port 68. The tubing 82 is removed and the administration port 68 is then sealed with the conventional septum or frangible membrane assembly or a convention screw-lock leur fitting 70, which accommodate coupling of the administration set 68 to the port 68 at time of transfusion.

To assist in the reconstitution of the freeze dried plasma, an aseptic dense sphere of an inert material such as, but not limited to, glass, polyvinyl chloride or high density polyethylene may be present inside the second chamber 14.

Figure 21:
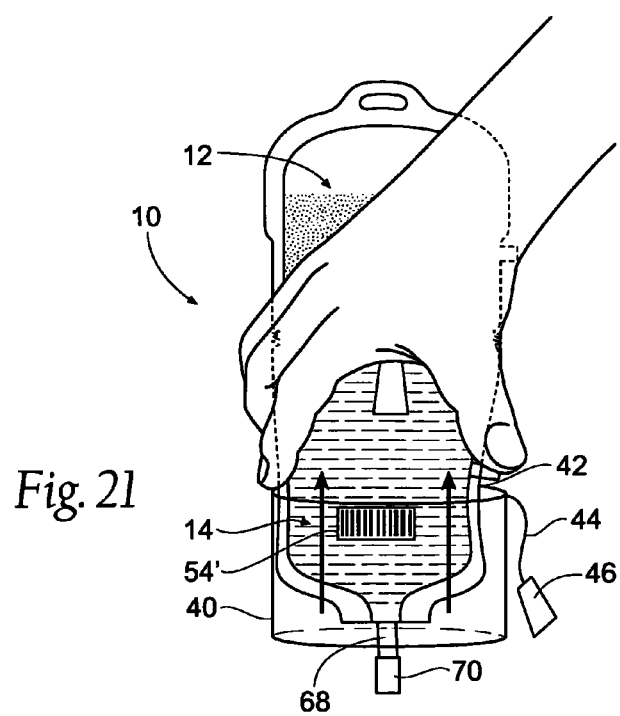
FIG. 21 is a front elevation view of placing the outer protective sleeve about the device, to create the device shown in FIG. 1.

As FIG. 21 shows, after packaging the freeze-dried material 16 and the reconstituting liquid 18 in the manner just described, the wall of the device 10 is plicated in the region of the sealing wall 22, as previously described, and the outer skirt 40 attached. The overwrap 418 20 can be applied, as shown in FIG. 1, if desired.

The device 10 is ready for storage, transport, and use

III. Reconstitution and Administration of the Freeze-Dried Material

The device 10 makes possible a purposeful two step manipulation in anticipation of reconstituting the freeze-dried material 16.

Figure 8:
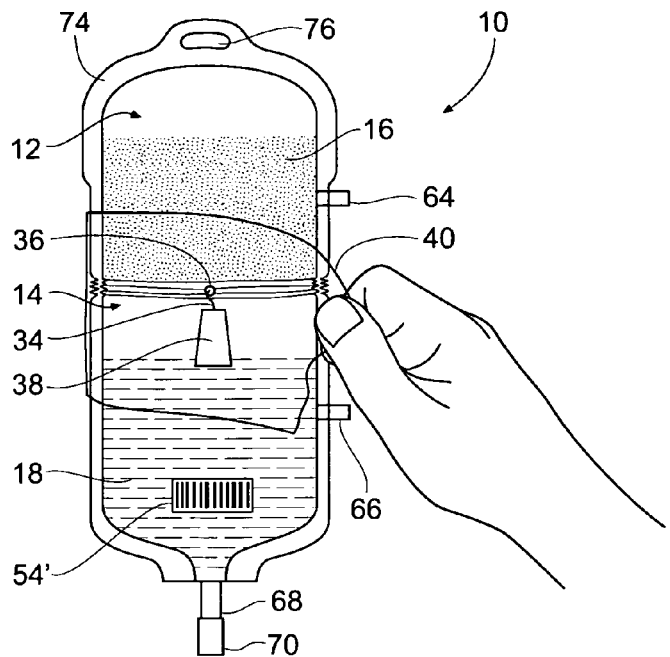
FIG. 8 is a front elevation view of the device shown in FIG. 1, showing the removal of the outer protective skirt prior to manipulating the device to reconstitute the freeze-dried materials.
Figure 9:
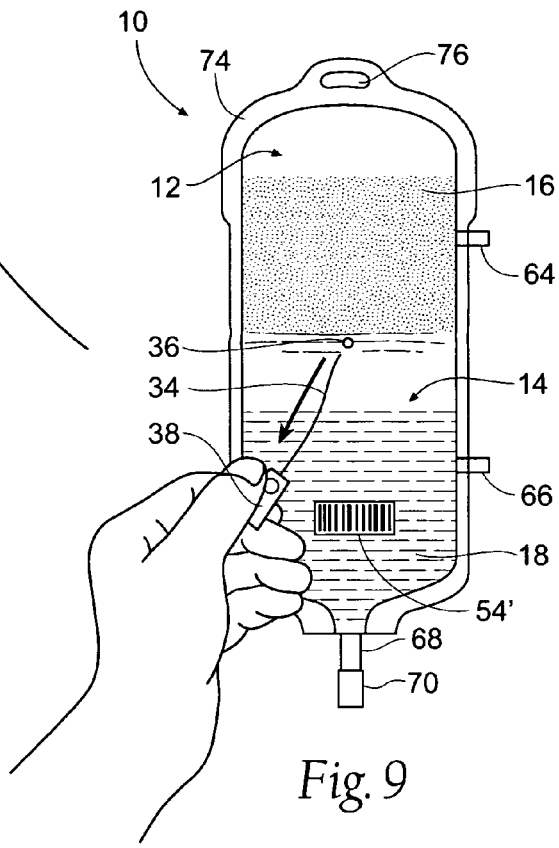
FIG. 9 is a front elevation view of the device shown in FIG. 8, showing the manipulation of the valve assembly to open at least one region of the interior sealing wall, in the manner also shown in FIG. 7.

In the first step (shown in FIG. 8), the tear member 42 is pulled to open and remove the skirt 40, which places the sealing wall 22 of the device 10 in the ready for use configuration shown in FIG. 6. In the second step (shown in FIG. 9), the tear member 32 is pulled to open the septum 20 (which FIG. 7 shows in greater detail). The region 24 of the sealing wall 22 is thereby opened.

Figure 10:
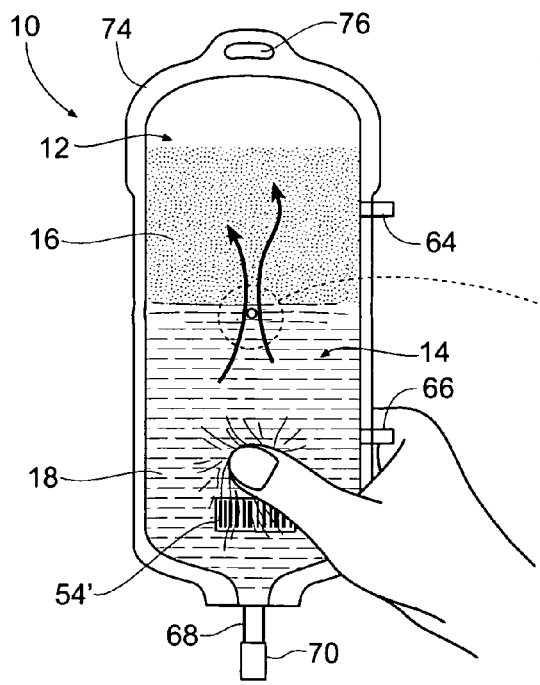
Figure 11:
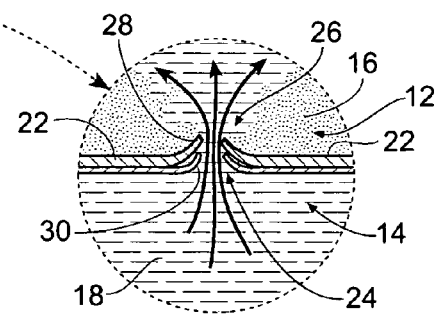

When the region 24 is opened, the caregiver can apply pressure to the second chamber 14 to express the reconstituting liquid 18 from the second chamber 14 into the first chamber 12 (see FIGS. 10 and 11), thereby beginning the reconstitution of the freeze-dried material 16. More particularly, with the region 24 opened, the caregiver can apply pressure to the second chamber 14 (as FIG. 10 shows) and not the first chamber 12. As FIGS. 10 and 11 show, the pressure differential between the second chamber 14 and the first chamber 12 expels the liquid 18 from the second chamber 14, through the valve 28 (which yields in response to the pressure differential to open in the direction of the first chamber 12, as FIG. 11 shows), and into the first chamber 12. The expelled liquid 18 mixes with the freeze-dried material 16 in the first chamber 12, beginning the reconstitution.

As FIG. 12 show, shaking the device 10 accelerates the mixing of liquid 18 and freeze-dried material 18 in the first chamber 12.

When the region 24 is opened, the caregiver can subsequently apply pressure to the first chamber 12 to express the material 16, now at least partially reconstituted in the liquid 18, from the first chamber 12 into the second chamber 14 (see FIGS. 13 and 14). Reconstitution of the freeze-dried material 16 is advanced. More particularly, as FIG. 13 shows, the caregiver can now apply pressure to the first chamber 12 (as FIG. 13 shows) and not the second chamber 14. As FIGS. 13 and 14 show, the pressure differential between the first chamber 12 and the second chamber 14 expels the mixture of the liquid 18 and the freeze-dried material 16 from the first chamber 12, through the valve 28 (which yields in response to the pressure differential to open in the direction of the second chamber 14, as FIG. 14 shows), and back into the second chamber 14. The expelled liquid 18 continues to mix with the freeze-dried plasma material 18, furthering the reconstitution of the material 18.

As FIG. 15 shows, shaking the device 10 further accelerates the mixing of water and freeze-dried plasma in the second chamber 14.

The material 16 reconstituted in the liquid 18 can be passed back and forth between the two chambers 12 and 14 by alternating pressure on the chambers 12 and 14, with intermediate shaking, until the desired degree of mixing occurs, at which time the mixture is ready for transfusion. More particularly, the caregiver can proceed to squeeze one chamber and not the other, to expel the mixture of the liquid 18 and freeze-dried material 18 back and forth between the chambers 12 and 14, with periodic shaking, until the desired degree of mixing and reconstitution of the plasma is accomplished.

At this point (as FIG. 16 shows), the caregiver can couple the administration fitting 70 of the device 10 to the fluid administration set 72. The reconstituted plasma is transfused by gravity flow through a phlebotomy needle 84 into the circulatory system of an individual.

The administration fitting 70 can further include a static mixing tube 86 (as shown in FIG. 16), to assist in continued reconstitution of plasma aliquot 5 with water 7 during transfusion.

The device 10 as described provides:

i) long term stable containment of a freeze-dried material such as freeze-dried human plasma;

ii) eventual rapid reconstitution of the freeze-dried material with a reconstituting liquid for injection; and iii) eventual delivery of the reconstituted freeze dried material to a trauma victim in a safe, aseptic manner.

IV. Other Representative Embodiments

A. Dual Containers With Intermediate Valve Passage

Figure 22:
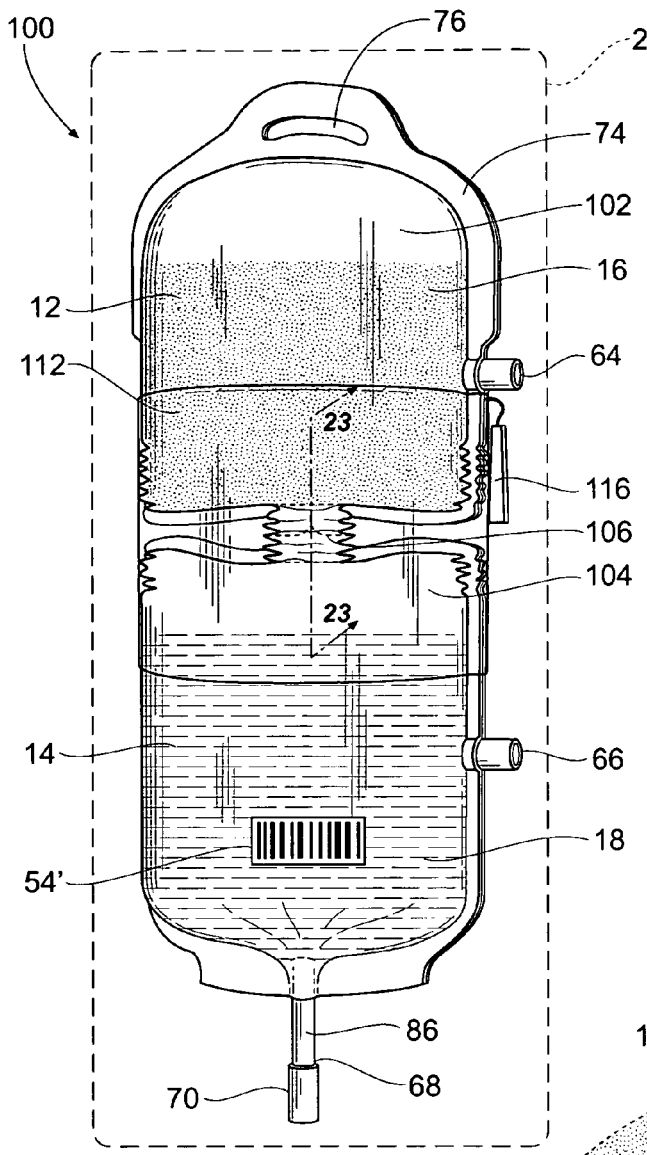
FIG. 22 is a front elevation view of an alternative device for storing freeze-dried material, e.g., freeze-dried human plasma, and a reconstituting liquid for the freeze-dried material, making possible a reconstitution of the freeze-dried material within the device and an administration of the reconstituted freeze-dried material directly from the device to a recipient, the device being shown prior to the removal of an outer protective skirt.

FIG. 22 shows another representative embodiment of a device 100 for storing an administering a freeze-dried material. The device 100 comprises a first collapsible container 102 and a second collapsible container 104, joined by an intermediate normally closed valve assembly 106.

The device 100 shares many of the technical features of the device shown in FIG. 1, albeit the particular structure differs. The first container 102 comprises the dry chamber 12 as previously described, and is sized and configured to contains an aliquot of a freeze-dried material 16, such as a freeze-dried single donor unit of human plasma.

The second container 104 comprises the wet chamber 14, as previously described, and is sized and configured to contain a reconstituting liquid 18 for the freeze-dried material 16. As before described, the reconstituting material 18 can comprise, e.g., sterile water, which may be degassed, if desired.

In use, the sterile water in the wet chamber 14 is mixed with the freeze-dried plasma in the dry chamber 12 to provide plasma for transfusion. The plasma is reconstituted and administered on site using the device 10.

As before described, the first container 102 is sized and configured to maintain the freeze-dried material 16, prior to its reconstitution, in a vacuum packed, aseptic, moisture-free and low concentration oxygen environment, preferably accommodating long term storage, e.g., at least 2 years at room temperature. Stored in this environment, the freeze-dried material 16 retains its desired qualities for transfusion.

As also before described, the second container 104 is sized and configured to maintain the reconstituting liquid 18, prior to its mixing with the freeze-dried material 16, in an aseptic environment and at a low gas concentration, preferably accommodating long term storage, e.g., at least 2 years at room temperature.

The volume of each of the containers 102 and 104 is preferably approximately 50% larger than the volume of the freeze-dried material 16 in the first chamber 12. This provides ample volume within the device 10 for mixing the freeze-dried material 16 and reconstituting liquid 18, either in the first container 102, or the second container 104, as will be described in greater detail later.

The containers 102 and 104 may be made, e.g., of an inert medical grade plastic material, such as polyvinyl chloride, polyethylene, polypropylene, or high density polyethylene. One or both of the container 102 and 104 can comprise a multi-laminate of polymer layers for greater durability, e.g., to resist tearing and puncturing that could be encountered in normal handling.

The material of the containers 102 and 104 can be selected to be transparent, if desired, to allow visual inspection of the contents of the chamber 12 and 14. The material in the first container 102 can be selected to provide a gas-impermeable barrier, such as a metallized, reduced gas-permeability coating, or a metal laminate. In this case, the wall of the first chamber may be opaque.

As before described, the device 100 may be enveloped prior to use by a vacuum sealed over-wrap 20 (shown in phantom lines in FIG. 22), made, e.g., a metallized, gas impermeable material. The over-wrap 20 enhances shelf-stability.

In the alternative representative embodiment shown in FIG. 22, the valve assembly 106 includes a pressure sensitive valve 108 enclosed within a flexible tubular valve passage 110, which extends between the two containers 102 and 104. The valve 108 can take the form, e.g., of a short duck bill or two way flap valve. The valve 108 is sized and configured to normally resist flow communication between the two containers 102 and 104. However, the valve 108 is sized and configured to resiliently yield in response to a difference in fluid pressure between opposite sides of the valve 108 (in the same manner as the valve 28 shown in FIGS. 11 and 14). In response to the pressure differential, the valve 108, like the valve 28, opens in the direction of the fluid pressure differential, from the region of higher pressure toward the region of lower pressure.

The regions of the wall of the containers to which the valve passage 110 is joined normally close communication between the containers 102 and 104 through the valve passage 110.

An outer tear-away skirt 112 is wrapped around the mid-regions of the containers 102 and 104 and the intermediate valve passage 110. The skirt 112 serves to overlay and protect the components of the valve assembly 106 prior to use. At least one region of the skirt 112 is circumferentially attached about an exterior wall of each container 102 and 104, e.g., by adhesive, either in the region of the first chamber, the second chamber, or both.

Figure 23:
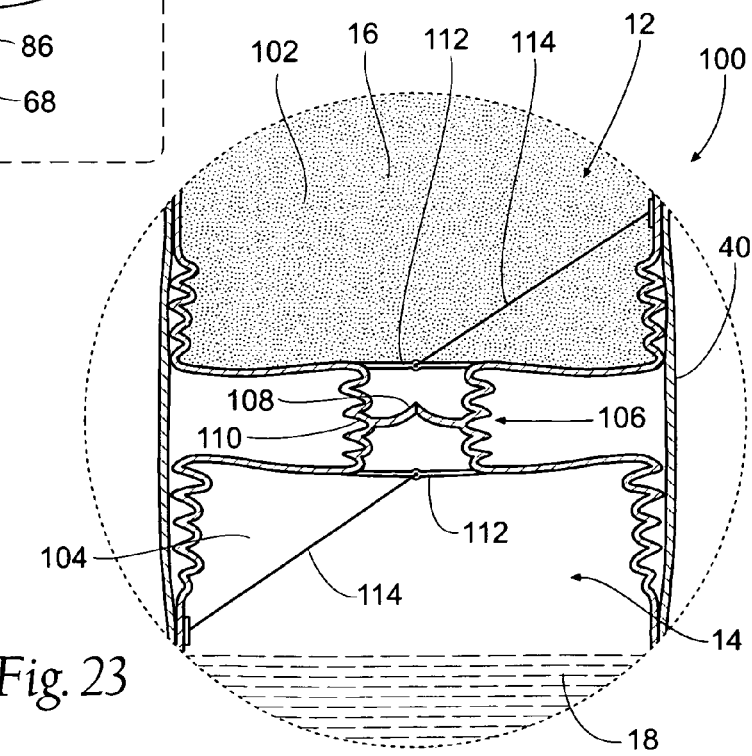
FIG. 23 is a front elevation interior section view of the valve assembly formed in the device taken generally along line 23-23 in FIG. 22, prior to the removal of the outer protective skirt.

As FIG. 23 shows, within the outer skirt 112, the mid-regions of the containers 102 and 104, and the valve passage 110 itself, are desirably plicated or pleated or otherwise bunched together, shortening the length of each container 102 and 104 and the valve passage 110. Alternatively, the placations can be performed in the walls of the containers 102 and 104 and/or valve passage 110. The presence of the overlaying skirt 112 serves to isolate the valve passage 100 from unintended contact during transport and prior to use.

As FIG. 23 shows, the walls of each container 102 and 104 that overlay opposite ends of the valve passage 110 each includes an integrated tear member 112. As FIG. 23 shows, each integrated tear member 112 is coupled by an internal pull string 114 to an adjacent side wall of the respective container 102 and 104. The internal pull string 114 is normally held in slight tension when the device 100 is in the plicated condition shown in FIG. 22 (i.e., when the mid-regions of the containers 102 and 104, and the valve passage 110 itself, are plicated and held in this condition by the outer shirt 112). When the device 100 is in the plicated condition, the tension on the internal pull string 114 is not sufficient to affect the tear member 112. The walls of each container 102 and 104 that overlay opposite ends of the valve passage 110 remain closed. When the device 100 is in the plicated condition, the chambers 12 and 14 and their contents remain isolated and separated prior to use.

Figure 24:
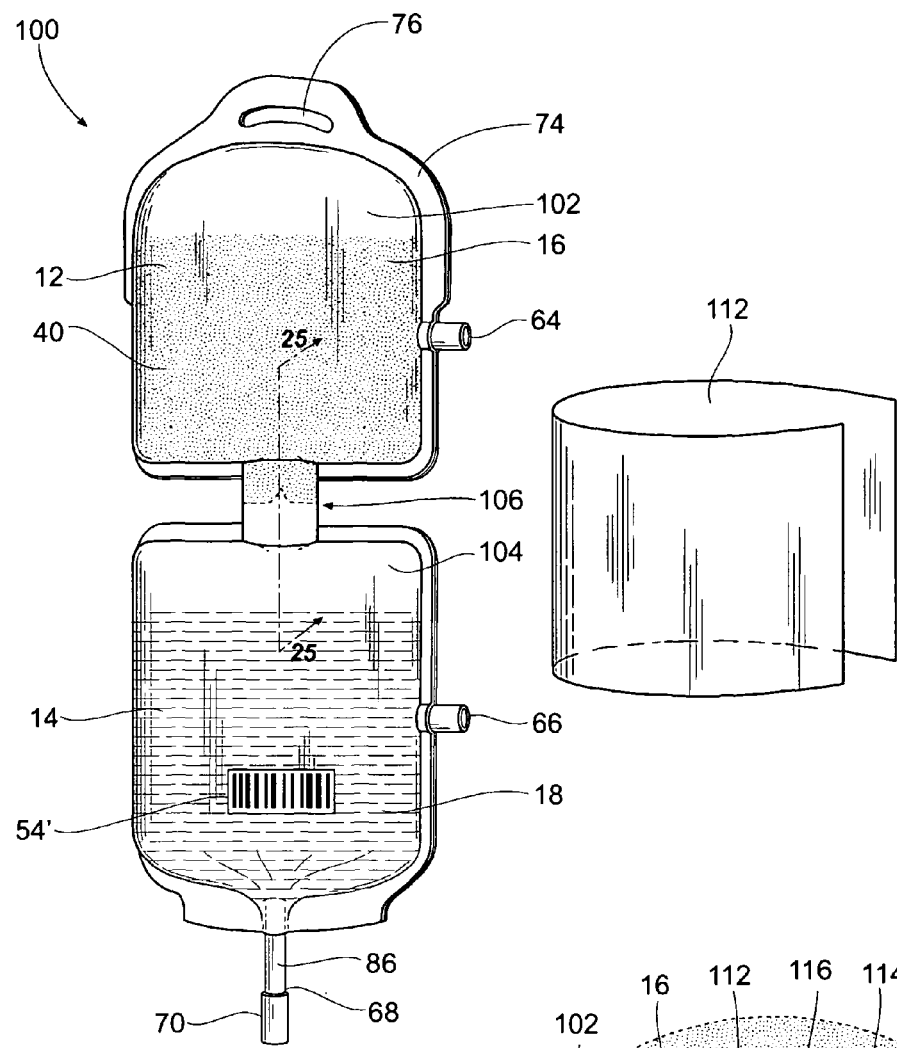
FIG. 24 is a front elevation view of the device shown in FIG. 22, after the removal of the outer protective skirt and prior to manipulating the device to reconstitute the freeze-dried materials.

As FIG. 24 shows, the skirt 112 can be torn and removed by operation of an integrated tear member 116 (in the manner shown in FIG. 3), to place the device 100 in the condition shown in FIG. 24. As FIG. 24 shows, upon removal of the skirt 112, the placations of the walls of the containers 102 and 104 and valve passage 110 are relieved, and the device 100 lengthens.

Figure 25:
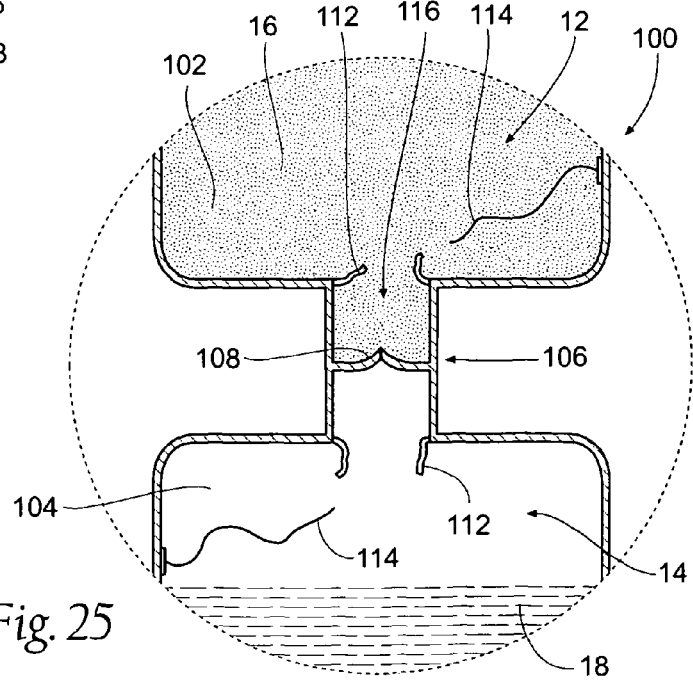
FIG. 25 is a front elevation interior section view of valve assembly like that shown in FIG. 23, taken generally along line 25-25 in FIG. 23 after removal of the outer protective skirt.

As FIG. 25 shows, when the device 100 lengthens, tension on the internal pull string 114 is increased. The increased tension is sufficient to activate the tear member 112, tearing open regions 116 of the walls on opposite ends of the valve passage 110 (as FIG. 25 shows). The open regions 116 place the first and second chambers 12 and 14 into communication through the valve passage 110.

Figure 26:
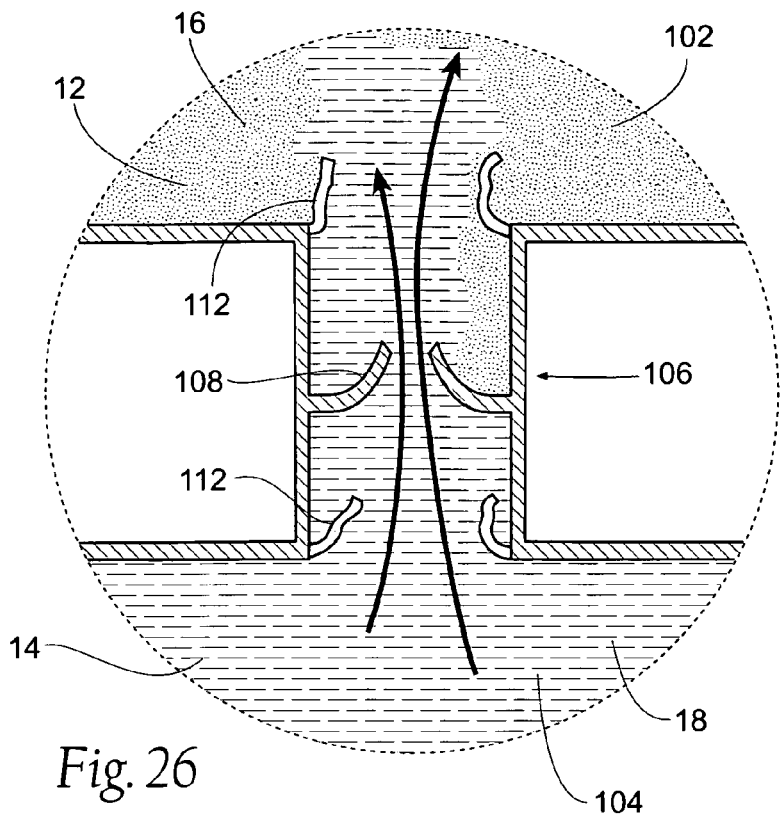
FIGS. 26 and 27 are front elevation interior section views showing the passage of materials through the valve assembly shown in FIG. 25 by manipulating the device to reconstitute the freeze-dried materials.
Figure 27:
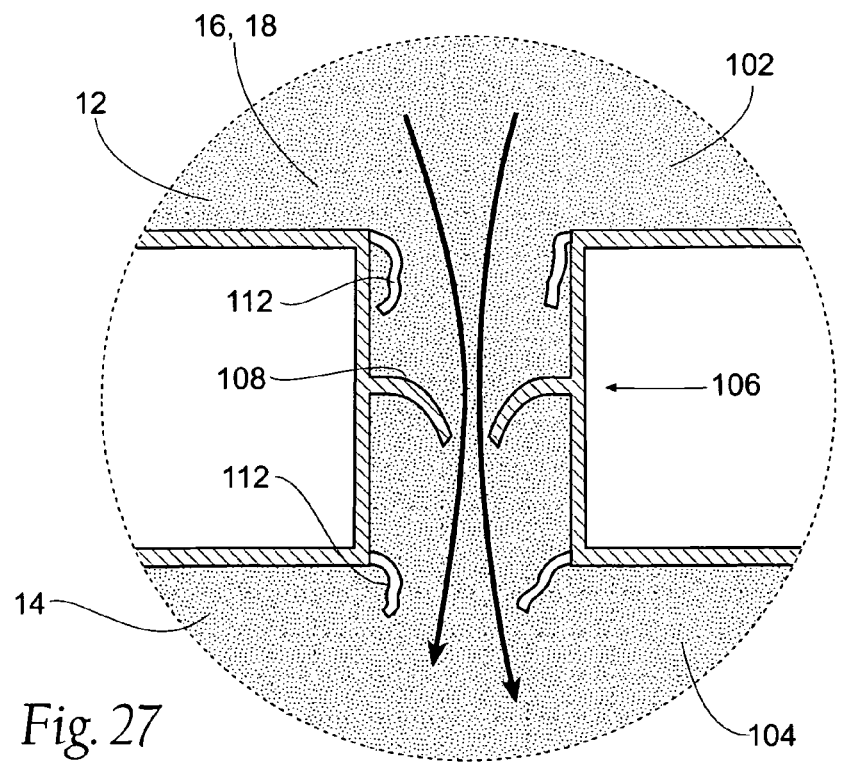

With the regions 116 opened, the caregiver can proceed to manipulate the device 100 in the same manner previously described with respect to device 10 (as shown in FIGS. 10 to 16). The caregiver creates the fluid pressure differential across the valve 108 by selectively squeezing one container and not the other container. Fluid is expelled in response to the fluid pressure differential through the valve 108 from the container that is squeezed into the container that is not squeezed to mix and reconstitute the freeze-drive material for administration. Transfer of materials in opposite directions between the chambers 12 and 14 through the valve passage 110 as a result of the manipulation of the containers 102 and 104 is shown in FIGS. 26 and 27.

B. Dual Containers with Transfer Set

FIG. 30 shows a representative embodiment of a system 200 for storing an administering a freeze-dried material. The system 200 comprises a first collapsible container 202 and a second, separate collapsible container 204. The system 200 further comprises a transfer set 206 for establishing fluid communication between the first and second containers 202 and 204.

The system 200 shares many of the technical features of the devices shown in FIGS. 1 and 22, albeit the particular structure differs.

The first container 202 comprises the dry chamber 12 as previously described, and is sized and configured to contains an aliquot of a freeze-dried material 16, such as a freeze-dried single donor unit of human plasma. To maintain a direct traceable link between the source plasma and the material 16 in the chamber 12, the container 202 preferably includes a bar coding and tagging 54 (see FIG. 30), which is indicative of the human plasma identification (source, blood type, date of collection, etc.). In this way, the container 202 maintains a traceable link back to the human donor source.

The second container 204 comprises the wet chamber 14, as previously described, and is sized and configured to contain a reconstituting liquid 18 for the freeze-dried material 16. As before described, the reconstituting material 18 can comprise, e.g., sterile water, which may be degassed, if desired.

In use (see FIG. 31), using the transfer set 206, the sterile water in the wet chamber 14 is mixed with the freeze-dried plasma in the dry chamber 12 to provide plasma for transfusion. The plasma is reconstituted and administered on site using the system 200.

As before described, the first container 202 is sized and configured to maintain the freeze-dried material 16, prior to its reconstitution, in a vacuum packed, aseptic, moisture-free and low concentration oxygen environment, preferably accommodating long term storage, e.g., at least 2 years at room temperature. Stored in this environment, the freeze-dried material 16 retains its desired qualities for transfusion.

As also before described, the second container 204 is sized and configured to maintain the reconstituting liquid 18, prior to its mixing with the freeze-dried material 16, in an aseptic environment and at a low gas concentration, preferably accommodating long term storage, e.g., at least 2 years at room temperature.

The volume of each of the containers 202 and 204 is preferably approximately 50% larger than the volume of the freeze-dried material 16 in the first chamber 12. This provides ample volume within the containers 202 and 204 for mixing the freeze-dried material 16 and reconstituting liquid 18, either in the first container 202, or the second container 204, or both, as will be described in greater detail later.

The containers 202 and 204 may be made, e.g., of an inert medical grade plastic material, such as polyvinyl chloride, polyethylene, polypropylene, or high density polyethylene. One or both of the container 202 and 204 can comprise a multi-laminate of polymer layers for greater durability, e.g., to resist tearing and puncturing that could be encountered in normal handling.

The material of the containers 202 and 204 can be selected to be transparent, if desired, to allow visual inspection of the contents of the chamber 12 and 14. The material in the first container 202 can be selected to provide a gas-impermeable barrier, such as a metallized, reduced gas-permeability coating, or a metal laminate. In this case, the wall of the first chamber 12 may be opaque.

Each container 202 and 204 may be enveloped prior to use by a vacuum sealed over-wrap 208 (shown in phantom lines in FIG. 30), made, e.g., of a metallized, gas impermeable material. The over-wrap 208 enhances shelf-stability. The transfer set 206 also is desirably packaged in a sterile over-wrap 208 prior to use (as shown in phantom lines in FIG. 31).

The transfer set 206 includes plastic needles or spikes 210 at each end. An outer tear-away skirt or cap 216 can placed or wrapped around each needle or spike 210 to preserve sterility until the instant of use.

In use, the needles or spikes 210 are sized and configure to puncture conventional pierceable membranes 212 located within port tubes 214 coupled in fluid communication with each container 202 and 204. Each membrane 212 normally seals the respective container 202 and 204 until pierced by the respective needle or spike 210 of the transfer set 206. Once pierced by the needle or spike 210, fluid communication is opened through the port tube 214.

With the port tubes opened 214 opened, the caregiver can proceed to manipulate the system 200 to transfer the reconstituting liquid 18 from the second container 204 into contact with the freeze-dried material 16, as FIG. 31 shows, The caregiver can create a fluid pressure differential across the transfer set 206 by selectively squeezing one container and not the other container. Fluid is expelled in response to the fluid pressure differential through the transfer set 206 from the container that is squeezed into the container that is not squeezed to mix and reconstitute the freeze-drive material for administration. Transfer of materials in opposite directions back and forth between the chambers 12 and 14 can proceed as necessary to reconstitute the freeze-dried material, at which time administration can occur.

At this time, the caregiver can couple the administration fitting 70 (shown coupled to the first container 202) to an appropriate administration set, for transfer of the reconstituted material to the circulatory system of an individual, as shown in FIG. 31, in the same manner as before described with reference to FIG. 16. The administration fitting 70 can also be coupled to the second container 204, or both the first and second containers 202 and 204.

C. Alternative Ways to Package the Reconstituting Liquid

Figure 28A:
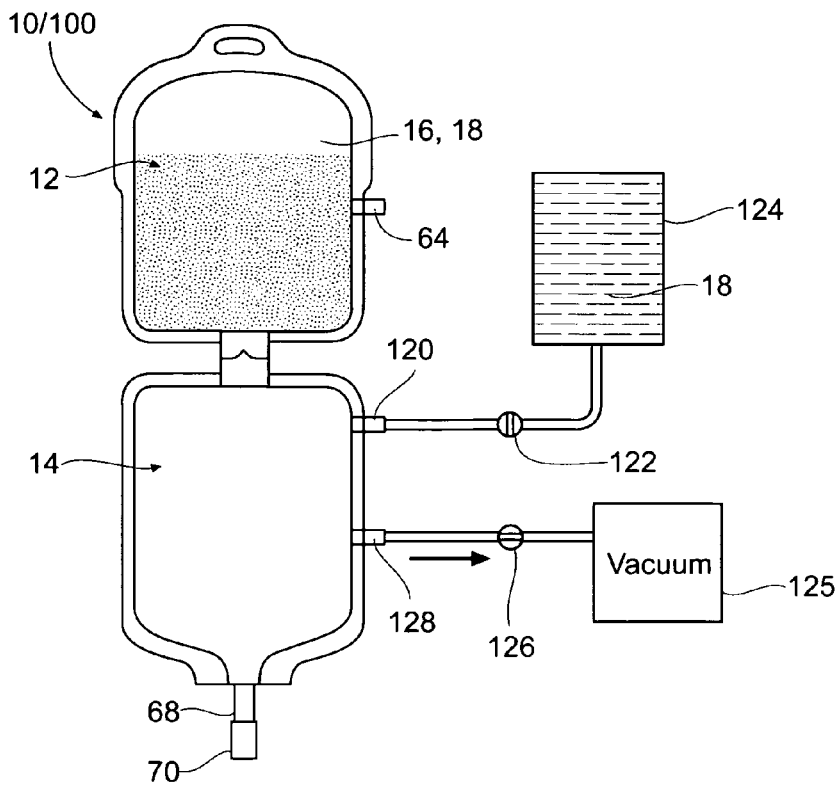
FIGS. 28A and 28B are largely schematic views of an alternative way of packaging the reconstituting liquid for the freeze-dried material in the second chamber of the device of the type shown in FIG. 1 or 22.
Figure 28B:
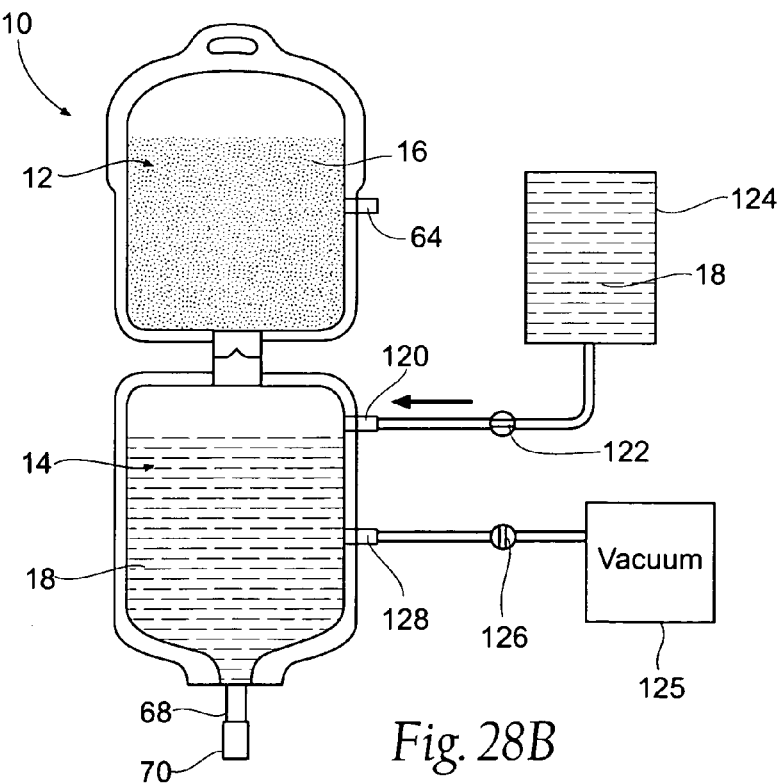

FIGS. 28A/B and 29A/B shows alternative ways to package the reconstituting liquid 18 in a device 10 or device 100 as previously described. In these alternative ways, it is not necessary to use the administration port 68 to convey the reconstituting liquid 18, but can be closed and sealed in a pre-packaging operation.

In one alternative representative embodiment (see FIG. 28A/B), the wet chamber 14 includes two packaging ports 120 and 128. In use (see FIG. 28A), the first port 120 is coupled to a source 124 of the reconstituting liquid 18 via a first inline valve 122. The second port 128 is coupled to a vacuum source 125 via a second inline valve 126.

As shown FIG. 28A, the first valve 122 is closed and the second valve 126 is opened. A vacuum is applied to the interior of the chamber 14. As shown in FIG. 26B, the first valve 122 is opened and the second valve 126 is closed. The reconstituting liquid 18 is conveyed by gravity flow into the chamber 14. Both packaging ports 120 and 128 are sealed.

In another alternative representative embodiment (see FIGS. 29A/B), the wet chamber 14 includes a single packaging port 130. In use (see FIG. 29A), the port 130 is coupled to a source 132 of the reconstituting liquid 18 and a vacuum source 134 through a two way valve 136.

Figure 29A:
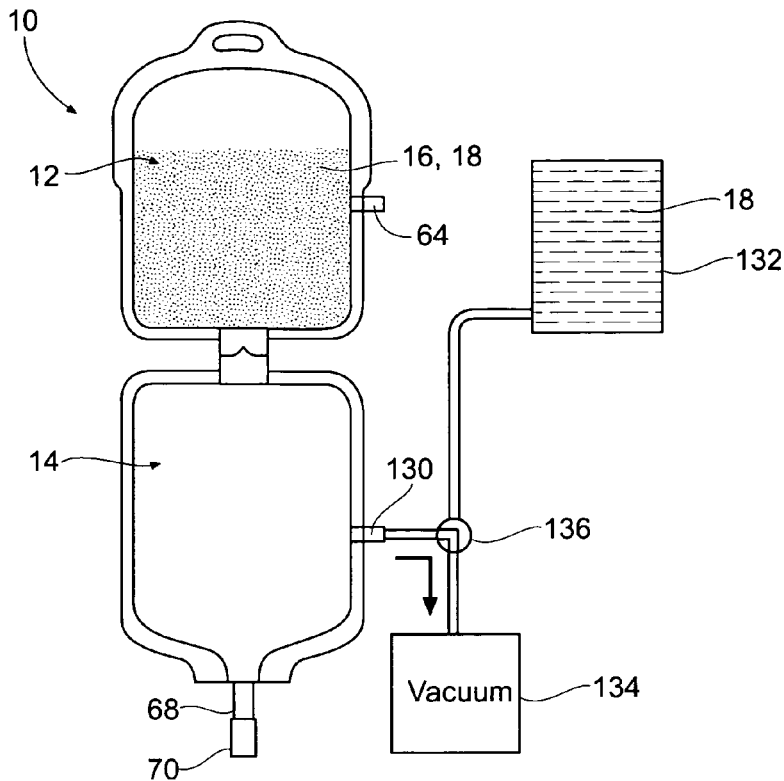
FIGS. 29A and 29B are largely schematic views of another alternative way of packaging the reconstituting liquid for the freeze-dried material in the second chamber of the device of the type shown in FIG. 1 or 22.
Figure 29B:
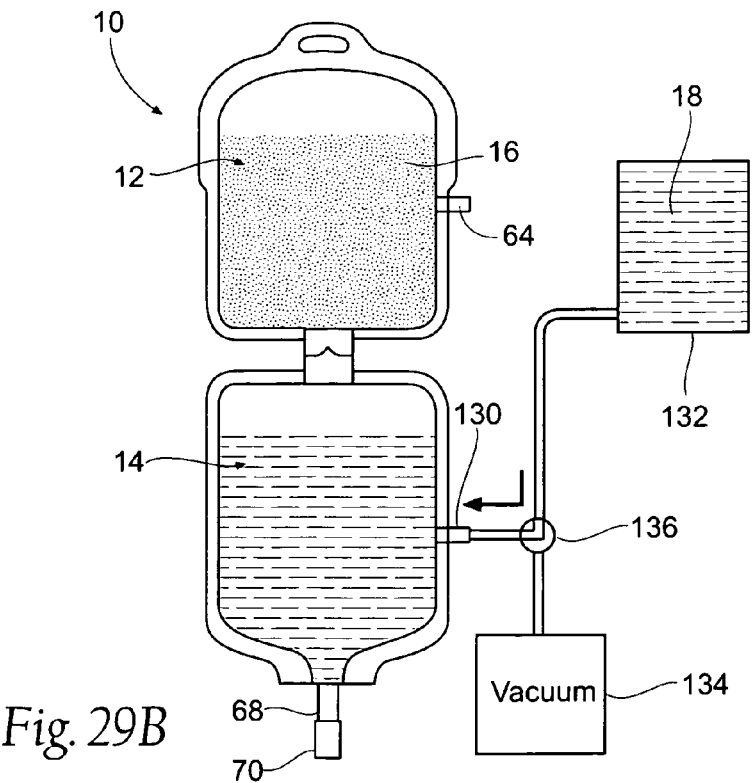

As shown FIG. 29A, the two way valve 136 is operated to close communication with the liquid source 132 and to open communication with the vacuum source 134. A vacuum is applied to the interior of the chamber 14. As shown in FIG. 29B, the two way valve 136 is operated to open communication with the liquid source 132 and to close communication with the vacuum source 134. The reconstituting liquid 18 is conveyed by gravity flow into the chamber 14. The packaging port 130 is sealed.

In both arrangements, the administration port 68 can be inserted and sealed close in a pre-packing operation. The administration port 68 is not used until it is time to administer the reconstituted freeze-dried material, as shown in FIG. 16.

D. Alternative Ways to Package the Freeze-Dried Material

Figure 33:
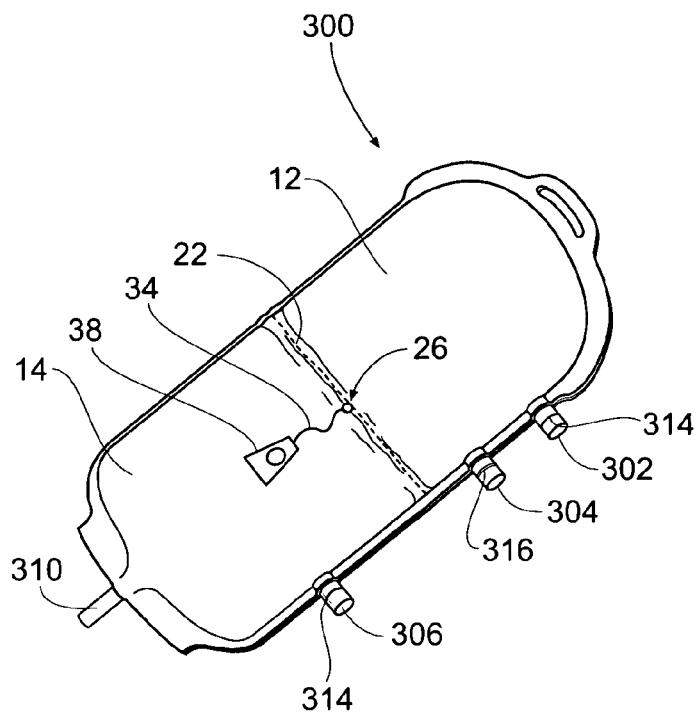
FIG. 33 is a front elevation view of a device for storing freeze-dried material, e.g., freeze-dried human plasma, and a reconstituting liquid for the freeze-dried material, the device being sized and configured for freeze-drying material in situ within the device.

In an alternative embodiment, the material 16 can be freeze-dried in situ within the chamber 12. In this arrangement, as FIG. 33 shows, a device 300 is compartmentalized by a sealing wall 22 into a chamber 12 and a chamber 14, in the manner previously described. The sealing wall 22 includes a septum 26 with pull string 34 and tab 38, as previously described.

To accommodate freeze-drying of the plasma within the chamber 12, the device 300 is made of a material that resists cracking at the low temperatures (e.g., below −33° C.) encountered during freeze-drying. Candidate materials include polyolefin materials, polyurethane materials, polyurethane, elastomer materials, and polysilicone materials. Polyvinyl chloride materials treated to withstand low temperatures can also be used.

The device 300 also includes first and second aseptic ports 302 and 304, which communicate with the first chamber 12. The first aseptic port 302, in use, conveys liquid plasma into the chamber 12 for freeze-drying. The first port 302 is desirably normally closed by a pierceable membrane or septum 314. The second aseptic port 304 is normally closed by a gas permeable membrane such as a gas permeable membrane 316. In use, the gas permeable membrane 316 accommodates the transport of vapors and gases into and out of the chamber 12 during and after the freeze-drying process, but otherwise prevents liquid from leaving the chamber 12. The gas permeable membrane 316 can comprise, e.g., a nylon material, a polytetrafluoroethylene (PTFE) material, or a polypropylene material.

The device 300 also includes an aseptic port 306, which communicates with the second chamber 14. The port 306, in use, conveys a reconstituting fluid into the second chamber 14, as previously described (e.g., see FIGS. 29A and 29B). The first port 302 can also be normally closed by a pierceable membrane or septum 314.

An administration port 310 is also heat sealed in communication with the second chamber 14. The administration port 310, in use, conveys reconstituted material from the second chamber 14 for administration to an individual, as previously described.

Figure 34:
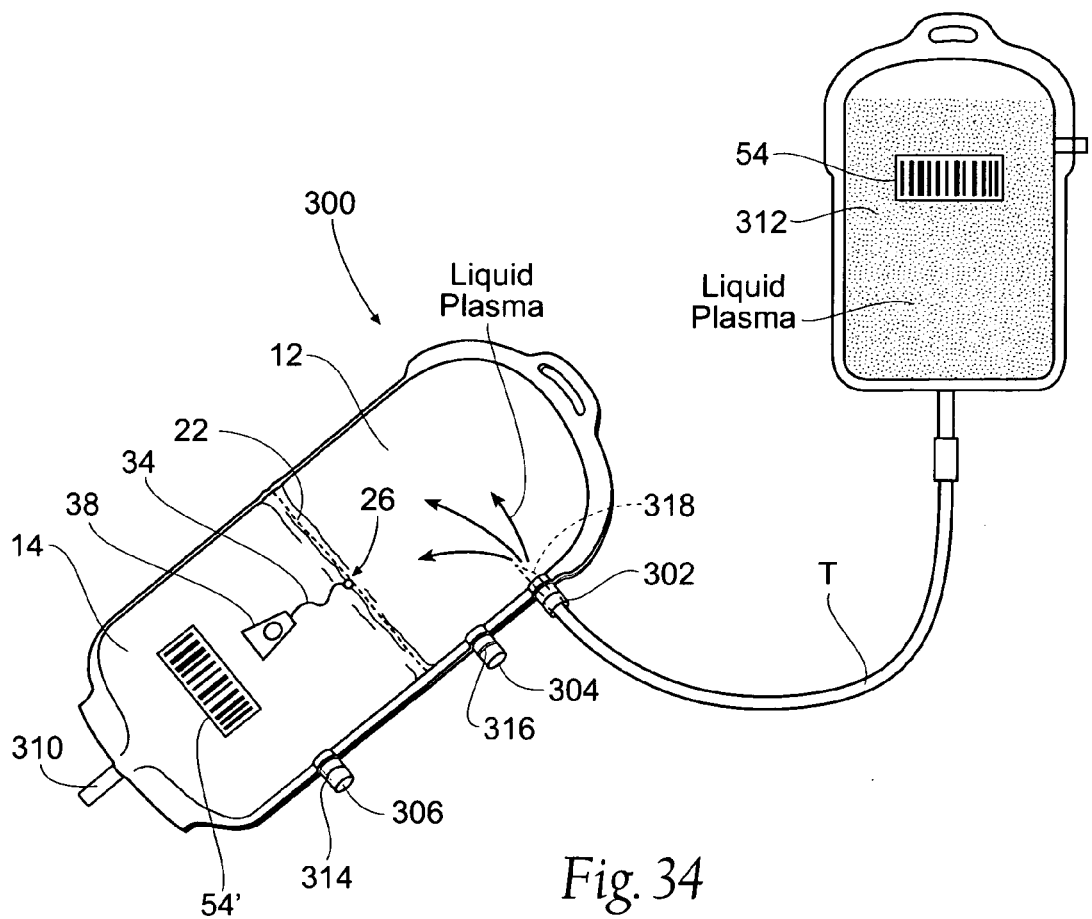
FIG. 34 is a front elevation view of the device shown in FIG. 33, showing the conveyance of liquid plasma into the device for freeze-drying in situ within the device.

As FIG. 34 shows, the first port 302 is sized and configured to be attached to tubing T coupled to a source of liquid plasma 312. In the illustrated embodiment, the tubing T includes a spike or needle 318 that pierces the membrane 314 in the port 302, to open fluid communication through the port 302 into the chamber 12.

Through the tubing T, a desired volume of liquid plasma is conveyed from the source 312 into the first chamber 12. Following the conveyance of liquid plasma into the first chamber 12, the tubing T is removed, and the port 302 is sealed closed. At this stage of processing, the second chamber 14 remains empty, as FIG. 34 shows.

To maintain a direct traceable link between the source plasma and the material 16 that will be freeze-dried in the chamber 12, the device 300 preferably includes a bar coding and tagging 54' (see FIG. 31), which is indicative of the human plasma identification (source, blood type, date of collection, etc.), and which replicates or is otherwise linked to the bar coding and tagging 54 placed on the source plasma bag 312. In this way, the device 300 maintains a traceable link back to the human donor source.

Figure 35:
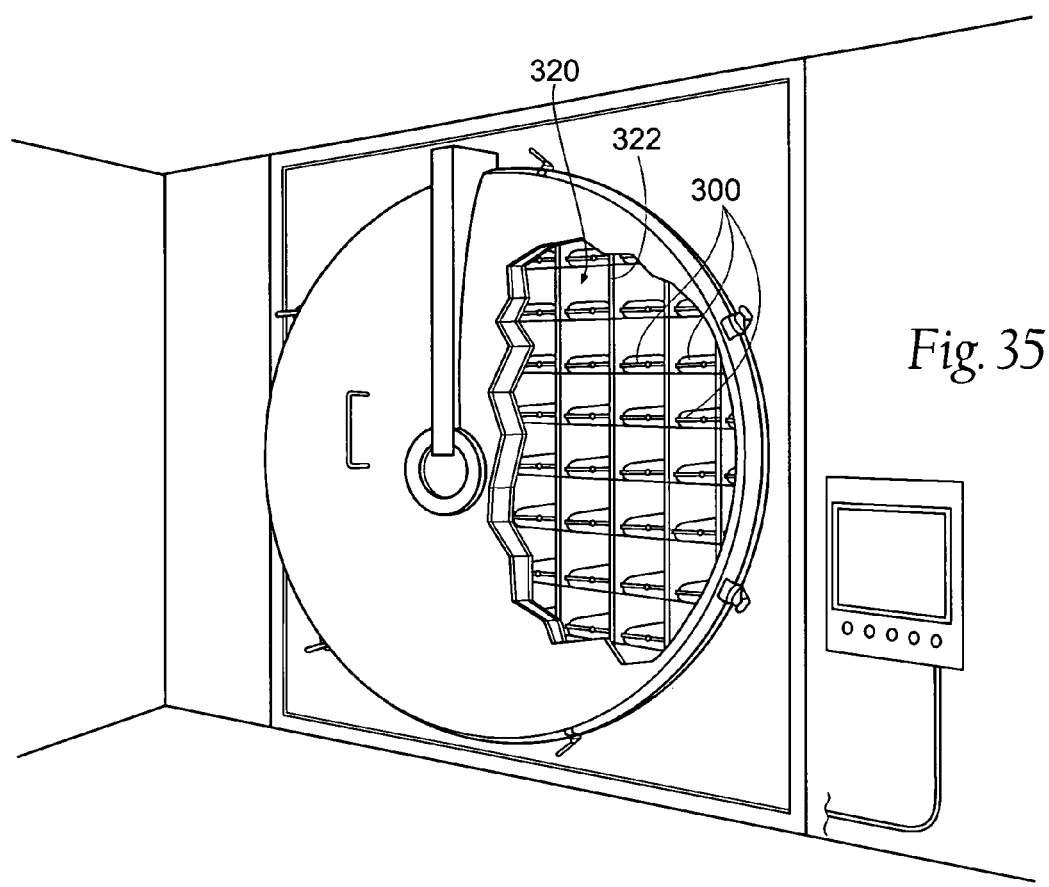
FIG. 35 is a perspective view of several devices shown in FIG. 34 after placement in a freeze-dryer for the purpose of freeze-drying liquid plasma in situ within each of the devices.

As shown in FIG. 35, one or more devices 300, with each chamber 12 filled with liquid plasma, is placed inside a freeze dryer 320 on an aseptic freeze dryer shelf surfaces 322. Once loaded, the freeze dryer cycle is started. This cycle generally cools the human plasma to near −45° C. and freezing for 2 to 8 hours, followed by cooling of the freeze dryer condenser and application of vacuum to start the freeze drying cycle. As a result, a freeze-dried human plasma cake 324 is formed in situ within the chamber 12 of each device 300 (see FIG. 36).

The representative parameters for the freeze-drying process have been previously described and are incorporated herein by reference.

Throughout the freeze drying process, the gas permeable membrane 316 within the port 304 accommodates passage of gases, e.g., water vapor as it sublimates from the liquid plasma during freeze-drying, but otherwise prevents passage of liquid plasma from the chamber 12.

Figure 36:
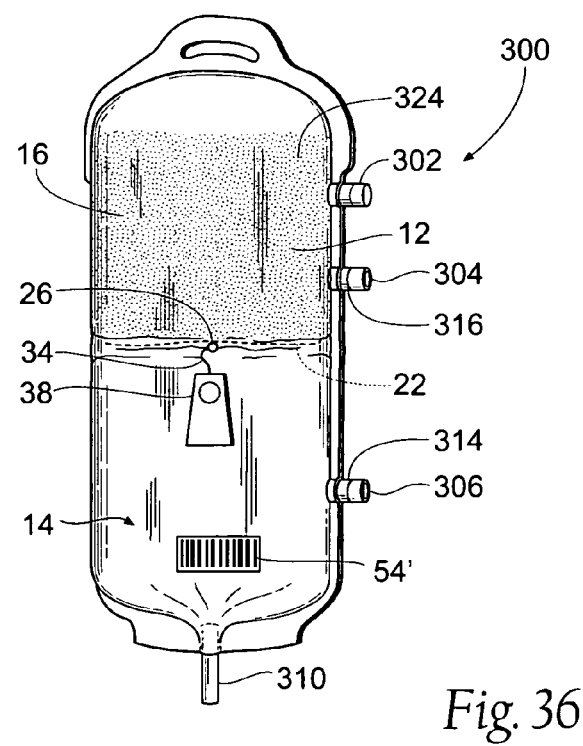
FIG. 36 is a front elevation view of a device shown in FIG. 35 after removal from the freeze-dryer, showing the freeze-dried plasma cake that has been formed in situ within the device, and prior to the conveyance of a reconstituting material into the device.

As shown in FIG. 36, after freeze-drying, the devices 300 with the freeze dried cakes 324 in their chambers 12 are removed from the freeze dryer 320.

Preferably, an aseptic vacuum is applied through the port 304. Upon achieving near 100 mTorr of pressure, the port 304 is heat sealed closed. This evacuation process provides for the eventual ability to mix and reconstitute the human freeze dried plasma without introduction of bubbles and without foaming. The vacuum would also cause the plasma cake 324 to be compacted to a fine powder, forming the freeze-dried material 16 within the chamber 12. The devices 300 can be maintained under a nitrogen or argon blanket to exclude moisture and oxygen until subsequent processing.

Figure 37:
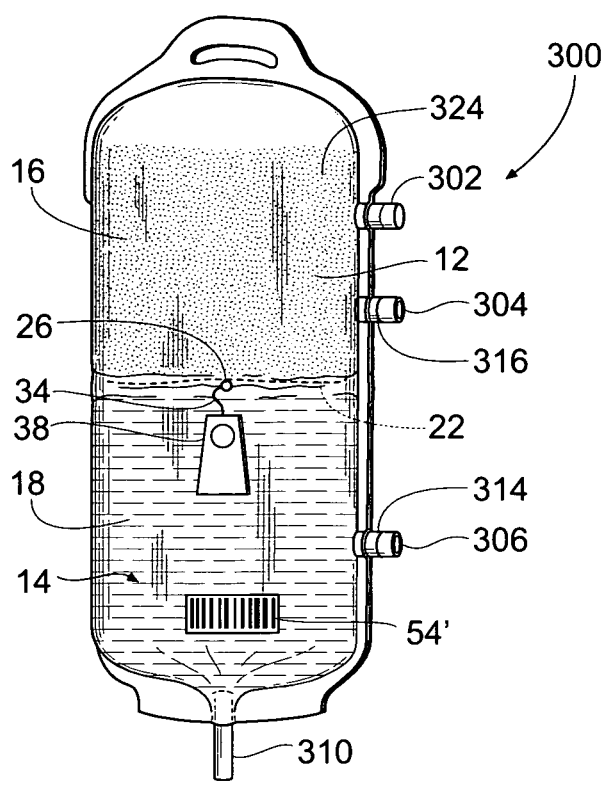
FIG. 37 is a front elevation view of a device shown in FIG. 36 after the conveyance of a reconstituting material into the device.

Next (see FIG. 37), the reconstituting liquid 18 is introduced into the second chamber 14 through the port 306, for example, in manner shown in FIGS. 29A and 29B. The port 306 is then sealed.

Figure 38:
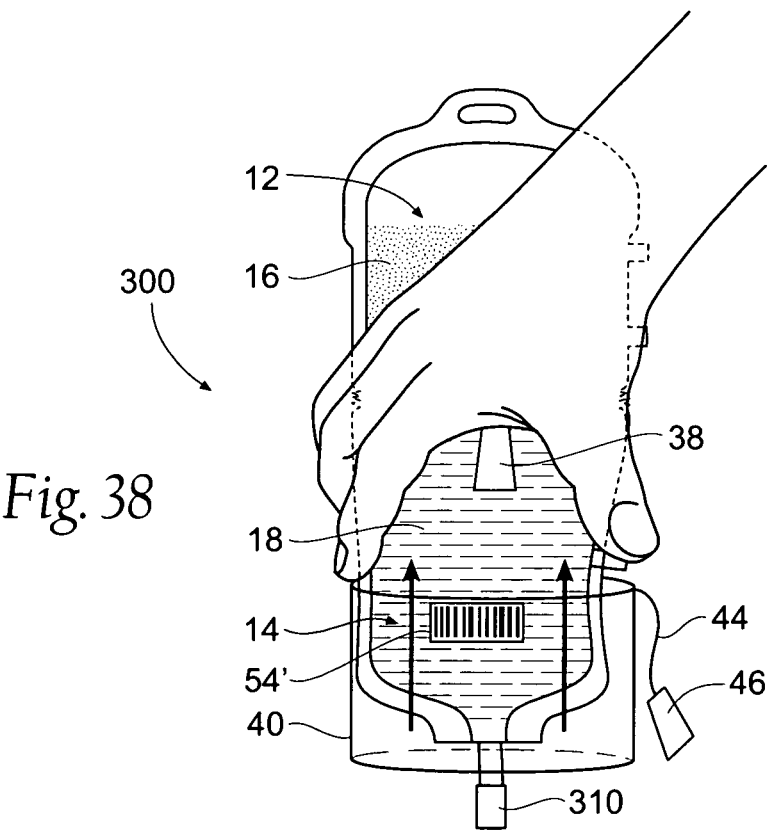
FIG. 38 is a front elevation view of placing an outer protective sleeve about the device shown in FIG. 37, after conveyance of the reconstituting material into the device, to create the device of a type shown in FIG. 1.

As FIG. 38 shows, after packaging the freeze-dried material 16 and the reconstituting liquid 18 in the manner just described, the wall of the device 300 is plicated in the region of the sealing wall 22, as previously described, and an outer skirt 40 (with pull string 44 and tab 46) attached, as also previously described. An overwrap 20 can be applied, as shown in FIG. 1, if desired.

The device 300 is ready for storage, transport, and use.

It should be appreciated that liquid plasma could be freeze-dried in situ within the container 202 shown in FIG. 30 in the same manner as just described.

V. Devices, Systems and Methods for Freeze-Drying and Storing Materials for Reconstitution A. Multifunctional Freeze-Drying and Storage Vessel FIGS. 39A to 39D show a representative embodiment of a multifunctional device 400 for freeze-drying, storing, reconstituting, and administering a material, such as plasma. The device 400 is sized and configured to receive the material while it undergoes freeze-drying within the device 400. The device 400 is also sized and configured to serve as a vessel for the freeze-dried material while it undergoes transport, handling, and storage prior to reconstitution at an intended site. The device 400 is also sized and configured to further serve as a vessel in which the freeze-dried material can be reconstituted. The device 400 is also sized and configured to also serve as a vessel from which the freeze-dried material, after being reconstituted, can be delivered to an individual in a safe and aseptic manner. Using the multifunctional device 400, a given material can be freeze-dried, transported, stored, reconstituted, and administered in a single vessel.

Figure 39:
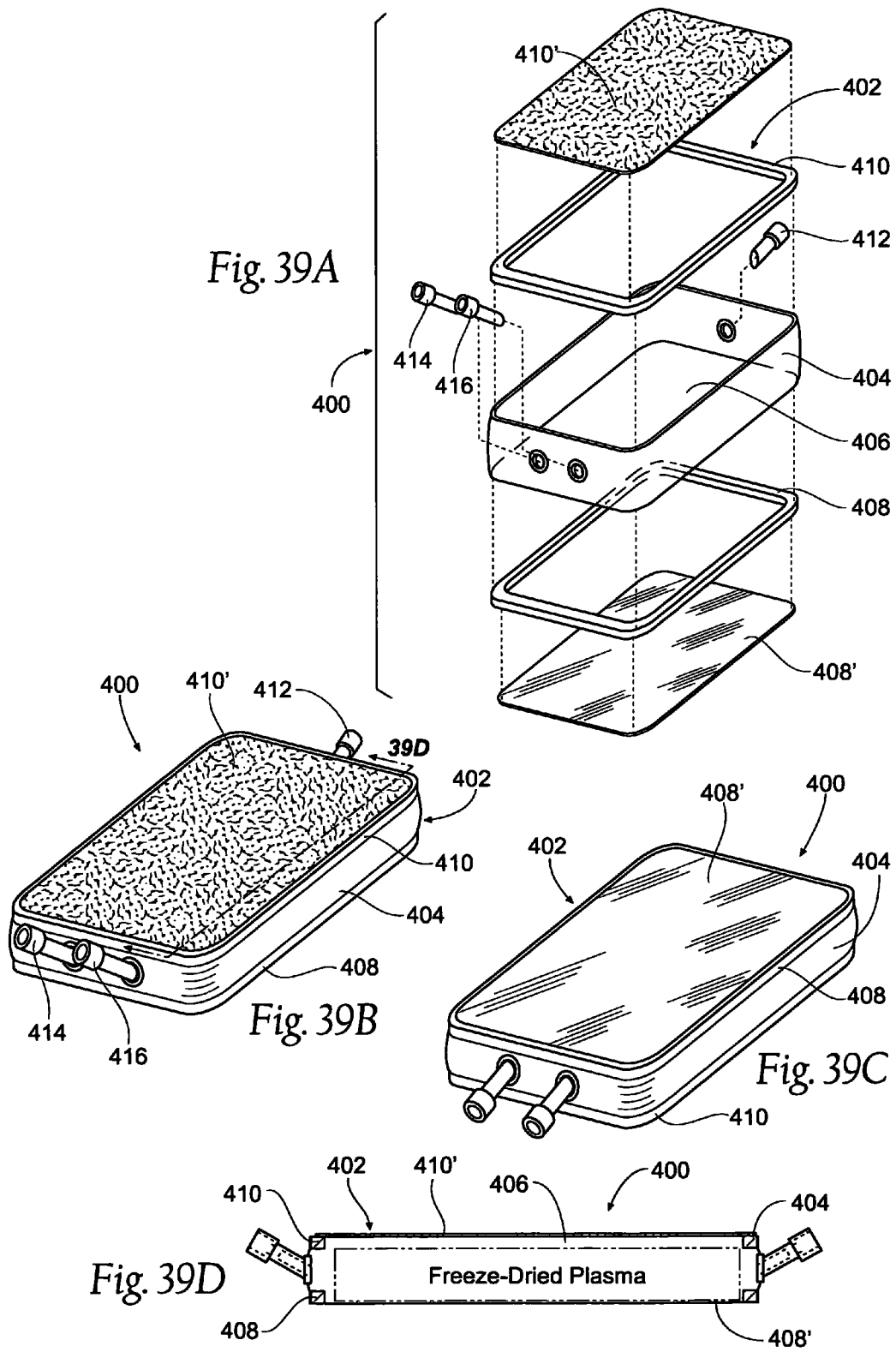
FIG. 39A is an exploded perspective view of a multifunctional device for freeze-drying, storing, reconstituting, and administering a material, such as plasma, comprises a vessel made of several components having different physical properties to thereby serve different functions.
FIG. 39B is an assembled perspective view of the device shown in FIG. 39A, showing the flexible side wall component and transparent, gas impermeable end component.
FIG. 39C is an assembled perspective view of the device shown in FIG. 39A, showing the flexible side wall component and the gas permeable end component.
FIG. 39D is an assembled side elevation view of the device shown in FIG. 39A, taken along line 39D-39D of FIG. 39C.

As shown in the exploded view of FIG. 39A, the device 400 comprises a vessel 402 made of several components having different physical properties to thereby serve different functions. As shown, the vessel 402 includes a side wall component 404 that peripherally encircles an open interior space 406. The vessel 402 also includes first and second end components 408 and 410 that overlay the side wall component 404, enclosing the interior space 406. The vessel 402 also includes first, second, and third port components 412, 414, and 416 that pass through regions of the side wall component 404 to provide fluid communication into the interior space 406 bounded by the side wall component 404 and the first and second overlaying end components 408 and 410.

Assembled together (as FIGS. 39B to 39C show), the various components form a unitary, multifunctional vessel 402 in which a given material can be freeze-dried, then transported and stored, and then reconstituted, and then administered.

As shown in FIGS. 39A to 39D, the first and second end components 408 and 410 comprise frames made of a rigid or semi-rigid material selected to form a lightweight, yet durable structural skeletons for the ends of the vessel 402. The material for the first and second end components 408 and 410 can comprise, e.g., non-plasticized polyvinyl chloride, or polyethylene, or polypropylene, or high density polyethylene. The material is desirably inert and of a medical grade sufficient for contact with animal tissue and fluids. The frames defined by the first and second end component 408 and 410 can, e.g., be molded in the desired shape and size.

The frames defined by the first and second end components 408 and 410 define and maintain a shape for the vessel 402, as well as provide overall structural support and attachment sites for other components of the vessel 402. The frames defined by the first and second end components 408 and 410 provide for the vessel 402 uniting structural elements that withstand pressure conditions and other forces imposed upon the vessel 402 during freeze-drying and subsequent handling.

The frames defined by the first and second end components 408 and 410 each supports a panel of material, respectively 408' and 410'. In the illustrated embodiment, the panels of material 408' and 410' span horizontally across the respective end component 408 and 410. The panels of material 408' and 410' are peripherally sealed to the frames defined by the end components 408 and 410, e.g., by adhesives or heat sealing techniques.

The materials 408' and 410' selected for the panels differ, because they serve different functions. This technical feature will be described in greater detail later.

The side wall component 404 is appended to the frames defined by the first and second end components 408 and 410. The side wall component 404 spans in a vertical direction between the side edges of the end components 408 and 410. The side wall component 404 is peripherally sealed to the side edges of the end components 408 and 410, e.g., by adhesives or heat sealing techniques.

The sidewall component 404 and the first and second end components 408 and 410 provide a closed, sealed integrity to the interior space 406.

The side wall component 404 comprises a flexible, gas impermeable material. The material is also desirably inert and of a medical grade sufficient for contact with animal tissue and fluids. The material for the side wall component 404 can comprise, e.g., plasticized polyvinyl chloride, or polyethylene film, or polypropylene film, or high density polyethylene film. The side wall component 404 can comprise a continuous film of flexible material, as shown in FIG. 39A, or comprise shorter lengths of flexible film material sealed together.

The flexibility of the side wall component 404 accommodates expansion and contraction and flexure of the vessel 402 in response to pressure conditions encountered during freeze-drying and subsequent handling. Desirably, the material of the side wall component 404 also provides resistant to tearing or puncturing during freeze-drying and subsequent handling of the vessel 402. The material for the side wall component 404 is desirably transparent, thereby allowing a user to visually see and inspect the contents of the vessel 402, without allowing gas transmission between the interior space 406 and the ambient environment.

The material 408' of the first end component 408, like the side wall component, is also selected to be gas impermeable, to complement the side wall component 404 in this function. Desirably, the material 408' is also selected to be transparent, to thereby contribute to the visible view into the interior space 406. The material 408' of the first end component 408 can be flexible or rigid, as desired.

It should be appreciated that not all of the material 408' of the first end component 408 need be transparent. The material 408' can include a region of transparency sufficient to permit viewing the interior space 406, with the remainder of the material 408' being gas impermeable and non-transparent.

Like the material for the side wall component 404, the material 408' for the first end component 408 is desirably inert and of a medical grade sufficient for contact with animal tissue and fluids. The material 408' for the first end component 408 can comprise, e.g., plasticized polyvinyl chloride film, or polyethylene film, or polypropylene film, or high density polyethylene film.

The material 410' of the second end component 410 desirably possesses, at least in part, physical characteristics that are different than the physical characteristics of the side wall component 404 and the first end component 408, because the component 410 serves a different function. More particularly, the material 410' of the second end component 410 is selected to be gas permeable; for example, hydrophobic. The gas permeable material 410' accommodates the transport of vapors and gases into and out of the interior space 406 during and after the freeze-drying process, but, if hydrophobic, otherwise prevents liquid from entering or leaving the interior space 406. The gas permeable material 410' can comprise, e.g., a nylon film material, a polytetrafluoroethylene (PTFE) film material or other fluoropolymer film materials, a polypropylene film material, or a polyurethane film material.

The presence of the gas permeable material 410' of the second end component 410 allows water vapor to sublimate from material within the interior space 406 during the freeze-drying process. The presence of the gas permeable material 410' of the second end component 410 also allows inert gases to be introduced into the interior space 406 after the freeze-drying process, if desired, to provide a protective atmosphere within the vessel 402 conducive to long term storage of the material. This technical feature will be described in greater detail later.

The surface area of the gas permeable material 410' of the second end component 410 may affect the rate of sublimation during the freeze-drying process, i.e., the greater the surface area the greater the rate of sublimation. In FIGS. 39A to 39D, the gas permeable material 410' of the second end component 410 overlays the entirely of the end component 410. Alternatively, and as will be described later with respect to the embodiment shown in FIGS. 46 and 47, the gas permeable material 410' of the second end component 410 can comprise a smaller region of the end component 410, with the remainder of the second end component 410 being gas impermeable and, desirably, transparent.

The first, second, and third port components 412, 414, and 416 are sealed within regions of the side wall component 404. The ports 412, 414, and 416 comprise, e.g., extruded or molded medical grade plastic tubes that are sealed, e.g., by heat or adhesive, to the adjacent material of the side wall component 404. The ports 412, 414, and 416 provide fluid communication into the interior space 406 formed by the side wall component 404 and the first and second overlaying end components, as described.

Each port component 412, 414, and 416 is desirably initially sealed with a conventional septum or frangible membrane assembly or by a convention screw-lock luer fitting. Each port component 412, 414, and 416 is sized and configured to be coupled to transfer tubing to enable transfer of materials into and out of the interior space 406, as will be described in greater detail later.

For example, in a representative arrangement, the first port component 412 can be sized and configured, in use, to accommodate introduction of a material in liquid form into the interior space 406 for freeze-drying in situ within the vessel 402. The second port component 414 can be sized and configured, in use, to accommodate introduction of a reconstituting liquid into the interior space 406 for mixing with and reconstituting the freeze-dried material. The third port component 416 can be sized and configured, in use, to accommodate transfer of reconstituted material from the interior space 406. The use of the port components for these purposes will be described in greater detail later.

In the illustrated embodiment, the first port component 412 occupies a different side wall region than the second and third port components 414 and 416. This separation segregates the port component 412 dedicated to the freeze-drying function from the port components 414 and 416 dedicated to the reconstitution and administration functions.

As best shown in FIG. 39D, at least the first port component 412 is desirably oriented at a non-perpendicular angle relative to the side wall component 404. More particularly, the port component 412 angles away from the first end component 408, presenting a high-gravity position above the plane of the gas permeable material 410' of the second end component 410. This orientation minimizes wetting of the gas permeable material 410' of the second end component 410 during introduction of the liquid material into the interior space 406 through the port component 412. Although the freeze-drying process will ultimately dry a wetted material 410' of the second end component 410, prevention of wetting in the first instance may nevertheless be desirable, to maximize the rate of sublimation throughout the freeze-drying process.

Figure 52:
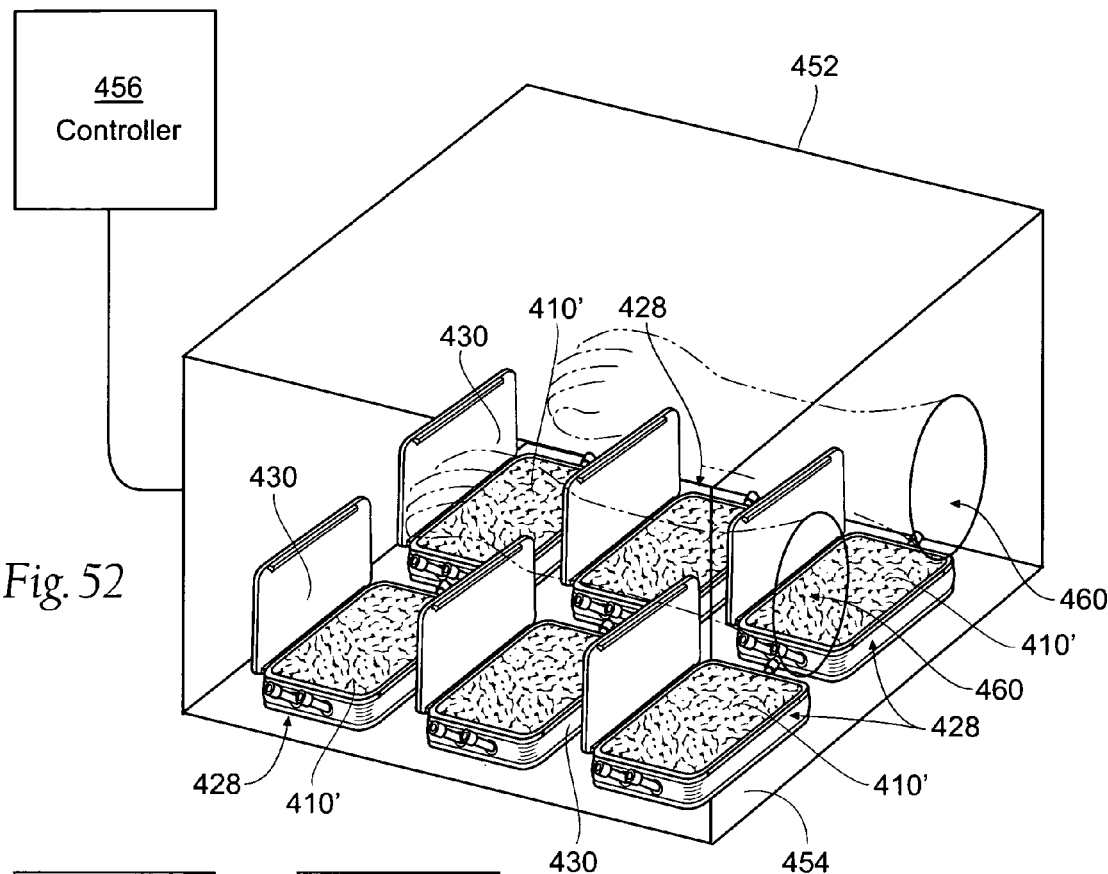
FIG. 52 is a perspective view of the placement of several unitary freeze-dried material storage assemblies shown in FIGS. 50 and 51 into a freeze dryer, the closure covers being in the opened condition, the freeze dryer exposing the unitary freeze-dried material storage assemblies to a range of temperature and vacuum conditions to lyophilize the liquid plasma into freeze-dried plasma, the open closure cover accommodating sublimation of water vapor during drying.

During the freeze-drying process, the vessel 402 sits on a shelf within a freeze-dryer in the orientation shown in FIG. 39D (as also shown in FIG. 52. In this orientation, the gas-impermeable material 408' of the first end component 408 rests on the shelf. The frame defined by the first end component 408 provides a stable platform of support for the liquid material as it undergoes freeze-drying, keeping the vessel 402 upright in this desired orientation.

In this desired upright orientation, the gas permeable gas permeable material 410' of the second end component 410 faces upward into the freeze-drying environment. In this orientation, during drying, sublimating water vapor will escape upward from the material through the gas permeable material 410' of the second end component 410.

Specific details of the use of the vessel 402 before, during, and after the freeze-drying process will be described in greater detail later.

B. Freeze-Dried Material Storage Assembly

As will also be described in greater detail later, after completion of the freeze-drying process, the vacuum condition existing during the drying process may, if desired, be opened to an atmosphere of an oxygen-free, high purity inert gas, such as nitrogen or argon. The oxygen-free inert gas enters the interior space 406 through the gas permeable material 410' of the second end component 410, to exclude moisture and oxygen.

Figure 40:
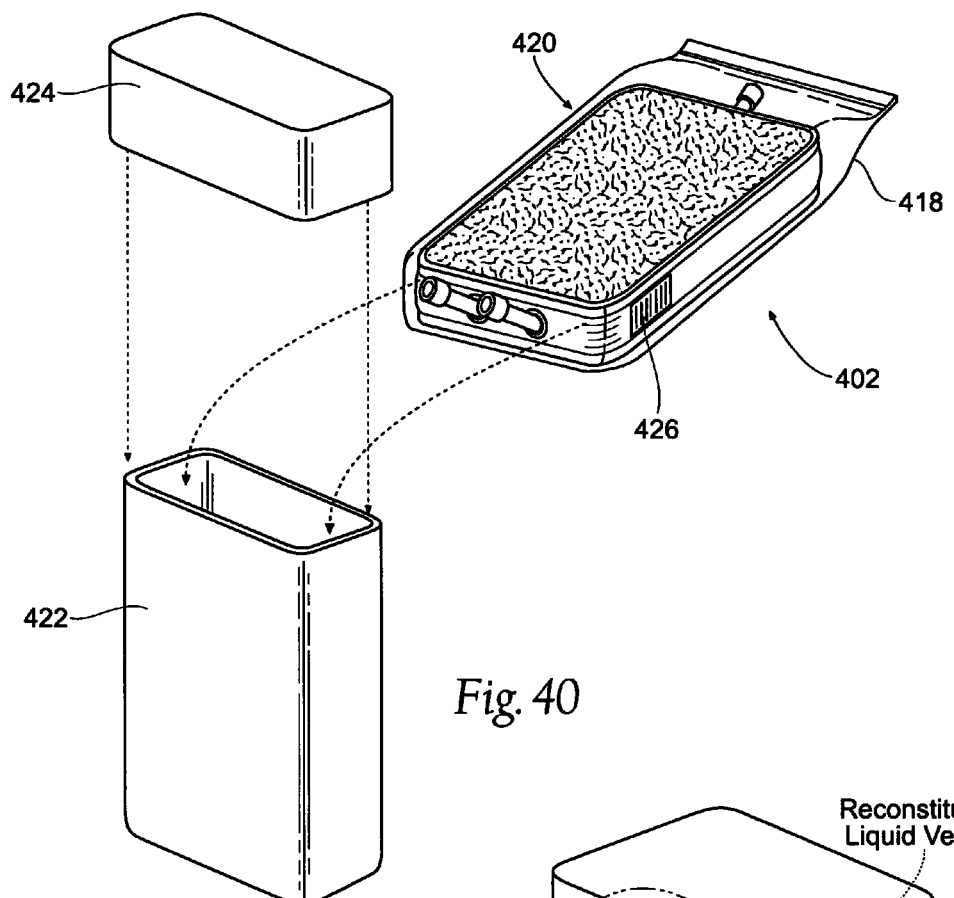
FIGS. 40 and 41A are perspective views of a freeze-dried material storage assembly comprising the vessel shown in FIGS. 39A to 39D sealed within a gas-impermeable overwrap, and also showing in perspective view a rigid outer container with a lid for enclosing the freeze-dried material storage assembly during transport and storage until the instance of use, as FIG. 41 shows.

In this arrangement, while the vessel 402 (now containing the freeze-dried material) is maintained under the blanket of the oxygen-free inert gas, the vessel 402 is placed in a vacuum sealed, transparent vapor barrier or overwrap 418, as shown in FIG. 40. The overwrap 418 is made from a gas-impermeable material and is desirable flexible, e.g., plasticized polyvinyl chloride film, or polyethylene film, or polypropylene film, or high density polyethylene film, as previously described in connection with the first end component 408. Such materials may be used in combination with metallized, reduced gas-permeability coatings, or metal laminates. The vapor barrier or overwrap 418 traps the oxygen-free gas environment within the vessel 402 during transportation and storage.

The vessel 402 and overwrap 418 comprise a freeze-dried material storage assembly 420. The exclusion of moisture and oxygen in the presence of the oxygen-free inert gas trapped by the overwrap 418 prevents degradation of the freeze-dried material carried within the vessel 402 during subsequent transport and storage.

Figures 41A, 41B:
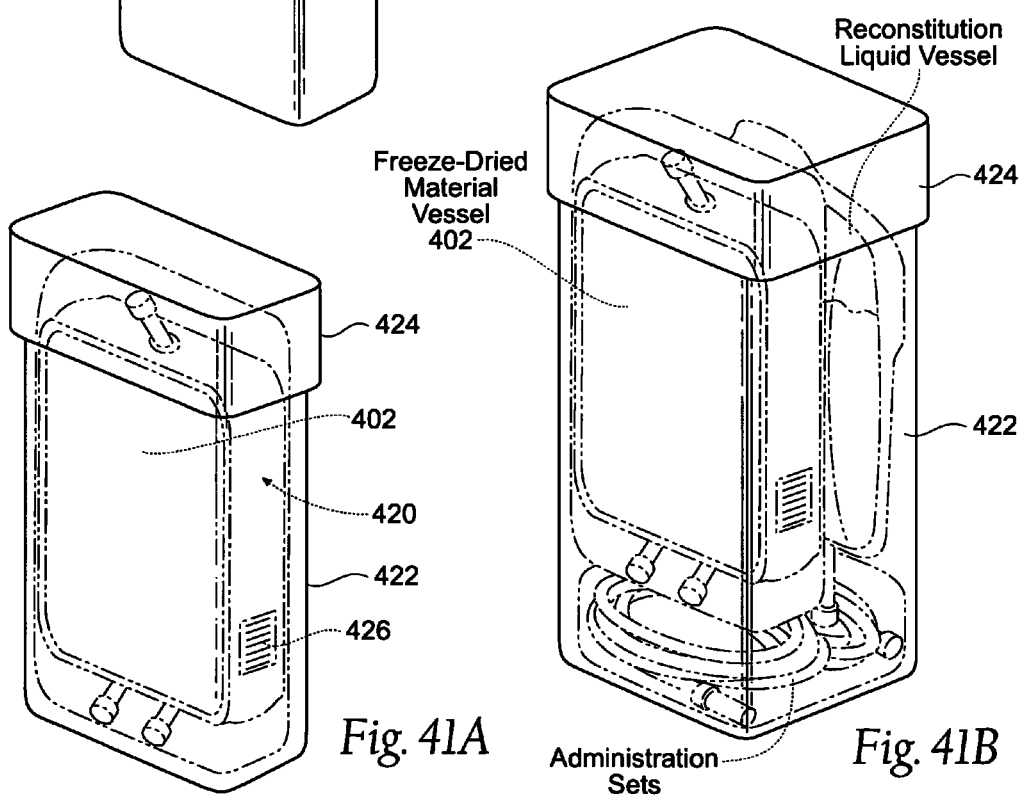
FIG. 41B shows a perspective view of a freeze-dried material storage assembly sealed within a gas-impermeable overwrap, and placed in a rigid outer container with a lid, as FIG. 41 shows, with the outer container also including storage space for a vessel of reconstitution liquid and associated reconstitution and administration sets.

The freeze-dried material storage assembly 420 can be further protected during transportation and storage by placement within a rigid outer container or can 422 as shown in FIGS. 40 and 41A. The outer container 422 may comprise, e.g., of metal or high impact plastic material. The outer container 422 provides further protection against tearing, puncturing, or collapse of the overwrap 418 and vessel 402 during subsequent handling and storage. As FIG. 41B shows, the outer container 422 can, if desired, include additional compartments to hold, along with the freeze-dried material vessel 402, a vessel filled with a reconstitution liquid, as well as associated reconstitution and administration sets.

In the illustrated embodiment (as shown in FIG. 41A), the outer container 422 includes a lid 424 that closes and, desirably, seals the container 422. The lid 424 can be removed to provide access to the vessel 402 and overwrap 418 at the instance of use.

Figure 42:
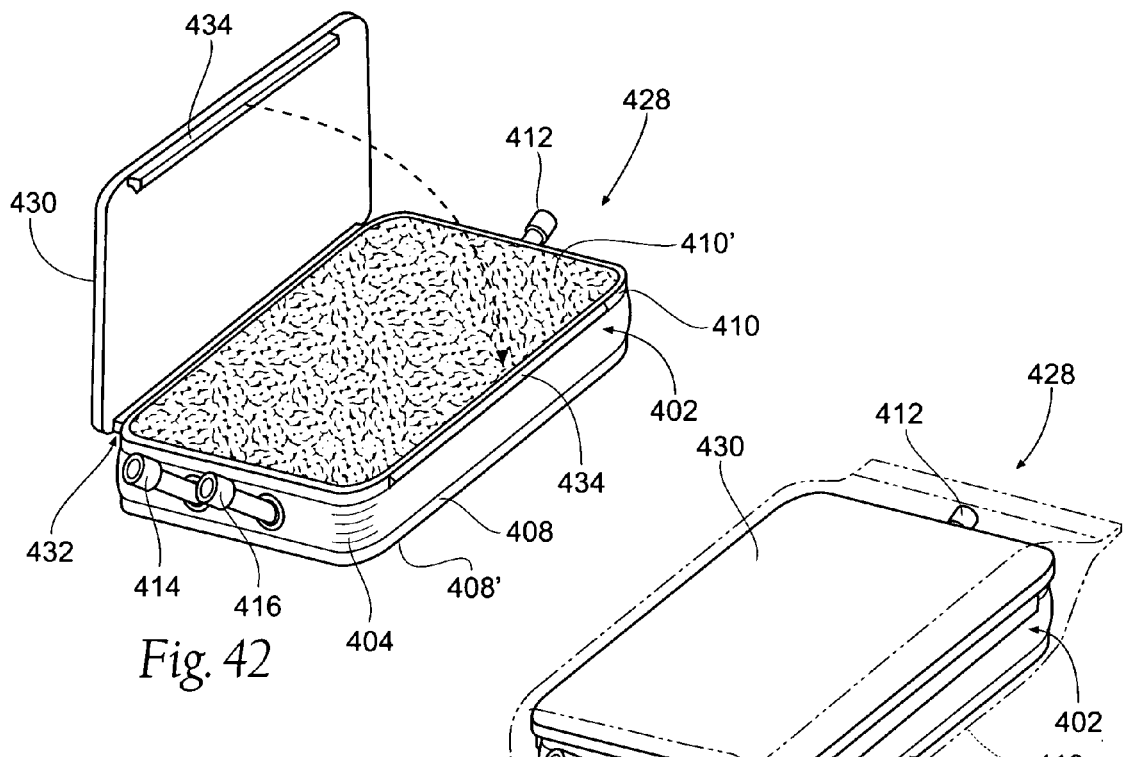
FIGS. 42 and 43 are perspective views of a unitary freeze-died material storage assembly comprising a vessel as shown in FIGS. 39A to 39D and an integral closure cover, FIG. 42 showing the closure cover in an opened condition, and FIG. 43 showing the closure cover in a closed condition.
Figure 43:
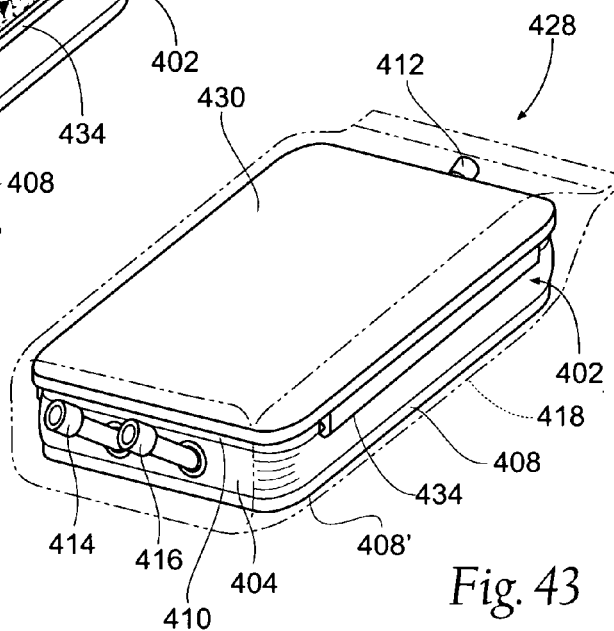

If desired (as shown in FIGS. 42 and 43), one or more integrity marker elements 426 can be placed within or on the interior of the overwrap 418. The integrity marker elements 426 carry a material sensitive to the presence of oxygen and/or moisture, or combinations thereof, and/or other preselected conditions adverse to or possibly adverse to the integrity or efficacy of the freeze-dried material. For example, the sensitive material can change color to visibly indicate through the overwrap 418 when a predetermined threshold level of oxygen and/or moisture, or combination thereof, exists within the overwrap 418. The markers 426 provide further visual indications of the integrity and efficacy of the freeze-dried material within the freeze-dried material storage assembly 420 prior to reconstitution.

D. Unitary Freeze-Dried Material Storage Assemblies

FIGS. 42 and 43 show a representative embodiment of a unitary freeze-dried material storage assembly 428. In this representative embodiment, the vessel 402 as above described and shown in FIGS. 39A to 39D further includes a pivotally mounted closure cover 430. The closure cover 430 is made from a gas-impermeable material, e.g. polyvinyl chloride, or polyethylene, or polypropylene, or high density polyethylene. Such materials may be used in combination with metallized, reduced gas-permeability coatings, or metal laminates.

In the illustrated embodiment, the closure cover 430 is made from a generally rigid material. In this arrangement, a hinge assembly 432 on the frame defined by the second end component 410 couples the closure cover 430 on the vessel 402 for movement between an opened condition, as shown in FIG. 42, and a closed condition, as shown in FIG. 43.

In the opened condition (shown in FIG. 42), the closure cover 430 is spaced away from the gas permeable material 410' of the second end component 410, permitting unrestricted gas transmission through the gas permeable material 410' of the second end component 410 for the purposes previously described.

In the closed condition (shown in FIG. 43), the closure cover 430 covers the entirety of the gas permeable material 410' of the second end component 410, substantially blocking gas transmission through it.

Desirably, the edges of the closure cover 430 and frame defined by side end component 410 are sized and configured, e.g., by interference fit and/or by use of gasket assembly, to form a gas-impermeable seal assembly about the entirety of the gas permeable material 410' of the second end component 410 when the closure cover 430 is in the closed condition. If a vapor barrier overwrap is to be used, the seal assembly need not be "air tight" or aseptic, but instead provide sufficient gas holding capacity to accommodate handling in the time period between removal from the freeze dryer and the application of the vapor barrier overwrap.

Desirably, a latch assembly 434 on the closure cover 430 and the second end component 410 forms a lock when the closure cover 430 is in the closed condition, resisting inadvertent opening the closure cover 430.

Alternatively, the closure cover 430 can comprise a more flexible material attached to the frame defined by the second end component 410, which is normally rolled or folded away from the gas permeable material 410' of the second end component 410 (i.e., the opened condition). In this arrangement, the more flexible closure cover 430 is unrolled or unfolded and drawn over the gas permeable material 410' of the second end component 410 (i.e., the closed condition). The more flexible closure cover 430 is then peripherally sealed about the gas permeable material 410' of the second end component 410, e.g., by heat sealing.

In the arrangement shown in FIGS. 43 and 43, the unitary freeze-dried material storage assembly 428 undergoes the freeze-drying process in the orientation shown in FIG. 42, with the gas permeable material 410' of the second end component 410 facing upward, and the closure cover 430 being in the opened condition (this is also shown in FIG. 52). In this orientation, during drying, water vapor will sublimate and escape upward from the material within the vessel 402 through the gas permeable gas permeable material 410' of the second end component 410.

As previously described, after drying, a blanket of oxygen-free inert gas may, if desired, be introduced over the unitary freeze-dried material storage assembly 428 in the orientation shown in FIG. 42. The oxygen-free inert gas enters the interior space 406 through the gas permeable gas permeable material 410' of the second end component 410, to infiltrate and exclude moisture and oxygen in the interior space 406, as previously described.

In this arrangement, while the unitary freeze-dried material storage assembly 428 (now containing the freeze-dried material) is maintained under the blanket of the oxygen-free inert gas, the closure cover 430 is placed into its closed condition (see FIG. 54), and the latch assembly 434 is engaged, as shown in FIG. 43. The closure cover 430 traps the oxygen-free gas environment within the unitary freeze-dried material storage assembly 428 during subsequent transportation and storage. As before described, the exclusion of moisture and oxygen in the presence of the oxygen-free inert gas trapped within the unitary freeze-dried material storage assembly 428 prevents degradation of the freeze-dried material carried within the vessel 402 during subsequent transport and storage.

Figure 44:
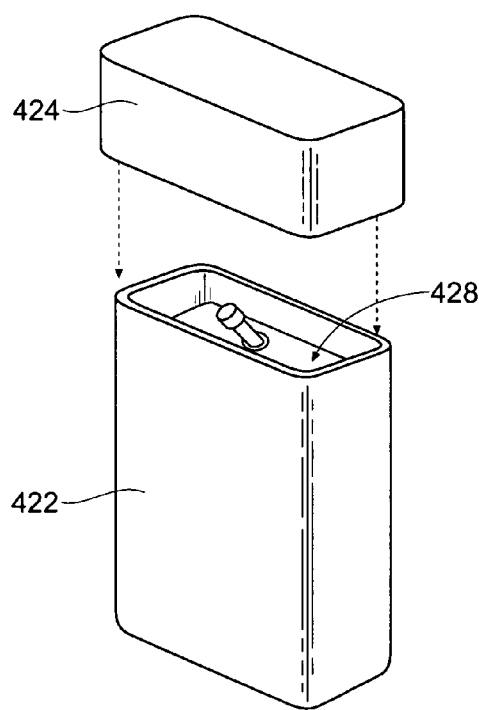
FIGS. 44 and 45 are perspective views of the unitary freeze-dried material storage assembly shown in FIG. 43 (with the closure cover in the closed condition) placed within a rigid outer container with a lid for enclosing the unitary freeze-dried material storage assembly during transport and storage until the instance of use.
Figure 45:
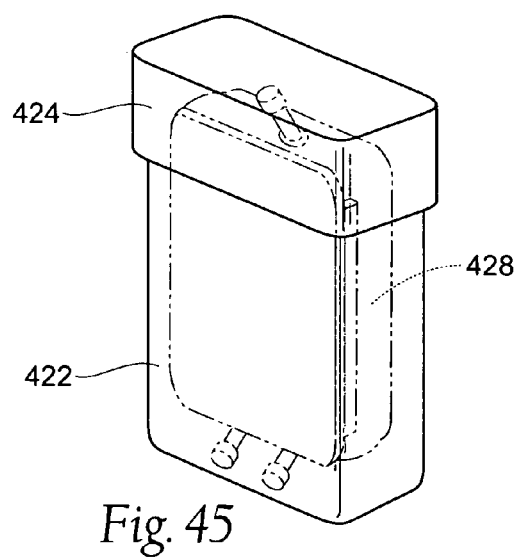

As shown in FIGS. 44 and 45, the unitary freeze-dried material storage assembly 428 can be placed within a rigid outer container or can 422 with a lid 424, as previously described, made e.g., of metal or high impact plastic material. The outer container 422 provides further protection against tearing, puncturing, or collapse of the unitary freeze-dried material storage assembly 428 during subsequent handling and storage. As earlier described, if desired, the outer container 422 can include one or more separate compartments to hold a vessel containing a reconstitution liquid, as well as associated reconstitution and administration sets.

If desired, the unitary freeze-dried material storage assembly 428 shown in FIG. 43 can also be placed a vacuum sealed, transparent gas-impermeable vapor barrier or overwrap 418, of the type shown in FIG. 40, prior to placement in the rigid outer container. The optional overwrap 418 is shown in phantom lines in FIG. 43.

FIGS. 46 and 47 show an alternative representative embodiment of a unitary freeze-dried material storage assembly 428. In this representative embodiment, the vessel 402 as above described and shown in FIGS. 39A to 39D includes a region of gas permeable material 436 that does not extend over the entire area of the second end component 410. In this arrangement, the remaining region 438 of the second end component 410 comprises a gas-impermeable material, examples of which have already been described.

As shown in FIG. 46, the region of gas permeable material 436 is supported by and sealed to a frame 440, which is itself joined to the second end component 410. The sealing can be accomplished, e.g., by adhesives or heat.

As FIG. 46 shows, the frame 440 rises slightly above the plane of the remainder 438 of the second end component 410. Stand-offs 442 extend from the frame 440 into the vessel 402, to moderate inward flexure of the frame 440 relative to the second end component 410, e.g., when closing the closure cover 430, as will be described. Upon an initial amount of inward flexure of the frame 440 under such conditions, the stand-offs 442 will move into contact with the first end component 408 and will thereby resist further inward flexure.

In this arrangement, the frame 440 carries a pivotally mounted closure cover 430. The closure cover 430 is made from a gas-impermeable material, e.g. polyvinyl chloride, or polyethylene, or polypropylene, or high density polyethylene. Such materials may be used in combination with metallized, reduced gas-permeability coatings, or metal laminates.

In the illustrated embodiment, the closure cover 430 is made from a generally rigid material. In this arrangement, A hinge assembly 432 on the frame 440 couples the closure cover 430 for movement between an opened condition, as shown in FIG. 46, and a closed condition, as shown in FIG. 47.

In the opened condition (shown in FIG. 46), the closure cover 430 is spaced away from the region of gas permeable material 436 carried by the frame 440, permitting unrestricted gas transmission through the region of gas permeable material 436 during and after the freeze-drying process for the purposes previously described.

In the closed condition (shown in FIG. 47), the closure cover 430 covers the entirety of the region of gas permeable material 436 carried by the frame 440, substantially blocking gas transmission through it.

Desirably, the edges of the closure cover 430 and the frame 440 are sized and configured, e.g., by interference fit and/or by use of gasket assembly, to form a gas-impermeable seal about the entirety of the frame 440 when the closure cover 430 is in the closed condition. If a vapor barrier overwrap is to be used, the seal need not be "air tight" or aseptic, but instead provide sufficient gas holding capacity to accommodate handling in the time period between removal from the freeze dryer and the application of the vapor barrier overwrap.

Desirably, a latch assembly 434 on the closure cover 430 and the frame 440 forms a lock when the closure cover 430 is in the closed condition, resisting inadvertent opening the closure cover 430.

Alternatively, the closure cover 430 can comprise a more flexible material attached to the frame 440, which is normally rolled or folded away from the gas permeable second end component 410 on the frame 440 (i.e., the opened condition). In this arrangement, the more flexible closure cover 430 is unrolled or unfolded and drawn over the gas permeable second end component 410 on the frame 440 (i.e., the closed condition). The more flexible closure cover 430 is then peripherally sealed about the frame, to cover the gas permeable second end component 410, e.g., by heat sealing.

In the arrangement shown in FIGS. 46 and 47, the unitary freeze-dried material storage assembly 428 undergoes the freeze-drying process in the orientation shown in FIG. 46, with the region of gas permeable material 436 carried by the frame 440 facing upward and the closure cover 430 in the opened condition. In this orientation, during drying, water vapor will sublimate and escape upward from the material through the region of gas permeable material 436 carried by the frame 440. As previously described, after drying, a blanket of oxygen-free inert gas is introduced over the unitary freeze-dried material storage assembly 428 while maintained the orientation shown in FIG. 46. The oxygen-free inert gas enters the interior space 406 through the region of gas permeable material carried by the frame 440, to infiltrate and exclude moisture and oxygen in the interior space 406, as previously described.

In this arrangement, while the unitary freeze-dried material storage assembly 428 (now containing the freeze-dried material) is maintained under the blanket of the oxygen-free inert gas, the closure cover 430 is placed into its closed condition and the latch assembly 434 engaged, as shown in FIG. 47. The closure cover 430 traps the oxygen-free gas environment within the unitary freeze-dried material storage assembly 428 during subsequent transportation and storage. As before described, the exclusion of moisture and oxygen in the presence of the oxygen-free inert gas trapped within the unitary freeze-dried material storage assembly 428 prevents degradation of the freeze-dried material carried within the vessel 402 during subsequent transport and storage.

As shown in FIGS. 48 and 49, the unitary freeze-dried material storage assembly 428 can be placed within a rigid outer container or can 422 with a lid 424, as previously described, made e.g., of metal or high impact plastic material. The outer container 422 provides further protection against tearing, puncturing, or collapse of the unitary freeze-dried material storage assembly 428 during subsequent handling and storage.

If desired, the unitary freeze-dried material storage assembly 428 shown in FIG. 43 can also be placed a vacuum sealed, transparent gas-impermeable overwrap 418, of the type shown in FIG. 40, prior to placement in the rigid outer container. The optional overwrap 418 is shown in phantom lines in FIG. 47.

E. Using the Unitary Freeze-Dried Material Storage Assemblies

1. Freeze-Drying a Material within a Freeze-Dried Material Storage Assembly

In a representative embodiment, the freeze-dried material comprises plasma. A description of an illustrative way of preparing freeze-dried plasma for packaging in a representative freeze-dried material storage assembly as disclosed in FIGS. 42 and 43 therefore follows.

Preparation and manufacturing of the plasma will take place in an aseptic, clean room setting. The manufacturing and preparation procedures can be done, for example, in an ISO Class 5 clean room (or better) with ISO Class 3 biocontainment hoods for aseptic handling of human plasma. Freeze drying can be done aseptically in a CIP/SIP freeze dryer.

Human plasma is collected from a single donor in a conventional way, e.g., by collecting a unit of whole blood from the donor in a closed system collection bag, followed by centrifugal separation of the plasma and its collection in an integrally connected transfer bag 444 (containing one plasma unit of about 250 ml). Each unit (contained in the transfer bag 444) will be handled individually in the bio-containment hood. Between handling one single donor unit and another unit single donor unit from a different donor, there will be a line clearance protocol for change-over in the bio-containment hood, or a validation process for flow design and change-over can be otherwise provided. This protocol may address removal of all tools and materials associated with the previous handling. It may also address the thorough wash down of the containment work area and work area instruments (mass balances) to ensure no residues of the previous handling were left in place. The identification of single donor samples will be maintained by bar coding and other tagging of the single donor human plasma containers.

The freeze-dried material storage assembly 428 is subjected to a pre-processing protocol to provide a sterile, pyrogen free assembly. A representative size for the assembly 420 for freeze-drying about 250 ml of plasma is about 10 cm×12 cm×2 cm (l×w×d).

As shown in FIG. 50, the 250 ml human plasma unit is dispensed from the transfer bag 444 into the freeze-dried material storage assembly 428. Flexible medical grade tubing 446 coupled integrally to the transfer bag 444 is coupled to the first port component 412 in an aseptic manner, e.g., using known aseptic coupling techniques well know in blood component processing or a spike or a leur fitting coupling under aseptic conditions. The plasma can be transferred from the transfer bag 444 into the freeze-dried material storage assembly 428 through the tubing 446 and the first port component 412 by gravity flow.

As shown in FIG. 51, the transfer tubing 446 is then disconnected in an aseptic fashion either under the conditions described above or using, e.g., a Hematron® Dielectric Sealer to provide snap-apart aseptic seals well known in blood component processing.

Bar coding and tagging 448 is applied to freeze-dried material storage assembly 428. The bar coding and tagging 448 reflects the human plasma identification 450 carried by the transfer bag 444 (source, blood type, date of collection, etc.).

As shown in FIG. 52, the freeze-dried material storage assembly 428 (now containing the liquid plasma) is then placed inside a freeze dryer 452 on an aseptic freeze dryer shelf surface 454. The freeze dryer 452 used for the lyophilization is desirably a validated clean in place, steam in place freeze dryer.

As shown in FIG. 52, the freeze-dried material storage assembly 428 is oriented with the gas permeable material 410' of the second end component 410 facing upward, and the closure cover 430 placed in the opened condition.

Once loaded, the freeze dryer cycle (controlled by a processor 456) is started. This cycle generally cools the human plasma to near −45° C. and freezing for 2 to 8 hours, followed by cooling of the freeze dryer condenser and application of vacuum to start the freeze drying cycle. A freeze-dried human plasma cake is formed within the freeze-dried material storage assembly 428.

In the primary freeze drying cycle, the temperature of the human plasma cake needs to remain below −33° C. (the collapse temperature) to maintain its integrity. When the moisture content of the cake is below 5% weight per weight (w/w), a secondary drying cycle (the elevated temperature) is used to further lower the moisture content. Generally the combined primary and secondary freeze drying cycles will take at least 72 hours. As before described, in the orientation shown in FIG. 52, during the drying cycle, sublimating water vapor will escape upward from the frozen plasma material through the gas permeable material 410' of the second end component 410, unrestricted by the opened closure cover 430.

The flexible side wall component 404 accommodates flexure of the vessel due to pressure conditions encountered during the freeze drying cycle.

At the conclusion of the freeze drying cycle (see FIG. 53), the freeze dryer vacuum is opened (by operation of the controller 456) to an atmosphere 458 of an oxygen-free, high purity inert gas such as nitrogen or argon. As before described, the blanket of oxygen-free inert gas enters the interior space of the freeze-dried material storage assembly 428 through the gas permeable material 410' of the second end component 410, unrestricted by the opened closure cover 430, to infiltrate and exclude moisture and oxygen in the interior space, as previously described.

Figure 54:
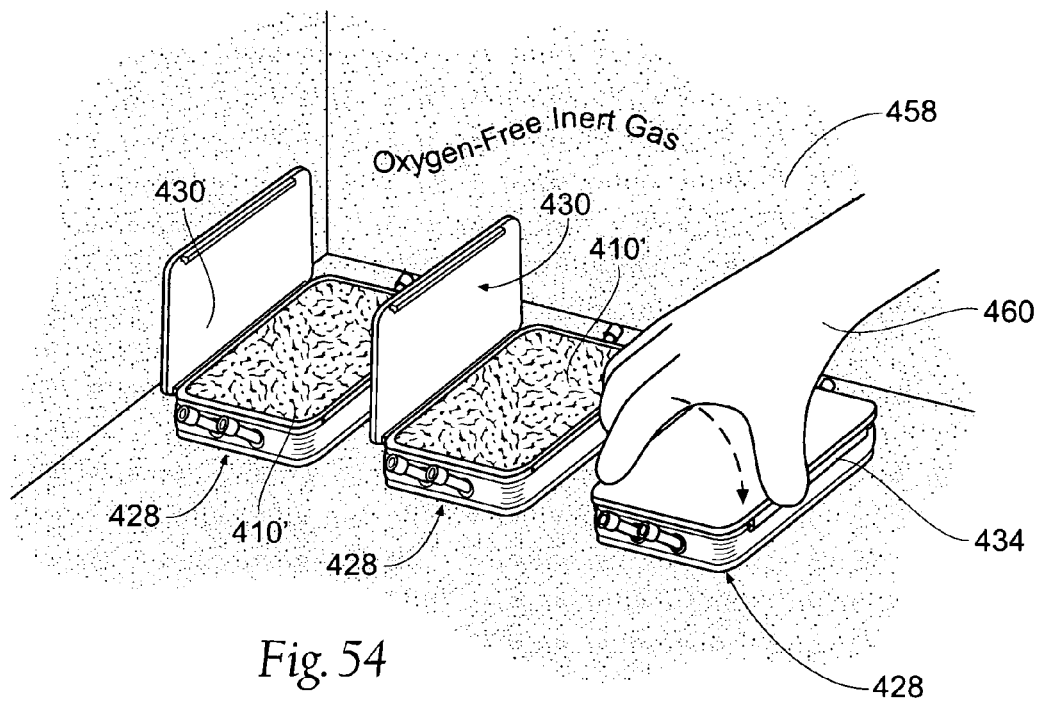
FIG. 54 is a perspective view of the several unitary freeze-dried material storage assemblies within the freeze dryer shown in FIG. 53, with the closure covers being placed into the closed condition to trap the oxygen-free inert gas within the unitary freeze-dried material storage assemblies, to protect the freeze-dried plasma material from degradation during subsequent transport and storage.

As shown in FIG. 54, while the unitary freeze-dried material storage assembly 428 (now containing the freeze-dried material) is maintained under the blanket of the oxygen-free inert gas, the closure cover 430 is placed into its closed condition and the latch assembly 434 engaged.

Figure 53:
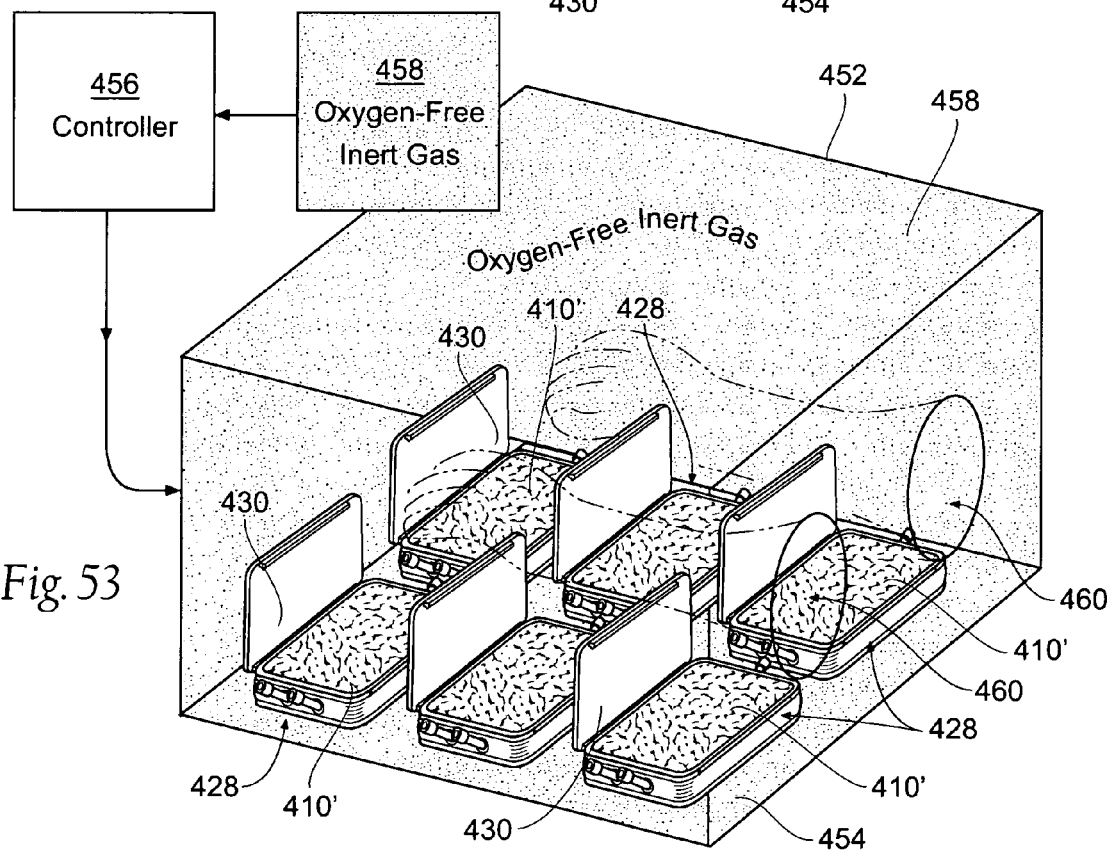
FIG. 53 is a perspective view of the several unitary freeze-dried material storage assemblies within the freeze dryer shown in FIG. 52, with the closure covers still in the opened condition, the freeze dryer exposing the unitary freeze-dried material storage assemblies to a blanket of oxygen-free inert gas, the open closure covers accommodating infiltration of the oxygen-free inert gas into the freeze-dried plasma material contained within the assemblies.

In a representative embodiment shown in FIGS. 52 and 53, the freeze-dryer 452 includes means 460 for providing aseptic access into the freeze-dryer 452, so that the closure cover 430 can be manually closed, as FIG. 54 shows. Alternatively, the means 460 can comprise remotely actuated mechanical or robotic means within the freeze dryer, to close the closure covers 430 of the unitary freeze-dried material storage assemblies 428.

Still alternatively, the freeze-dried material storage assemblies 428 can removed to an aseptic containment area or cart (e.g., as generally shown FIG. 17D) having a contained environment maintained under an oxygen-free inert gas blanket to exclude moisture and oxygen. The containment area or cart may couple to the front of the freeze dryer to allow for transfer of the freeze dryer contents under a controlled inert gas blanket. The closure covers 430 of the freeze-dried material storage assemblies 428 can be closed within the environment provided by the aseptic container area or cart.

It should be appreciated that, instead of providing a unitary closure cover 430, or in combination with a unitary closure cover 430, a vacuum sealed, transparent overwrap 418, as shown in FIG. 40, made from a gas-impermeable material can be placed over the vessel 402 in the presence of an oxygen-free inert gas environment.

Regardless, the closure cover 430 and/or overwrap 418 traps the oxygen-free inert gas environment within the unitary freeze-dried material storage assembly 428 (or a vessel 402 with an overwrap 418) during subsequent transportation and storage. As before described, the exclusion of moisture and oxygen in the presence of the oxygen-free inert gas trapped within the unitary freeze-dried material storage assembly 428 prevents degradation of the freeze-dried material carried within the vessel 402 during subsequent transport and storage.

Figure 55:
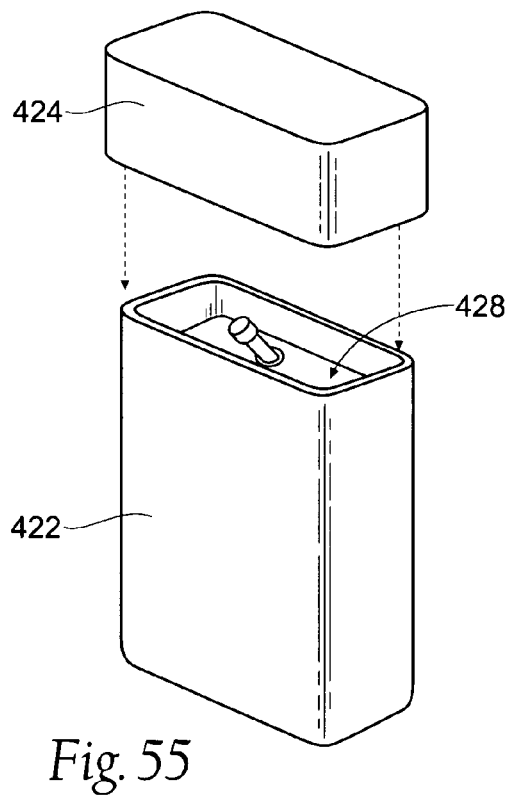
FIGS. 55 and 56 are perspective views of the unitary freeze-dried material storage assembly shown in FIG. 54 (with the closure cover in the closed condition) placed within a rigid outer container with a lid for enclosing the unitary freeze-dried material storage assembly during transport and storage until the instance of use.
Figure 56:
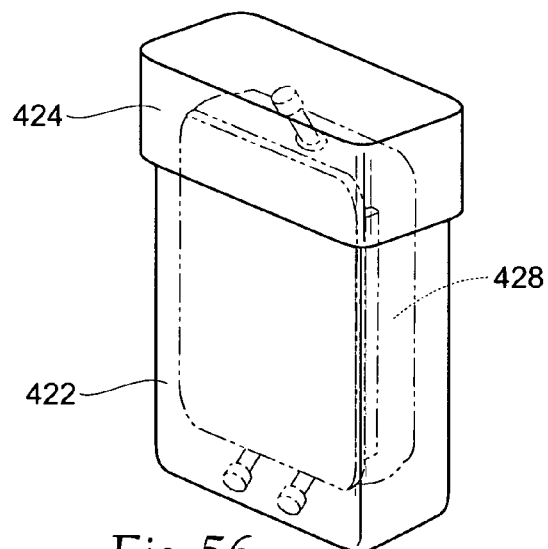

As shown in FIGS. 55 and 56, the closed unitary freeze-dried material storage assembly 428 (with or without an overwrap 418) can be placed within a rigid outer container or can 422 with a lid 424, as previously described, made e.g., of metal or high impact plastic material. The outer container 422 provides further protection against tearing, puncturing, or collapse of the unitary freeze-dried material storage assembly 428 during subsequent handling and storage.

2. Reconstituting and Administering Freeze-Dried Plasma from a Unitary Freeze-Dried Material Storage Assembly In use at a remote site (see FIG. 57), the freeze dried material storage assembly 428 (or vessel 402 with overwrap 418, as shown in FIGS. 40 and 41) is removed from the outer container 422. After removal of the overwrap 418 (if provided), a transfer set 462 is coupled to a container 464 of sterile reconstituting liquid (e.g., water) and the second port component 414 of the respective unitary freeze-dried material storage assembly 428 (or vessel 402). The transfer set 462 can include plastic needles or spikes at each end to make the coupling, e.g., as shown in FIG. 30. The transfer set 462 may be long and flexible (as shown in FIG. 57). Alternatively, the transfer set 462 can be short and rigid, to reduce storage space and simplify handling.

Figure 59:
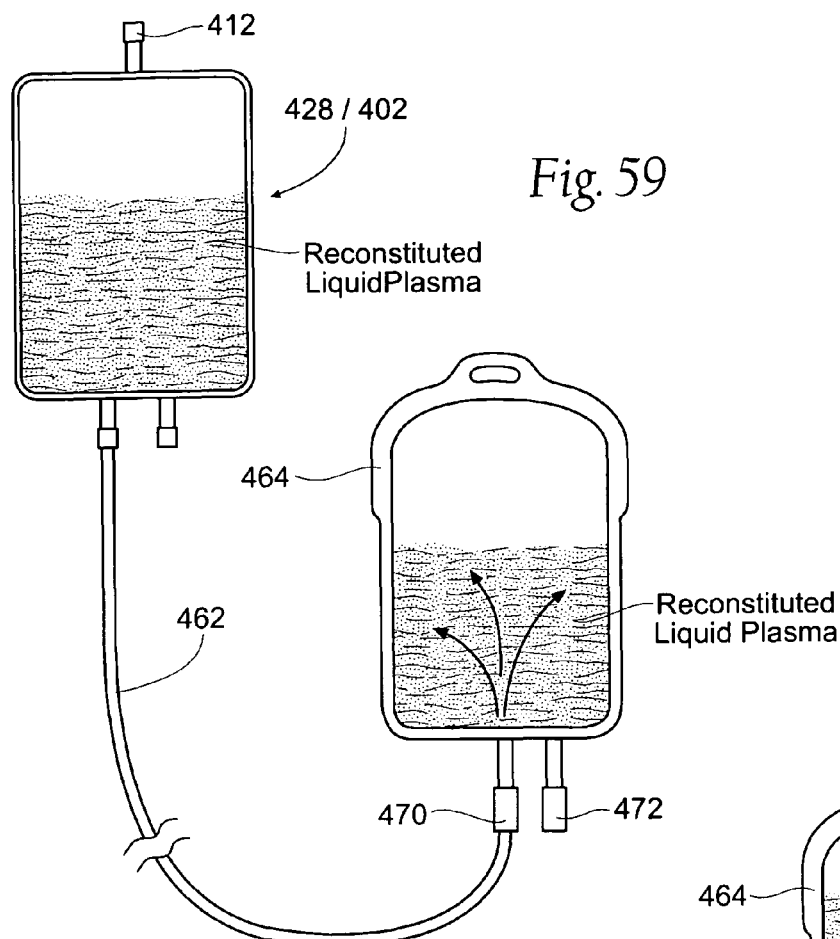
FIG. 59 shows the mixing of freeze-dried plasma material with a reconstituting liquid, after transferring a reconstituting liquid into the unitary freeze-dried material storage assembly as shown in FIG. 57, by transferring the mixture of reconstituting liquid and freeze-dried plasma material back to the source container, the mixture being transferred back and forth in the manner shown in FIGS. 57 and 59 until ready for administration.

The caregiver can now proceed to manipulate the freeze dried material storage assembly 428 (or vessel 402), together with the container 464 of reconstituting liquid to transfer the reconstituting liquid from the container 464 into contact with the freeze-dried material within the freeze dried material storage assembly 428, as FIGS. 57 and 59 shows. The caregiver can create a fluid pressure differential across the transfer set 462 by selectively establishing head height differentials. Fluid can be expelled in response to the fluid pressure differential through the transfer set 462 back and forth the between the freeze dried material storage assembly 428 (or vessel 402) and the container 464 of reconstituting liquid 206, as necessary to reconstitute the freeze-dried material, in preparation for administration to an individual.

Figure 32:
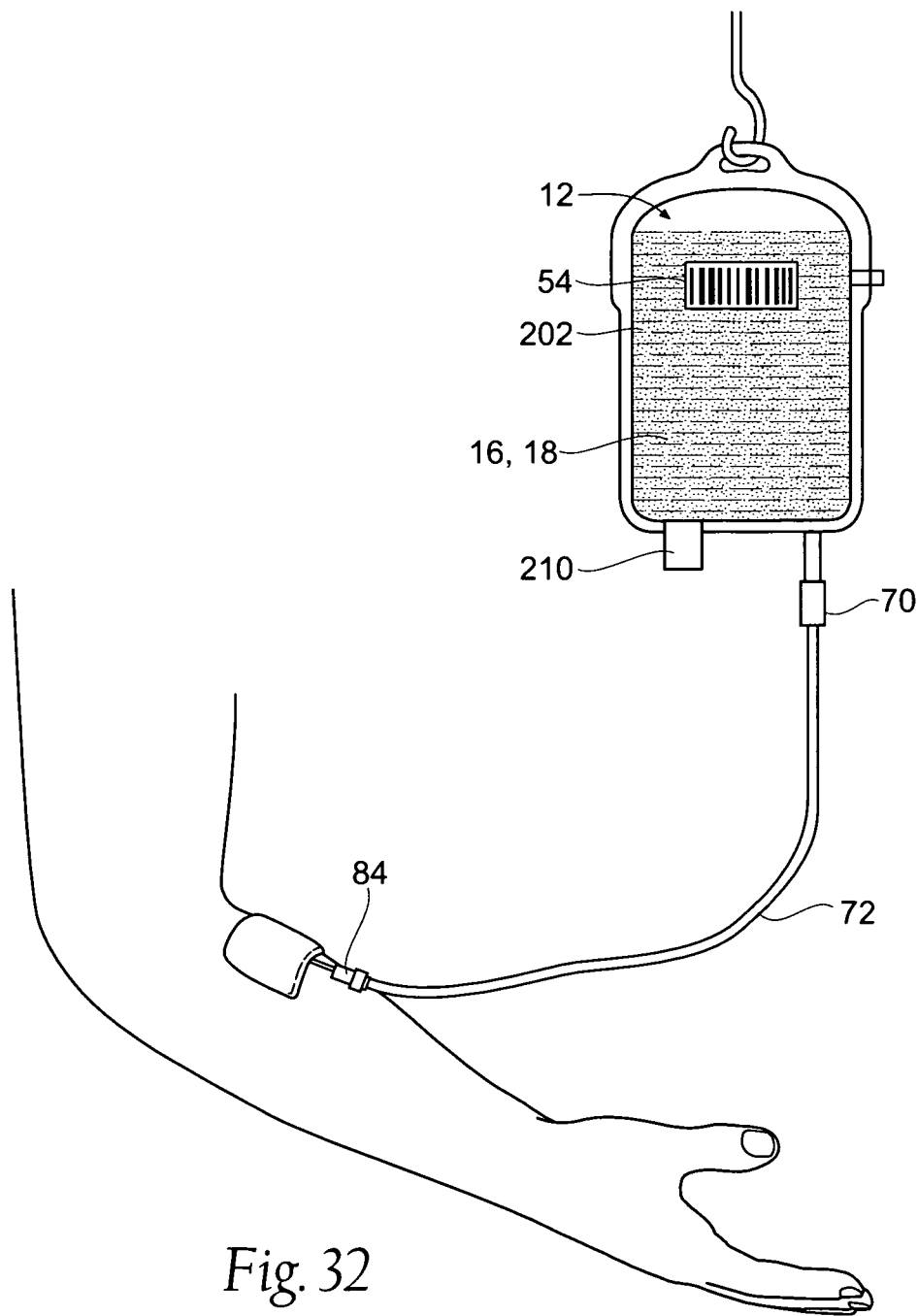
FIG. 32 is a front elevation view of one of the containers of the system shown in FIGS. 30 and 31, after the freeze-dried material has been reconstituted, showing the administration of reconstituted material directly from the container to a recipient.

In the embodiment shown in FIG. 58, the reconstituted material is administered from the freeze dried material storage assembly 428 (or vessel 402). In this arrangement, the administration set 462 used for mixing is uncoupled from the second port component 414, and the second port component 414 is closed (as before described, the second port component 414 can include a septum that automatically closes upon the removal of the transfer spike or needle). At this time, as shown in FIG. 58, the caregiver couples the third port component 416 to an administration set 466, for transfer of the reconstituted material into the circulatory system of an individual, as shown in FIG. 58. The administration set 466 includes a phlebotomy needle 468 for insertion into a vein, in the same manner as before described with reference to FIG. 16 or 32. The flexible side wall component 404 accommodates the collapse of the vessel 402 as the reconstituted material is administered into the circulatory system of an individual.

Figure 60:
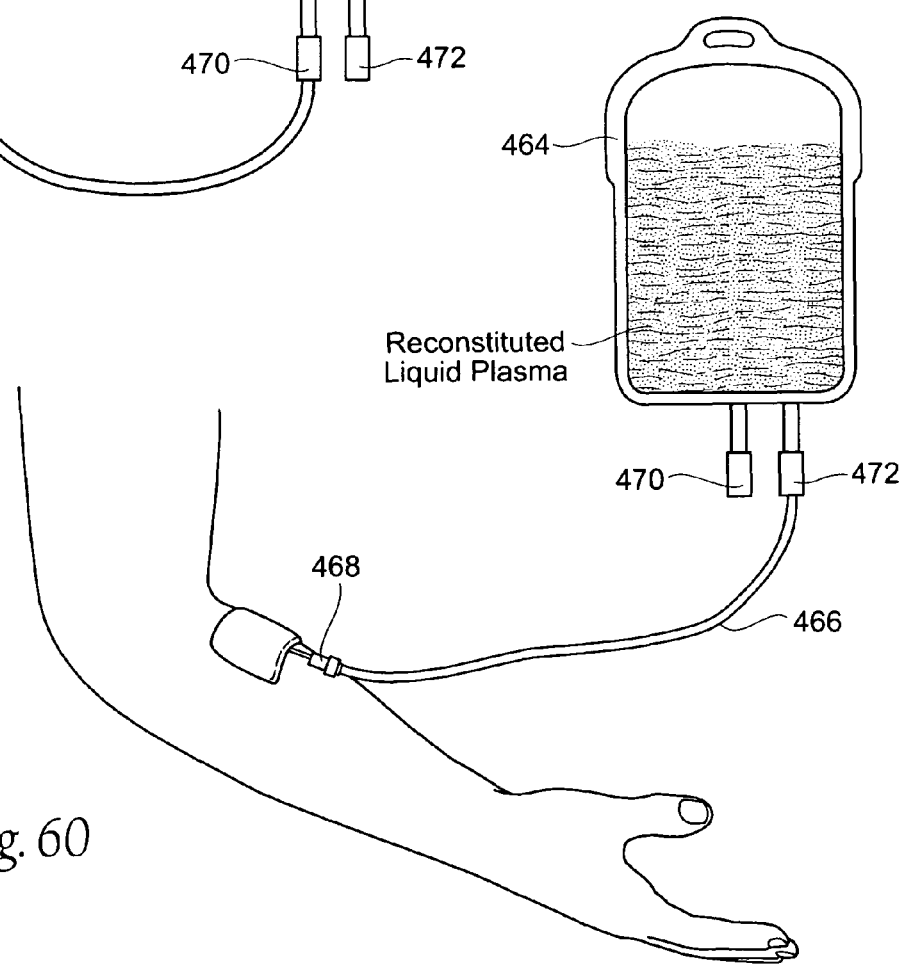
FIG. 60 shows the administration to an individual of freeze-died plasma material reconstituted using a unitary freeze-dried material storage assembly as shown in FIG. 57, the reconstituted material being ultimately transferred after mixing as shown in FIGS. 57 and 59 out of the unitary freeze-dried material storage assembly into the original reconstituting liquid container for administration.

In the embodiment shown in FIG. 60, the reconstituted material is administered from the container 464 that initial contained the reconstituting liquid. In this arrangement, after mixing, the reconstituted material is finally transferred from freeze dried material storage assembly 428 (or vessel 402) to the reconstituting liquid container 464. In this arrangement, the administration set 462 used for mixing is uncoupled from the reconstituting liquid container 464, and the associated port 470 closed. At this time, as shown in FIG. 60, the caregiver couples another port 472 on the reconstituting liquid container 464 to an administration set 466, for transfer of the reconstituted material to the circulatory system of an individual, as shown in FIG. 60. The administration set 466 includes a phlebotomy needle 468 for insertion into a vein, in the same manner as before described with reference to FIG. 16 or 32.

VII. Further Embodiment of a Device and System for Freeze-Drying, Storing, and Administering Plasma FIGS. 61-71 depict an alternate embodiment of a freeze-drying container and process, that allows freeze-drying of liquid plasma directly in the container that will be used to transfer the reconstituted plasma to a patient, without the container being placed within a vapor permeable bag or membrane during the freeze-drying process. That is, the container that contains the plasma is in communication with a vapor permeable membrane during the freeze-drying process, but is not required to be placed within a vapor permeable bag during the freeze-drying process.

Many freeze drying plasma processes require placing plasma within a lyophilization unit, normally with the plasma in a first container, and then placing that first container within a vapor permeable bag, made of a microporous PTFE or HDPE membrane. After freeze-drying, the vapor permeable membrane bag is discarded and the freeze-dried plasma is transferred to a container that can be used by an end user, such as a medic, with such a container preferably being of a likeness to blood bags normally used by medics and the like. An issue with such a process is that the expansion of the vapor permeable bag may cause the permeable bag to pull away from the heat transfer surface during lyophilization, which could result in less than optimal freeze-drying. The process described below can minimize such an issue.

FIG. 61 depicts a system 500 for freeze-drying, storing and delivering plasma to a patient, without the need to transfer the freeze-dried plasma to another container or system. The system 500 generally comprises a first collapsible container 502 and a second container 504 that contains a membrane material 506 that would typically be manufactured using microporous PTFE membrane material (e.g. Gore-Tex™) or microporous HDPE membranes (e.g. Tyvek™). The second container 502 may or may not be collapsible. The first container 502 and the second container 504 are connected by tubing 508 having an open first end 510, with the tubing 508 allowing vapors to be transferred from the first container 502 to the second container 504 during the freeze-drying process. The tubing 508 can be of any diameter, but preferably has a diameter of approximately 1-2 cm. The tubing 508 can also be any length, but should be sufficiently long so that the tubing 508 can be pinched, closed, sealed, and severed, as will be discussed below with respect to FIGS. 66A-69.

Still referring to FIG. 61, the second collapsible container 504 also has an opening 512, which receives the open first end 510. Normally, the system 500 is provided in an assembled device, and it is preferred that the system 500 is provided as an assembled device, most specifically for sterility issues. However, if assembly is necessary, it is preferable that a heat seal will be applied to the second collapsible container 504 so that the opening 512 is sealed around the open first end 510, providing the assembled system 500 shown in FIG. 63. It should be noted that the tubing 508 will then provide an open vapor or gas pathway 514 from the first collapsible container 502 to the second collapsible container 504. The tubing 508 may be integrally formed with the first container 502, or be a separate element that would be connected to the first container 502, similarly to how the second container 504 is connected to the tubing 508.

FIG. 62 depicts an empty assembly 500. Due to carbonate removal during the freeze-drying process, generally in the form of carbon dioxide ($CO_2$), the pH of the eventual reconstituted plasma is elevated, i.e. higher than desired. Thus, the pH within the assembly 500 may need to be adjusted, either by adding a pH adjustment solution prior to adding plasma to the first container 502, or backfilling $CO_2$ during lyophilization. FIG. 62 demonstrates a pH adjustment solution being introduced to the assembly 500 prior to the addition of plasma. An aseptic adjustment solution port 515, preferably a spike connection, located on the first container 502, allows the aseptic addition of a pH adjustment solution. Preferable adjustment solutions include acids (ascorbic acid, etc.) or a buffer solution. Once the desired amount of buffer solution is added to the assembly, the solution port 515 will be sealed shut, preferably with the solution port 515 being heat sealed.

FIG. 63 depicts the assembly 500 after the adjustment solution has been added to the first container 502. As stated, the solution port 515 is sealed shut. Liquid plasma is then added to the first container 502 by way of an aseptic plasma addition port 517. Once a predetermined volume or weight of plasma has been added to the first container 502, the port 517 will be closed and sealed, preferably heat sealed.

Figure 64:
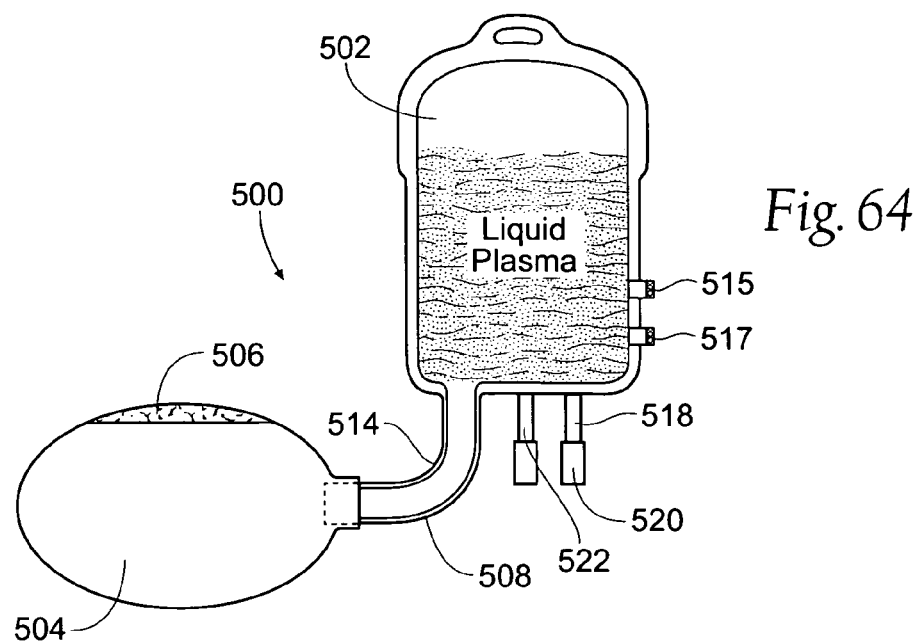
FIG. 64 is a front elevation view of the system and device of FIG. 61, with the device being filled with plasma.
Figure 65:
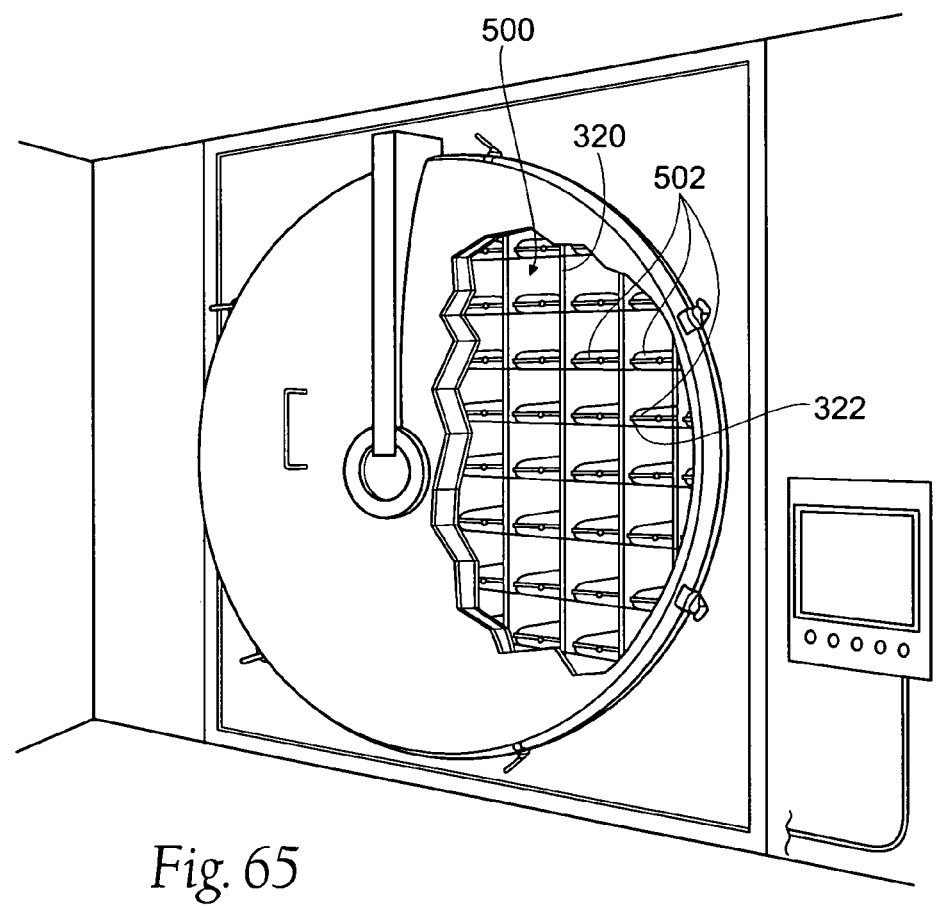
FIG. 65 is a perspective view of several devices shown in FIG. 64 after placement in a freeze-dryer for the purpose of freeze-drying liquid plasma in situ within each of the devices, with the primary portion (the first collapsible container) being in contact with the heat transfer surface of the freeze-dryer.
Figure 69:
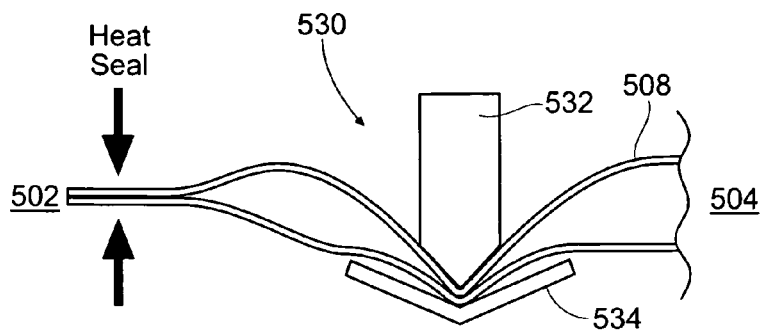
FIG. 69 depicts the tubing, used to connect the first and second containers, being heat sealed to seal shut the first container.

FIG. 64 displays the assembly 500, filled with liquid plasma, with the ports 515 and 517 sealed Once the first collapsible container 502 is filled with a predetermined amount of liquid plasma 16, the system 500 will be subjected to the freeze-drying process. As shown in FIG. 65, one or more devices 500, with each first collapsible container 502 filled with liquid plasma, is placed inside a freeze dryer 320 on an aseptic freeze dryer shelf surfaces 322. The assembly 500 is placed within a reusable stoppering mechanism, discussed further with respect to FIGS. 66A-69B, that allows and does not restrict the interface between the first container 502 and the heat transfer membrane 506 and the shelf surface 322. The reusable mechanism is designed to pinch close the connection tubing 508 when the lyophilizer mechanism activates at the end of the drying cycle. The freeze dryer 452 used for the lyophilization may be a validated clean in place (CIP), steam in place (SIP) freeze dryer, but the described closed system of the assembly allows for operation in a non-CIP/non-SIP lyophilization environment. Once loaded, the freeze dryer cycle is started. This cycle generally cools the human plasma to near −45° C. and freezing for 2 to 8 hours, followed by cooling of the freeze dryer condenser and application of vacuum to start the freeze drying cycle. To insure that the first collapsible container 502 stays in sufficient contact with the heat transfer surface 322 during the freeze-drying process, the first collapsible container 502 may contain an internal support structure (not shown), and/or the container 502 may be produced from a thicker, more resilient material than previously used. As a result, freeze-dried human plasma is formed in situ within the first collapsible container 502 (see FIG. 66).

The representative parameters for the freeze-drying process have been previously described and are incorporated herein by reference.

Throughout the freeze drying process, the gas permeable membrane 506 located on the second collapsible container 502 accommodates passage of gases, e.g., water vapor as it sublimates from the liquid plasma during freeze-drying, but otherwise prevents passage of liquid plasma from the first collapsible container 502. The second collapsible container 504 can expand or collapse without effecting or altering the contact of the first collapsible container 502 with the freeze dryer shelf 322. The container 502 does not have the semi-porous membrane 506 located directly on the container 502, thereby providing a permanent, air-tight seal for the container 502 through administration of reconstituted plasma, without having to transfer freeze-dried plasma from the first container 502 to an alternate container for reconstitution or administration. This can lead to increased sterility insurance.

The container 502 may also be vacuum packed and a sealing mechanism, as shown by example in FIGS. 67A-69B, could be used while the first collapsible container 502 is still under vacuum (FIG. 66), which would result in a very tightly packaged container. At the end of the freeze-drying process, the stoppering mechanism closes off the tubing 508 while there still is a vacuum within the freeze-dryer or the stoppering mechanism closes off the tubing 508 after the vacuum within the freeze-dryer has been broken by an inert gas, $CO_2$, or a combination of the two.

Once the freeze-drying process has been completed, the system 500 will be removed from the freezer and the second collapsible container 504 will be removed from the first collapsible container 502 in a manner that will insure the tubing 508 and the fluid pathway 514 are sealed. FIGS. 66A-69 depict various methods and closure devices for sealing and closing the tubing 508 after the system 500 has been through the freeze-drying process, with each of the processes providing a permanent and air-tight seal for the first collapsible container 502. It should be noted that the assembly 500 will be removed from the freeze-dryer with the first container 502, the second container 504, and the tubing 508 still connected, with the desired closure mechanism in place on the tubing and maintaining positive closure between the containers 502 and 504.

FIG. 66A shows a cross-sectional view of the tubing 508 being arranged to receive a pinch-point mechanism 530. The pinch-point mechanism 530 generally comprises a pinching component 532 and an inset 534 having a surface 536 that receives the pinching component 532. The surface 536 can be a softer material than the rest of the mechanism 530 to ease in the pinching process.

Figure 70:
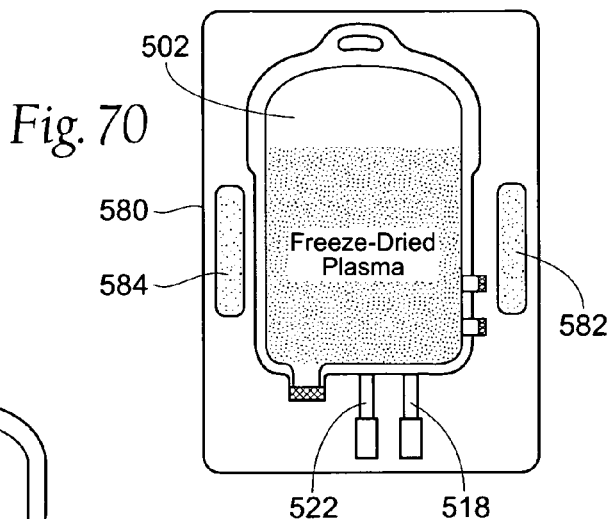
FIG. 70 is a front elevation view of the device of FIG. 64 containing plasma after it has been freeze-dried and with the secondary lyophilizing portion being removed.

FIG. 66B shows the mechanism 530 pinching down on the tubing 508 to seal shut the tubing 508 and the fluid pathway 530. Once the mechanism 530 is secured in place, the tube 508 can be heat sealed and severed, as shown in FIG. 70, to further insure an air-tight seal for the container 502.

FIG. 67A shows an alternate mechanism 540 for pinching and sealing the tubing 508. The mechanism 540 generally comprises a pinching member 542 and a hinged member 544. The hinged member 544 has two arms 546, pivotally connected by a hinge 548. Rolling members 550 are positioned along the arms 546 to assist in the mechanism 540 providing a tight seal on the tubing 508.

As shown in FIG. 67B, the pinching member 542 is forced downwardly into the tubing 508 into the hinged member 544. The arms 546 pivot upwardly, with the rolling members 550 assisting in the arms moving inwardly toward one another, thereby providing the necessary seal. The tubing 508 can then be subjected to further heat sealing, as discussed with respect to FIG. 69.

FIG. 68A demonstrates another pinching mechanism 560 used for sealing the first collapsible container 502 and the tubing 508. The tubing 508 is folded over itself while it is being pinched, which may provide an easier pinching process. The pinching mechanism 560 generally forms a ratcheting mechanism that comprises a fixed portion 562 and a movable portion 564, and a guide member 566.

As shown in FIG. 68B, the movable portion 564 is moved downwardly towards the fixed portion 562, with the guide member 566 providing support for the movable portion 564 and closing off the tubing 508. As with the other noted pinching and sealing mechanisms, the tubing 508 can then be subjected to further heat sealing, as discussed with respect to FIG. 69. It should be noted that a ratcheting mechanism as discussed with respect to FIGS. 68A-68B could also be incorporated into the pinching mechanisms 530 and 540, discussed in FIGS. 66A-B and FIGS. 67A-B, respectively, to provide the necessary air-tight seal of the tubing 508.

Figure 71:
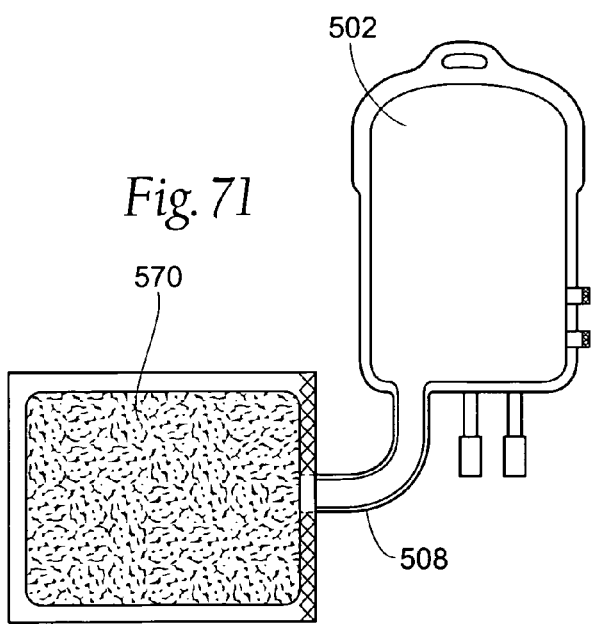
FIG. 71 provides a front elevation view of a second arrangement of the secondary portion of the alternate system and device for freeze-drying material, discussed above with respect to FIGS. 61-69.
Figure 72:
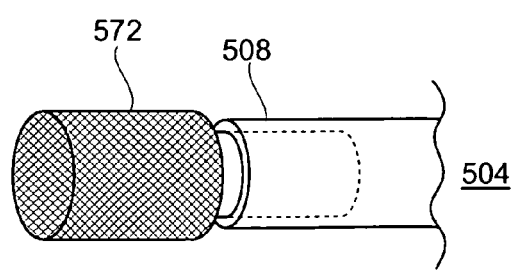
FIG. 72 provides a front elevation view of a further arrangement of the secondary portion of the alternate system and device for freeze-drying material, discussed above with respect to FIGS. 61-69

It should be noted that the first collapsible container 502 is independently shaped and formed from the second collapsible container 504 and the permeable membrane 506 that is supported by the second container 504. Conversely, the design of the second container 504 and the permeable membrane 506 can be altered as well. FIGS. 71 and 72 show alternate embodiments for the system 500, where the second collapsible container is not used, but tubing 508 is directly connected to a permeable membrane 570 (FIG. 71) or the tubing 508 is mated with a filter 572 (FIG. 72), with the filter possibly being a commercially available filter known in the art. For example, the filter media may comprise a hydrophobic polymer, such as a polypropylene, polyester, polyethylene, polyurethane, polyvinylidene fluoride or polytetrafluoroethylene material. The permeable membrane 570 will be sealed around the tubing 508 or the filter 572, preferably by heat sealing so that The permeable membrane 570 will function similarly to the membrane 506 and the previous membranes discussed in the freeze-drying process, and can be severed from the first collapsible container 502 as discussed with respect to FIGS. 67A-69B.

FIG. 70 provides the first collapsible container 502 filled with plasma after the freeze-drying and sealing process. The collapsible container 502 can be stored within a pouch 580 designed with a minimum or low moisture vapor transmission rate (MVTR). The pouch may also have oxygen absorbers 582 and water absorbers 584 to aid in protecting the dried plasma from exposure to water and oxygen during storage. An administration port 518 is located on the first collapsible container 502, for delivery of reconstituted plasma to a patient, generally as depicted and discussed previously (see e.g., FIGS. 16, 32, and 60). The administration port 518 preferably has a standard blood bag aseptic connection arrangement, with a typical blood bag spike 520. The port 518 is sealed until the container 502 will be administered to a patient. The first collapsible container 502 further supports a reconstitution port 522, also preferably with a standard blood bag aseptic connection arrangement for attaching the container 502 to a liquid container, as similarly described with respect to FIGS. 31 and 60.

In use at a remote site (see FIG. 73), the transfer set 462 is coupled to the container 464 of sterile reconstituting liquid (e.g., water) and the first collapsible container 502. The transfer set 462 can include plastic needles or spikes at each end to make the coupling, e.g., as shown in FIG. 30. The transfer set 462 may be long and flexible (as previously shown in FIG. 57). Alternatively, the transfer set 462 can be short and rigid, to reduce storage space and simplify handling.

The caregiver can now proceed to manipulate the container 464, to transfer the reconstituting liquid from the container 464 into contact with the freeze-dried material within the first collapsible container 502 to mix the reconstituting liquid 206 and the freeze-dried material within the first collapsible container 502, in preparation for administration to an individual.

Figure 73:
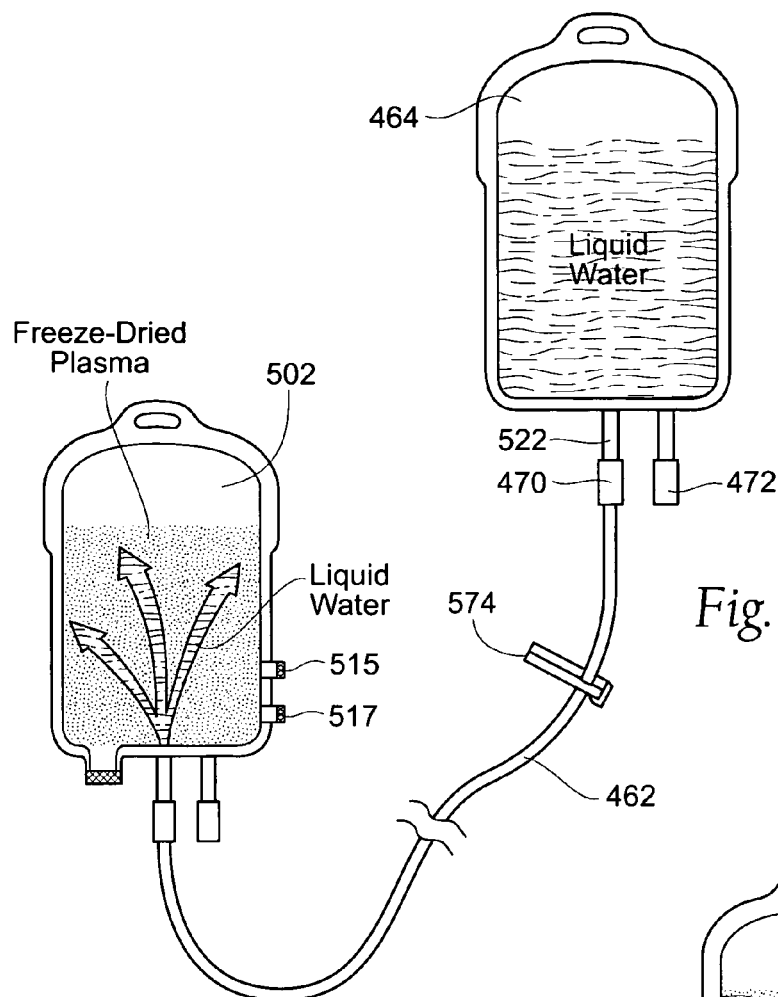
FIG. 73 shows the mixing of freeze-dried plasma material with a reconstituting liquid so that the plasma material and the reconstituting liquid can be mixed so that they are ready for administration.
Figure 74:
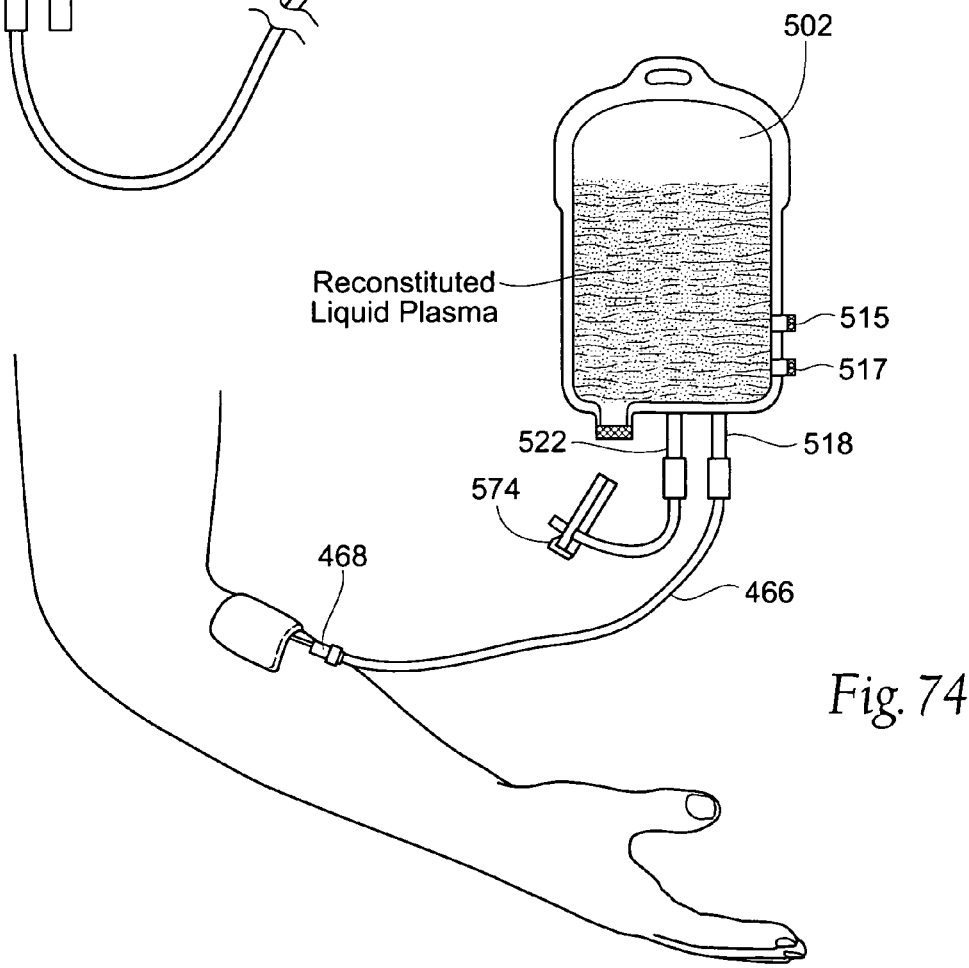
FIG. 74 shows the administration to an individual of freeze-died plasma material reconstituted using a unitary freeze-dried material storage assembly as shown in FIG. 70.

FIGS. 73 and 74 demonstrate that the first collapsible container 502 is similar in appearance to a typical blood bag known and used in the industry, thereby providing a familiar container for a caregiver to administer the reconstituted plasma. In FIG. 73, the reconstituted material is administered from the first collapsible container 502 that initially contained the liquid plasma prior to freeze-drying, which then subsequently contained the freeze-dried plasma after freeze drying. A pinch valve 574 located on the administration set 462 used for mixing is closed, thereby preventing further transfer of fluid from the associated port 470. The administration set 462 may then be severed and sealed. At this time, as shown in FIG. 74, the caregiver couples the administration port 522 on the first collapsible container 502 to the administration set 466, for transfer of the reconstituted material to the circulatory system of an individual, as shown in FIG. 74. The administration set 466 includes the phlebotomy needle 468 for insertion into a vein, in the same manner as before described with reference to FIG. 16, 32 or 60.

VIII. Conclusion

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:
1. An apparatus for freeze-drying a plasma material, said apparatus comprising:
   a first collapsible container containing the plasma material during freeze-drying and wherein the first collapsible container is without a permeable membrane;
   a removable second container comprising a permeable membrane; and
   a tubing connecting the first collapsible container to the removable second container;
   wherein the permeable membrane is separate from said first collapsible container.

2. The apparatus according to claim 1, wherein the removable second container is flexible.

3. The apparatus according to claim 1, wherein the first collapsible container further comprises a plasma material intake port for receiving a the plasma material.

4. The apparatus according to claim 3, wherein said fluid intake port is located on the tubing.

5. The apparatus according to claim 1, wherein the first collapsible container further comprises an administration port.

6. The apparatus according to claim 1, wherein the first collapsible container further comprises a reconstitution port.

7. The apparatus according to claim 1, wherein the permeable membrane comprises a polypropylene, polyester, polyethylene, polyurethane, polyvinylidene fluoride or polytetrafluoroethylene material.

8. The apparatus according to claim 1, wherein the first collapsible container further comprises a port for receiving a pH adjustment solution.

9. The apparatus according to claim 8, wherein the pH adjustment solution includes at least one of an acid or a buffer solution.

10. The apparatus according to claim 9, wherein the pH adjustment solution includes ascorbic acid.

11. The apparatus according to claim 1, further comprising a pouch for storing the first collapsible container.

12. The apparatus according to claim 11, wherein the pouch further comprises a low moisture vapor transfer rate (MVTR) material.

13. The apparatus according to claim 12, further comprising an oxygen absorber located in the pouch.

14. The apparatus according to claim 12, further comprising a water absorber located in the pouch.

15. The apparatus according to claim 1, further comprising a closure device.

16. The apparatus according to claim 15, wherein the closure device includes a pinching component and is located on the tubing.

17. The apparatus according to claim 15, wherein the closure device includes a hinged member located on the tubing.

18. The apparatus according to claim 16, wherein the closure device includes a ratcheting mechanism and is located on the tubing.

19. The apparatus according to claim 1, wherein the removable second container is collapsible.

20. The apparatus according to claim 1, wherein the removable second container is not collapsible.

21. The apparatus according to claim 1, wherein the tubing allows vapor transfer from the first collapsible container to the removable second container during freeze-drying.

22. The apparatus according to claim 1, wherein the tubing has a diameter of approximately one to two centimeters.

23. The apparatus according to claim 1, wherein the tubing is at least one of pinched, closed, sealed, and severed.

24. The apparatus according to claim 1, wherein at least one of pinching, closing, and sealing the tubing provides a permanent, air-tight seal for the plasma contained in the first collapsible container.

25. The apparatus according to claim 1, wherein the tubing is integrally formed with the first collapsible container.

26. The apparatus according to claim 1, wherein the tubing is a separate element connected to the first collapsible container.

27. The apparatus according to claim 1, further comprising a heat transfer membrane.

28. The apparatus according to claim 1, further comprising an internal support structure.

29. The apparatus according to claim 1, wherein the first collapsible container contains the plasma material during storage, reconstitution, and administration.

30. An apparatus for freeze-drying a plasma material, said apparatus comprising:
a first collapsible container containing the plasma material during freeze-drying and wherein the first collapsible container is without a permeable membrane;
a removable second container comprising a permeable membrane;
a tubing connecting the first collapsible container to the removable second container; and
a closure device on the tubing.

31. The apparatus according to claim 30, wherein the removable second container is flexible.

32. The apparatus according to claim 30, wherein the first collapsible container further comprises at least one of a plasma material intake port for receiving the plasma material, an administration port, a reconstitution port, and a port for receiving a pH adjustment solution.

33. The apparatus according to claim 30, wherein the closure device includes at least one of a pinching component located on the tubing, a hinged member located on the tubing, and a ratcheting mechanism located on the tubing.

34. The apparatus according to claim 30, wherein the removable second container is collapsible.

35. The apparatus according to claim 30, wherein the removable second container is not collapsible.

36. The apparatus according to claim 30, wherein the tubing allows vapor transfer from the first collapsible container to the removable second container during freeze-drying.

37. The apparatus according to claim 30, wherein at least one of pinching, closing, and sealing the tubing provides a permanent, air-tight seal for the plasma contained in the first collapsible container.

38. The apparatus according to claim 30, further comprising a heat transfer membrane.

39. The apparatus according to claim 30, further comprising an internal support structure.

40. The apparatus according to claim 30, wherein the first collapsible container contains the plasma material during storage, reconstitution, and administration.

41. An apparatus for freeze-drying a plasma material, said apparatus comprising:
a first collapsible container containing the freeze-dried plasma material and wherein the first collapsible container is without a permeable membrane;
a removable second container comprising a permeable membrane; and
a sealed tubing connecting the first collapsible container to the removable second container, wherein the sealed tubing provides a permanent, air-tight seal for the freeze-dried plasma contained in the first collapsible container.

42. The apparatus according to claim 41, wherein the removable second container is flexible.

43. The apparatus according to claim 41, wherein the first collapsible container further comprises at least one of a plasma material intake port for receiving the plasma material, an administration port, a reconstitution port, and a port for receiving a pH adjustment solution.

44. The apparatus according to claim 41, further comprising a closure device.

45. The apparatus according to claim 44, wherein the closure device includes at least one of a pinching component located on the tubing, a hinged member located on the tubing, and a ratcheting mechanism located on the tubing.

46. The apparatus according to claim 41, wherein the removable second container is collapsible.

47. The apparatus according to claim 41, wherein the removable second container is not collapsible.

48. The apparatus according to claim 41, further comprising a heat transfer membrane.

49. The apparatus according to claim 41, further comprising an internal support structure.

50. The apparatus according to claim 41, wherein the first collapsible container contains the plasma material during storage, reconstitution, and administration.

51. A method for freeze-drying a plasma material comprising providing the apparatus of claim 1.

52. The method of claim 51, further comprising providing a closure device located on the tubing and pinching, closing, and sealing the tubing.

53. The method of claim 51, further comprising allowing vapor transfer from the first collapsible container to the removable second container via the tubing during freeze-drying.

54. The method of claim 51, further comprising containing the plasma material within the first collapsible container during storage, reconstitution, and administration.

55. A method for freeze-drying a plasma material comprising providing the apparatus of claim 30.

56. The method of claim 55, further comprising allowing vapor transfer from the first collapsible container to the removable second container via the tubing during freeze-drying.

57. The method of claim 55, further comprising pinching, closing, and sealing the tubing.

58. The method of claim 55, further comprising containing the plasma material within the first collapsible container during storage, reconstitution, and administration.

59. A method for freeze-drying a plasma material comprising providing the apparatus of claim 41.

60. The method of claim 59, further comprising providing a closure device located on the tubing.

61. The method of claim 59, further comprising containing the freeze-dried plasma material within the first collapsible container during storage, reconstitution, and administration.

* * * * *